US012790594B2

(12) United States Patent
Hewson et al.

(10) Patent No.: US 12,790,594 B2
(45) Date of Patent: Nov. 10, 2026

(54) HANTAVIRUS ANTIGENIC COMPOSITION

(71) Applicant: SECRETARY OF STATE FOR HEALTH AND SOCIAL CARE, London (GB)

(72) Inventors: Roger Hewson, Salisbury (GB); Stuart Dowall, Salisbury (GB); Emma Kennedy, Salisbury (GB); Miles Carroll, Salisbury (GB)

(73) Assignee: SECRETARY OF STATE FOR HEALTH AND SOCIAL CARE, London (GB)

( * ) Notice: Subject to any disclaimer, the term of this patent is extended or adjusted under 35 U.S.C. 154(b) by 1263 days.

(21) Appl. No.: 17/631,416

(22) PCT Filed: Jul. 29, 2020

(86) PCT No.: PCT/GB2020/051813
§ 371 (c)(1),
(2) Date: Jan. 28, 2022

(87) PCT Pub. No.: WO2021/019235
PCT Pub. Date: Feb. 4, 2021

(65) Prior Publication Data

US 2022/0275346 A1 Sep. 1, 2022

(30) Foreign Application Priority Data

Jul. 29, 2019 (GB) ..................................... 1910804

(51) Int. Cl.
*C12N 7/00* (2006.01)
*C12N 5/071* (2010.01)
*C12N 5/0735* (2010.01)

(52) U.S. Cl.
CPC ............. *C12N 7/00* (2013.01); *C12N 5/0606* (2013.01); *C12N 5/0686* (2013.01); *C12N 2760/12134* (2013.01); *C12N 2760/12151* (2013.01); *C12N 2760/12162* (2013.01); *C12N 2800/107* (2013.01)

(58) Field of Classification Search
None
See application file for complete search history.

(56) References Cited

U.S. PATENT DOCUMENTS

2002/0114818 A1 8/2002 Schmaljohn et al.

FOREIGN PATENT DOCUMENTS

| | | | |
|---|---|---|---|
| JP | 2008-503720 | A | 2/2008 |
| WO | 9814585 | A1 | 4/1998 |
| WO | 2006/022461 | A1 | 3/2006 |
| WO | 2006/088478 | A2 | 8/2006 |
| WO | 2019/038332 | A1 | 2/2019 |

OTHER PUBLICATIONS

Xu X, et al. "Immunity to Hantavirus challenge in Meriones unguiculatus induced by vaccinia-vectored viral proteins", Am J Trop Med Hyg. Oct. 1992;47(4):397-404 (Year: 1992).*
Bucht, G., et al., "Modifying the Cellular Transport of DNA-Based Vaccines Alters the Immune Response to Hantavirus Nucleocapsid Protein," Vaccine 19(28-29):3820-3829, Jul. 2001.
Chu, Y-K., et al., "A Vaccinia Virus-Vectored Hantaan Virus Vaccine Protects Hamsters From Challenge With Hantaan and Seoul Viruses But Not Puumala Virus," Journal of Virology 69(10):6417-6423, Oct. 1995.
Safronetz, D., et al., "Adenovirus Vectors Expressing Hantavirus Proteins Protect Hamsters Against Lethal Challenge With Andes Virus," Journal of Virology 83(14):7285-7295, Jul. 2009.
Schmaljohn, C.S., et al., "Antigenic Subunits of Hantaan Virus Expressed by Baculovirus and Vaccinia Virus Recombinants," Journal of Virology 64(7):3162-3170, Jul. 1990.
Notice of Reasons for Rejection mailed Jul. 2, 2024, issued in related JP Application No. 2022-506337, filed Jul. 29, 2020, 10 pages.
International Preliminary Report on Patentability completed Nov. 12, 2021, issued in corresponding International Application No. PCT/GB2020/051813, filed Jul. 29, 2020, 37 pages.
International Search Report and Written Opinion mailed Mar. 26, 2021, issued in corresponding International Application No. PCT/GB2020/051813, filed Jul. 29, 2020, 32 pages.
Kamrud, K.I., et al., "Comparison of the Protective Efficacy of Naked DNA, DNA-based Sindbis Replicon, and Packaged Sindbis Replicon Vectors Expressing Hantavirus Structural Genes in Hamsters," Virology Division, United States Army Medical Research Institute of Infectious Diseases, vol. 263, 1999, pp. 209-219.
Li, K., "Induction of Hantaan Virus-Specific Immune Responses in C57BL/6 Mice by Immunization with a Modified Recombinant Adenovirus Containing the Chimeric Gene, GeSo.7," International Journal of Molecular Medicine, vol. 32, 2013, pp. 709-716.
Masanori, T., et al., "Generation of recombinant vaccinia viruses expressing Puumala virus proteins and use in isolating cytotoxic T cells specific for Puumala virus," Virus Research, vol. 84, 2002, pp. 67-77, Elsevier.
Morii, M., et al., "Antigenic Characterization of Hantaan and Seoul Virus Nucleocapsid Proteins Expressed by Recombinant Baculovirus: Application of a Truncated Protein, Lacking an Antigenic Region Common to the Two Viruses, as a Serotyping Antigen," Journal of Clinical Microbiology, vol. 36, No. 9, Sep. 1998, pp. 2514-2521, American Society for Microbiology.
Ura, T., et al., "Developments in Viral Vector-Based Vaccines," Vaccines, vol. 2, 2014, pp. 624-641.

(Continued)

*Primary Examiner* — Peter Johansen
(74) *Attorney, Agent, or Firm* — Christensen O'Connor Johnson Kindness PLLC

(57) ABSTRACT

The present invention provides a viral vector or bacterial vector, said vector comprising a nucleic acid sequence encoding a Hantavirus nucleoprotein or antigenic fragment thereof; wherein said vector is capable of inducing a protective immune response in a subject. The present invention also provides compositions and uses of the vector in methods of medical treatment.

21 Claims, 9 Drawing Sheets

Figure 1:
Figure 1:
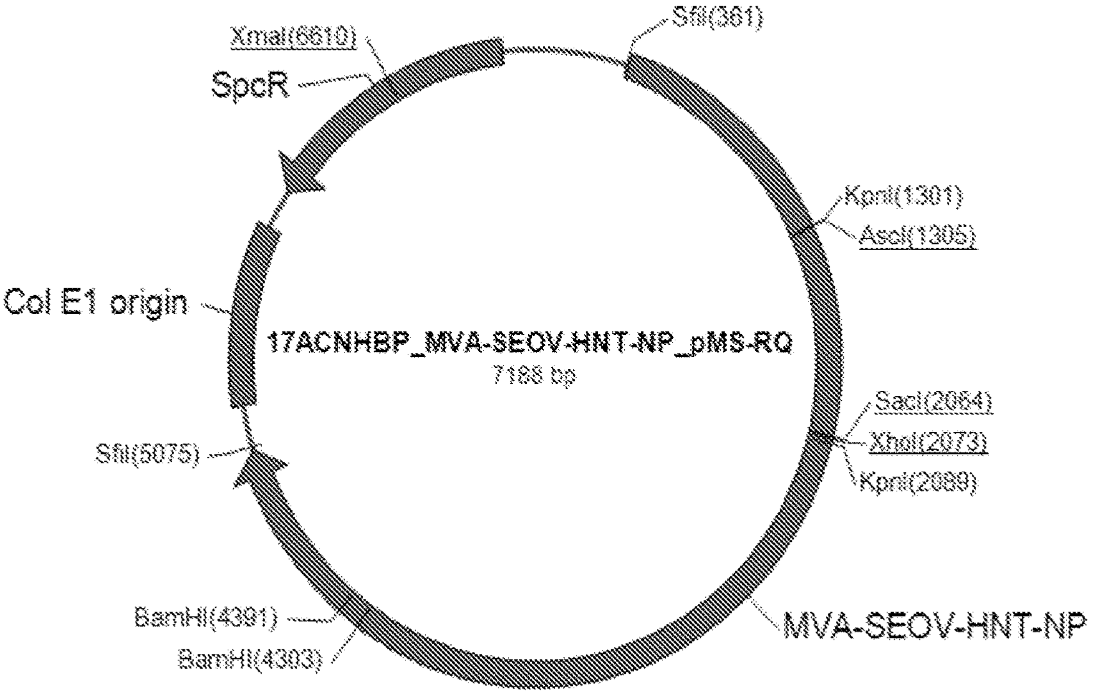

Specification includes a Sequence Listing.

(56) References Cited

OTHER PUBLICATIONS

Xiao, X., et al., "Immunity to Hantavirus Challenge in Meriones Unguiculatus Induced by Vaccinia-Vectored Viral Proteins," American Journal of Tropical Medicine and Hygiene, vol. 47, No. 4, 1992, pp. 397-404, The American Society of Tropical Medicine and Hygiene.

Zhao, C., et al., "Immunogenicity of a multi-epitope DNA vaccine against hantavirus," Human Vaccines & Immunotherapeutics, vol. 8, No. 2, Feb. 2012, pp. 208-215, Landes Bioscience.

* cited by examiner (a)

(b)

HANTAVIRUS ANTIGENIC COMPOSITION

CROSS-REFERENCES TO RELATED APPLICATIONS

This application is a National Stage of International Application No. PCT/GB2020/051813, filed Jul. 29, 2020, which claims the benefit of GB Application No. 1910804.2, filed Jul. 29, 2019, the contents of which are incorporated herein by reference in their entirety for all purposes.

The present invention relates to viral vectors and bacterial vectors comprising Hantavirus antigens and their use in immunogenic and antigenic compositions. The present invention also relates to prophylactic uses of said compositions. The present invention also relates to immunogen for use in raising therapeutic antibodies, and methods for producing said immunogen.

Hantavirus is an emerging zoonotic virus with worldwide distribution. There are numerous Hantavirus strains falling broadly into three serogroups. Hantavirus is the causative agent of Hantavirus pulmonary syndrome (HPS), a severe respiratory disease in humans that is typically fatal in 36% of cases, and a mortality rate of 50% has been recorded during some outbreaks. It is also the causative agent of hemorrhagic fever with renal syndrome (HFRS), a group of clinically similar illnesses that can be fatal in up to 15% of cases. Hantavirus is typically transmitted to humans by exposure to aerosolised bodily fluids or faeces of infected small mammals, typically rodents. Person-to-person transmission has also been reported.

According to the Centres for Disease Control and Prevention (CDC), symptoms associated with Hantavirus infection include fever, headache, muscle ache, and severe difficulty in breathing. Symptoms associated with HPS may also include fatigue, chills, dizziness, non-productive cough, nausea, vomiting, and other gastrointestinal symptoms, as well as malaise, diarrhoea, light headedness, arthralgia, back pain, and abdominal pain. Symptoms associated with HFRS include intense headaches, back and abdominal pain, fever, chills, nausea, blurred vision, flushing of the face, inflammation or redness of the eyes, a rash. Later symptoms of HFRS can include low blood pressure, acute shock, vascular leakage, and acute kidney failure, which can cause severe fluid overload.

There is currently no licensed vaccine against Hantavirus. According to the CDC, there is no specific treatment or cure for Hantavirus infection, HPS or HFRS. Patients suffering from HPS are admitted to intensive care units and treated with intubation and oxygen therapy to aid the patient during severe respiratory distress. The success of HPS treatment depends on the severity of the respiratory distress and early detection of the infection. Treatment of HFRS may involve management of patient's fluid and electrolyte levels, oxygen and blood pressure levels, dialysis to correct severe fluid overload and treatment of any secondary infections. The antiviral drug ribavirin has been shown to decrease illness and death if used very early in the course of clinical illness with HFRS. However, no benefit of ribavirin has been found for patients with HPS.

There is therefore significant need for a protective vaccine against Hantavirus infection. There is also an urgent need for further therapeutics for the prevention, treatment and suppression of Hantavirus infection.

The present invention addresses one or more of the above problems by providing viral vectors and bacterial vectors encoding Hantavirus nucleoprotein (NP) or antigenic fragments thereof, together with corresponding compositions and uses of said vectors and compositions in the prevention and treatment of Hantavirus infection.

The vectors and compositions of the invention enable an immune response against Hantavirus to be stimulated (i.e. induced) in an individual (i.e. a subject) and provide improved immunogenicity and efficacy.

In one aspect, the invention provides a viral vector or bacterial vector, said vector comprising a nucleic acid sequence encoding a Hantavirus NP or antigenic fragment thereof, wherein said vector is capable of inducing an immune response in an individual. The present inventors have found that highly effective immune responses against Hantavirus can be generated in an individual by using a viral vector or bacterial vector to deliver to the subject nucleic acid sequences encoding Hantavirus NP (or antigenic fragments thereof).

In a preferred embodiment, the vector of the invention is a viral vector.

Hantaviruses are a genus of enveloped, single-stranded, tri-segmented, negative sense RNA viruses which belong to the Bunyaviridae family. More than 20 Hantavirus strains have been described that are pathogenic to humans, with each strain adapted to a single rodent species. Hantavirus strains are broadly classified as either Old World or New World. Old World strains include Seoul virus ("SEOV"; worldwide distribution), Puumala virus (predominantly European distribution), Hantaan virus ("HNT"; predominantly Asian distribution) and Dobrava virus (predominantly European distribution) and are typically associated with causing HFRS. New World strains include Sin Nombre virus (predominantly North American distribution) and Andes virus (predominantly Latin American distribution) and are typically associated with HPS.

The Hantavirus genome consists of three single-stranded RNA segments referred to as small (S), medium (M), and large (L). The S segment is between 1 and 3 kb and encodes the nucleocapsid protein (NP). The M segment is between 3.2 and 4.9 kb and encodes the glycoproteins (GPs), Gn and Gc. The L segment is between 6.8 and 12 kb and encodes viral RNA dependent RNA polymerase.

Hantavirus glycoproteins, Gn and Gc, play an important role in infection of target cells via interactions with specific entry receptors, e.g. integrins. Hantavirus NP forms a ribonucleoprotein complex with the viral polymerase and plays multiple roles in virus proliferation. NP has also been reported to play a role in enhancing translation of viral RNA by the host cell, downregulation of apoptosis, inhibition interferon signalling responses, and blocking TNFα-induced activation of NF-κB.

Seoul virus may be used as a reference Hantavirus strain. GenBank Accession number KM948598.1 provides a reference nucleic acid sequence for Hantavirus NP (see SEQ ID NO: 1) and a reference polypeptide sequence for Hantavirus NP (SEQ ID NO: 4).

(SEQ ID NO: 1)

```
TAGTAGTAGGCTCCCTAAAGAGCTACTACACTAACAAGGAAAATGGCAAC

TATGGAAGAAATCCAGAGAGAAATCAGTGCGCACGAGGGGCAGCTTGTAA

TAGCACGCCAGAAGGTCAAGGATGCAGAAAAGCAGTATGAGAAGGATCCT

GATGACCTAAATAAGAGGGCACTGCATGATCGGGAGAGTGTCGCAGCTTC

AATACAATCAAAAATTGATGAATTGAAGCGCCAACTTGCTGACAGGATTG

CAGCAGGGAAGAACATCGGGCAAGACCGGGATCCTACAGGGGTAGAGCCG
```

-continued

GGTGATCATCTCAAGGAAAGATCAGCACTAAGCTACGGGAATACACTGGA

CCTGAATAGCCTTGACATTGATGAACCTACAGGACAGACAGCTGATTGGT

TGACCATAATTGTCTATTTGACATCATTCGTGGTCCCGATCATCTTGAAG

GCACTGTACATGTTGACAACAAGAGGCAGGCAGACTTCAAAGGACAACAA

GGGAATGAGGATCAGATTCAAGGATGACAGCTCATATGAAGATGTCAATG

GAATCAGAAAGCCCAAACATCTGTATGTGTCAATGCCAAACGCCCAATCA

AGCATGAAGGCTGAAGAGATAACACCTGGAAGATTCCGCACTGCAGTATG

TGGGCTATACCCTGCACAGATAAAGGCAAGGAACATGGTAAGCCCTGTCA

TGAGTGTAGTTGGGTTTTTGGCACTGGCAAAAGACTGGACATCTAGAATT

GAAGAATGGCTTGGTGCACCCTGCAAGTTCATGGCAGAGTCTCCCATTGC

CGGGAGCTTATCTGGGAATCCTGTGAATCGTGATTATATCAGACAGAGAC

AAGGTGCACTTGCAGGGATGGAGCCAAAAGAATTTCAAGCTCTCAGGCAA

CATTCAAAGGATGCTGGATGTACACTGGTTGAACATATTGAGTCACCATC

ATCAATATGGGTATTTGCTGGGGCCCCTGATAGGTGCCCACCGACATGCC

TGTTTGTTGGAGGGATGGCTGAGTTAGGTGCTTTCTTTTCTATACTTCAG

GATATGAGGAACACAATCATGGCTTCAAAGACTGTGGGAACAGCTGATGA

AAAGCTTCGAAAGAAGTCATCATTCTATCAATCATACCTCAGACGCACAC

AATCAATGGGAATACAACTGGACCAGAGGATAATTGTTATGTTTATGGTT

GCCTGGGGAAAGGAGGCAGTGGACAACTTTCATCTCGGTGATGACATGGA

TCCAGAGCTTCGCAGCCTGGCTCAGATCCTGATTGACCAGAAAGTGAAGG

AAATCTCAAACCAGGAACCTATGAAATTATAAGTACATAATTATGTAATC

CATACTAACTATAGGTTAAGAAATACTAATCATTAGTTAATAAGAATATA

GATTTATTGAATAATCATATTAAATAATTAGGTAAGTTAACTATTAGTTA

GTTAAGTTAGCTAATTGATTTATATGATTATCACAATTGAATGTAATCAT

AAGCACAATCACTGCCATGTATAATCACGGGTATACGGGTGGTTTTCATA

TGGGGAACAGGGTGGGCTTAGGGCCAGGTCACCTTAAGTGACCTTTTTTG

TATATATGGATGTAGATTTCAATTGATCGAGTACTAATCCTACTGTTCTC

TTTTCCTTTCCTTTCTCCTTCTTTACTAACAACAACAAACTACCTCACAA

CCTTCTACCTCAACACATACTACCTCATTCAGTTGTTTCCTTTTGTCTTT

TTAGGGAGCATACTACTA

The coding sequence of SEQ ID NO: 1 corresponds to nucleic acid residues 43-1332 therein, and is represented by SEQ ID NO: 2:

(SEQ ID NO: 2)

ATGGCAACTATGGAAGAAATCCAGAGAGAAATCAGTGCGCACGAGGGGCA

GCTTGTAATAGCACGCCAGAAGGTCAAGGATGCAGAAAAGCAGTATGAGA

AGGATCCTGATGACCTAAATAAGAGGGCACTGCATGATCGGGAGAGTGTC

GCAGCTTCAATACAATCAAAAATTGATGAATTGAAGCGCCAACTTGCTGA

CAGGATTGCAGCAGGGAAGAACATCGGGCAAGACCGGGATCCTACAGGGG

TAGAGCCGGGTGATCATCTCAAGGAAAGATCAGCACTAAGCTACGGGAAT

ACACTGGACCTGAATAGCCTTGACATTGATGAACCTACAGGACAGACAGC

-continued

TGATTGGTTGACCATAATTGTCTATTTGACATCATTCGTGGTCCCGATCA

TCTTGAAGGCACTGTACATGTTGACAACAAGAGGCAGGCAGACTTCAAAG

GACAACAAGGGAATGAGGATCAGATTCAAGGATGACAGCTCATATGAAGA

TGTCAATGGAATCAGAAAGCCCAAACATCTGTATGTGTCAATGCCAAACG

CCCAATCAAGCATGAAGGCTGAAGAGATAACACCTGGAAGATTCCGCACT

GCAGTATGTGGGCTATACCCTGCACAGATAAAGGCAAGGAACATGGTAAG

CCCTGTCATGAGTGTAGTTGGGTTTTTGGCACTGGCAAAAGACTGGACAT

CTAGAATTGAAGAATGGCTTGGTGCACCCTGCAAGTTCATGGCAGAGTCT

CCCATTGCCGGGAGCTTATCTGGGAATCCTGTGAATCGTGATTATATCAG

ACAGAGACAAGGTGCACTTGCAGGGATGGAGCCAAAAGAATTTCAAGCTC

TCAGGCAACATTCAAAGGATGCTGGATGTACACTGGTTGAACATATTGAG

TCACCATCATCAATATGGGTATTTGCTGGGGCCCCTGATAGGTGCCCACC

GACATGCCTGTTTGTTGGAGGGATGGCTGAGTTAGGTGCTTTCTTTTCTA

TACTTCAGGATATGAGGAACACAATCATGGCTTCAAAGACTGTGGGAACA

GCTGATGAAAAGCTTCGAAAGAAGTCATCATTCTATCAATCATACCTCAG

ACGCACACAATCAATGGGAATACAACTGGACCAGAGGATAATTGTTATGT

TTATGGTTGCCTGGGGAAAGGAGGCAGTGGACAACTTTCATCTCGGTGAT

GACATGGATCCAGAGCTTCGCAGCCTGGCTCAGATCCTGATTGACCAGAA

AGTGAAGGAAATCTCAAACCAGGAACCTATGAAATTA

The inventors have generated a nucleic acid sequence encoding Hantavirus NP that is optimised for expression in *Homo sapiens* (see SEQ ID NO: 3):

(SEQ ID NO: 3)

ATGGCCACAATGGAAGAGATCCAGAGAGAGATCAGCGCCCACGAGGGACA

GCTGGTTATCGCCAGACAGAAAGTGAAGGACGCCGAGAAGCAGTACGAGA

AGGACCCCGACGATCTGAACAAGAGAGCCCTGCACGACAGAGAAAGCGTG

GCCGCCTCTATCCAGAGCAAGATCGATGAGCTGAAGAGACAGCTGGCCGA

CAGAATCGCCGCTGGCAAGAATATTGGCCAGGACAGAGATCCCACAGGCG

TGGAACCTGGCGATCACCTGAAAGAGAGAAGCGCCCTGTCCTATGGCAAC

ACCCTGGACCTGAACAGCCTGGACATTGATGAGCCTACCGGCCAGACAGC

CGACTGGCTGACAATCATTGTGTACCTGACCAGCTTCGTGGTCCCCATCA

TCCTGAAGGCCCTGTACATGCTGACCACCAGAGGCAGACAGACCAGCAAG

GACAACAAGGGCATGAGAATCCGGTTCAAGGATGACAGCAGCTACGAGGA

CGTGAACGGCATTAGAAAGCCCAAGCACCTGTACGTGTCCATGCCTAACG

CTCAGAGCAGCATGAAGGCCGAGGAAATCACCCCTGGCAGATTCAGAACA

GCCGTGTGCGGACTGTACCCCGCTCAGATCAAGGCCAGAAACATGGTGTC

CCCAGTGATGAGCGTCGTGGGATTTCTGGCCCTGGCTAAGGACTGGACCA

GCAGGATTGAGGAATGGCTGGGAGCCCCCTTGCAAGTTTATGGCCGAGTCT

CCTATCGCCGGCAGCCTGTCTGGCAACCCCGTGAATAGAGACTACATCAG

ACAGAGGCAGGGCGCTCTGGCCGGAATGGAACCCAAAGAATTTCAGGCCC

TGCGGCAGCACTCTAAGGATGCCGGATGTACCCTGGTGGAACACATTGAG

-continued

AGCCCCAGCAGCATCTGGGTTTTCGCTGGCGCTCCTGATAGATGCCCTCC

TACCTGTCTGTTTGTTGGCGGAATGGCCGAGCTGGGCGCCTTCTTTAGCA

TTCTGCAGGACATGCGGAATACCATCATGGCCAGCAAGACCGTGGGCACC

GCCGATGAGAAGCTGAGAAAGAAGTCCAGCTTCTACCAGAGCTACCTGCG

GAGAACCCAGAGCATGGGCATTCAGCTGGACCAGAGAATCATCGTGATGT

TCATGGTGGCCTGGGGCAAAGAAGCCGTGGACAATTTTCACCTGGGCGAC

GACATGGACCCCGAGCTGAGATCTCTGGCCCAGATCCTGATCGACCAGAA

AGTCAAAGAGATCTCCAATCAAGAGCCCATGAAGCTG

Translation of the nucleic acid sequence of SEQ ID NO: 2 or SEQ ID NO: 3 yields a Hantavirus NP polypeptide sequence, which is represented by (SEQ ID NO: 4):

(SEQ ID NO: 4)

MATMEEIQREISAHEGQLVIARQKVKDAEKQYEKDPDDLNKRALHDRESV

AASIQSKIDELKRQLADRIAAGKNIGQDRDPTGVEPGDHLKERSALSYGN

TLDLNSLDIDEPTGQTADWLTIIVYLTSFVVPIILKALYMLTTRGRQTSK

DNKGMRIRFKDDSSYEDVNGIRKPKHLYVSMPNAQSSMKAEEITPGRFRT

AVCGLYPAQIKARNMVSPVMSVVGFLALAKDWTSRIEEWLGAPCKFMAES

PIAGSLSGNPVNRDYIRQRQGALAGMEPKEFQALRQHSKDAGCTLVEHIE

SPSSIWVFAGAPDRCPPTCLFVGGMAELGAFFSILQDMRNTIMASKTVGT

ADEKLRKKSSFYQSYLRRTQSMGIQLDQRIIVMFMVAWGKEAVDNFHLGD

DMDPELRSLAQILIDQKVKEISNQEPMKL

Hantaan virus may be used as a reference Hantavirus strain. GenBank Accession number KC570390.1 provides a reference nucleic acid sequence for Hantavirus NP (see SEQ ID NO: 5) and a reference polypeptide sequence for Hantavirus NP (See SEQ ID NO: 7).

(SEQ ID NO: 5)

TAGTAGTAGACTCCCTAAAGAGCTACTAGAACAACGATGGCAACTATGGA

GGAATTGCAGAGGGAAATCAATGCCCATGAGGGTCAACTGGTGATAGCCA

GGCAGAAGGTGAGGGATGCAGAAAAGCAGTATGAAAAGGATCCAGATGAG

TTAAACAAGAGAGCATTGACAGATCGAGAGGGTGTTGCAGTATCCATTCA

AGCAAAGATTGATGAGTTAAAGAGGCAATTGGCAGATAGGATTGCAACCG

GGAAGAACCTTGGAAAGGAACAAGACCCAACAGGGGTAGAACCTGGAGAT

CATCTGAAAGAGAGATCAATGCTCAGTTATGGAAATGTTCTTGACTTAAA

CCACCTGGATATTGATGAGCCAACAGGACAGACAGCAGACTGGCTGGGCA

TTGTTATCTATCTCACATCCTTTGTTGTCCCGATACTTCTGAAAGCCCTG

TACATGTTAACAACAAGAGGGAGGCAGACCACCAAGGACAATAAAGGAAC

TCGGATTCGATTCAAGGATGATAGCTCCTTCGAGGATGTCAATGGCATTC

GGAAGCCGAAACATCTATATGTGTCCTTACCAAATGCACAGTCAAGTATG

AAAGCAGAAGAGATTACACCTGGTAGATATAGAACAGCAATTTGTGGACT

TTACCCTGCACAAATTAAGGCAAGACAGATGATTAGTCCAGTCATGAGTG

TAATCGGATTCTTGGCTTTGGCAAAAGATTGGAGTGACCGCATTGAGCAG

-continued

TGGTTAAGTGAACCGTGTAAGCTTCTTCCAGATACAGCAGCAGTTAGCCT

TCTTGGTGGTCCTGCAACCAACAGGGACTATTTACGGCAGCGACAAGTAG

CATTGGGCAACATGGAAACAAAAGAGTCTAAGGCTATACGCCAACATGCA

GAAGCAGCAGGCTGTAGTATGATTGAGGACATTGAGTCACCATCATCAAT

ATGGGTGTTTGCTGGGGCACCGGACCGCTGTCCACCAACATGTCTCTTTA

TTGCAGGTATGGCTGAGCTTGGGGCATTTTTTTCCATCCTGCAGGACATG

CGAAATACAATTATGGCATCCAAGACAGTTGGAACCTCTGAGGAGAAGCT

ACGGAAGAAATCCTCATTCTATCAGTCTTATCTCAGGAGAACACAATCAA

TGGGAATACAACTGGATCAGAGGATAATTGTGCTCTTCATGGTAGCCTGG

GGGAAAGAAGCAGTGGATAACTTCCACCTAGGAGATGATATGGACCCTGA

GCTGCGAACACTAGCACAGAGCCTGATTGATGTTAAAGTGAAGGAAATTT

CCAACCAAGAGCCTTTAAAACTATAATCAGTGAATGTATAACCCTCATTA

TGTGATTATTATATACTACTGAATCATTATCAATCATATTTGCACTATTA

TTATCAGGGGAATTAGTATATCAGGGTAAGGGCACATTTATGGGTGGGAA

TCATTACTCAGAGGGTGGGTCAGTTAATCCGTTGTGGGTGGGTTTAGTTC

CTGGCTGCCTTAAGTAGCCTTTTTTTGTATATATGGATGTAGATTTCATT

TGATCTTTAAACTAATCTTGCTCTTTTTCCTTTTCCTCCTGCTTTCTCTG

CTTACTAACAACAACATTCTACCTCAACACACAACTACCTCAACTAAACT

ACCTCATTTGATTGCTCCTTGATTGTCTCTTTAGGGAGTCTACTACTA

The coding sequence of SEQ ID NO: 5 corresponds to nucleic acid residues 37-1323 therein, and is represented by SEQ ID NO: 6.

(SEQ ID NO: 6)

ATGGCAACTATGGAGGAATTGCAGAGGGAAATCAATGCCCATGAGGGTCA

ACTGGTGATAGCCAGGCAGAAGGTGAGGGATGCAGAAAAGCAGTATGAAA

AGGATCCAGATGAGTTAAACAAGAGAGCATTGACAGATCGAGAGGGTGTT

GCAGTATCCATTCAAGCAAAGATTGATGAGTTAAAGAGGCAATTGGCAGA

TAGGATTGCAACCGGGAAGAACCTTGGAAAGGAACAAGACCCAACAGGGG

TAGAACCTGGAGATCATCTGAAAGAGAGATCAATGCTCAGTTATGGAAAT

GTTCTTGACTTAAACCACCTGGATATTGATGAGCCAACAGGACAGACAGC

AGACTGGCTGGGCATTGTTATCTATCTCACATCCTTTGTTGTCCCGATAC

TTCTGAAAGCCCTGTACATGTTAACAACAAGAGGGAGGCAGACCACCAAG

GACAATAAAGGAACTCGGATTCGATTCAAGGATGATAGCTCCTTCGAGGA

TGTCAATGGCATTCGGAAGCCGAAACATCTATATGTGTCCTTACCAAATG

CACAGTCAAGTATGAAAGCAGAAGAGATTACACCTGGTAGATATAGAACA

GCAATTTGTGGACTTTACCCTGCACAAATTAAGGCAAGACAGATGATTAG

TCCAGTCATGAGTGTAATCGGATTCTTGGCTTTGGCAAAAGATTGGAGTG

ACCGCATTGAGCAGTGGTTAAGTGAACCGTGTAAGCTTCTTCCAGATACA

GCAGCAGTTAGCCTTCTTGGTGGTCCTGCAACCAACAGGGACTATTTACG

GCAGCGACAAGTAGCATTGGGCAACATGGAAACAAAAGAGTCTAAGGCTA

TACGCCAACATGCAGAAGCAGCAGGCTGTAGTATGATTGAGGACATTGAG

-continued

TCACCATCATCAATATGGGTGTTTGCTGGGGCACCGGACCGCTGTCCACC
AACATGTCTCTTTATTGCAGGTATGGCTGAGCTTGGGGCATTTTTTTCCA
TCCTGCAGGACATGCGAAATACAATTATGGCATCCAAGACAGTTGGAACC
TCTGAGGAGAAGCTACGGAAGAAATCCTCATTCTATCAGTCTTATCTCAG
GAGAACACAATCAATGGGAATACAACTGGATCAGAGGATAATTGTGCTCT
TCATGGTAGCCTGGGGGAAAGAAGCAGTGGATAACTTCCACCTAGGAGAT
GATATGGACCCTGAGCTGCGAACACTAGCACAGAGCCTGATTGATGTTAA
AGTGAAGGAAATTTCCAACCAAGAGCCTTTAAAACTA

Translation of the nucleic acid sequence of SEQ ID NO: 6 yields a Hantavirus NP polypeptide sequence, which is represented by (SEQ ID NO: 7):

(SEQ ID NO: 7)
MATMEELQREINAHEGQLVIARQKVRDAEKQYEKDPDELNKRALTDREGV
AVSIQAKIDELKRQLADRIATGKNLGKEQDPTGVEPGDHLKERSMLSYGN
VLDLNHLDIDEPTGQTADWLGIVIYLTSFVVPILLKALYMLTTRGRQTTK
DNKGTRIRFKDDSSFEDVNGIRKPKHLYVSLPNAQSSMKAEEITPGRYRT
AICGLYPAQIKARQMISPVMSVIGFLALAKDWSDRIEQWLSEPCKLLPDT
AAVSLLGGPATNRDYLRQRQVALGNMETKESKAIRQHAEAAGCSMIEDIE
SPSSIWVFAGAPDRCPPTCLFIAGMAELGAFFSILQDMRNTIMASKTVGT
SEEKLRKKSSFYQSYLRRTQSMGIQLDQRIIVLEMVAWGKEAVDNEHLGD
DMDPELRTLAQSLIDVKVKEISNQEPLKL

Reference nucleic acid sequence for Hantavirus NP may be provided by SEQ ID NO: 8, which corresponds to nucleic acid residues 319-1323 of SEQ ID NO: 5.

(SEQ ID NO: 8)
ATGCTCAGTTATGGAAATGTTCTTGACTTAAACCACCTGGATATTGATGA
GCCAACAGGACAGACAGCAGACTGGCTGGGCATTGTTATCTATCTCACAT
CCTTTGTTGTCCCGATACTTCTGAAAGCCCTGTACATGTTAACAACAAGA
GGGAGGCAGACCACCAAGGACAATAAAGGAACTCGGATTCGATTCAAGGA
TGATAGCTCCTTCGAGGATGTCAATGGCATTCGGAAGCCGAAACATCTAT
ATGTGTCCTTACCAAATGCACAGTCAAGTATGAAAGCAGAAGAGATTACA
CCTGGTAGATATAGAACAGCAATTTGTGGACTTTACCCTGCACAAATTAA
GGCAAGACAGATGATTAGTCCAGTCATGAGTGTAATCGGATTCTTGGCTT
TGGCAAAAGATTGGAGTGACCGCATTGAGCAGTGGTTAAGTGAACCGTGT
AAGCTTCTTCCAGATACAGCAGCAGTTAGCCTTCTTGGTGGTCCTGCAAC
CAACAGGGACTATTTACGGCAGCGACAAGTAGCATTGGGCAACATGGAAA
CAAAAGAGTCTAAGGCTATACGCCAACATGCAGAAGCAGCAGGCTGTAGT
ATGATTGAGGACATTGAGTCACCATCATCAATATGGGTGTTTGCTGGGGC
ACCGGACCGCTGTCCACCAACATGTCTCTTTATTGCAGGTATGGCTGAGC
TTGGGGCATTTTTTTCCATCCTGCAGGACATGCGAAATACAATTATGGCA
TCCAAGACAGTTGGAACCTCTGAGGAGAAGCTACGGAAGAAATCCTCATT
CTATCAGTCTTATCTCAGGAGAACACAATCAATGGGAATACAACTGGATC

-continued

AGAGGATAATTGTGCTCTTCATGGTAGCCTGGGGGAAAGAAGCAGTGGAT
AACTTCCACCTAGGAGATGATATGGACCCTGAGCTGCGAACACTAGCACA
GAGCCTGATTGATGTTAAAGTGAAGGAAATTTCCAACCAAGAGCCTTTAA
AACTA

The inventors have generated a nucleic acid sequence encoding Hantavirus NP that is optimised for expression in *Homo sapiens* (see SEQ ID NO: 9):

(SEQ ID NO: 9)
ATGCTGAGCTACGGCAACGTGCTGGATCTGAACCACCTGGATATCGACGA
GCCAACAGGACAGACCGCTGATTGGCTGGGCATCGTGATCTACCTGACCT
CCTTTGTGGTGCCTATTCTGCTCAAAGCCCTCTATATGCTGACAACACGC
GGAAGGCAGACCACCAAAGATAACAAAGGCACCCGGATCAGGTTTAAGGA
CGACAGCTCCTTTGAGGATGTCAACGGCATCCGGAAACCTAAGCACCTCT
ATGTGTCTCTGCCCAATGCACAGTCCTCCATGAAGGCAGAAGAGATCACA
CCAGGCCGGTACAGAACCGCCATCTGTGGACTGTATCCTGCACAAATCAA
AGCCCGGCAGATGATCAGCCCCGTGATGTCCGTTATCGGATTCCTGGCTC
TGGCCAAAGATTGGAGCGACAGGATCGAGCAGTGGCTGAGCGAGCCTTGC
AAGCTGCTTCCTGATACAGCCGCTGTGTCACTGCTTGGCGGCCCTGCCAC
AAACAGAGATTACCTGAGACAGAGACAGGTGGCACTGGGCAACATGGAAA
CAAAAGAGAGCAAGGCCATCCGGCAGCATGCCGAAGCTGCTGGCTGTAGC
ATGATCGAGGATATCGAGTCCCCTAGCTCCATTTGGGTGTTCGCAGGGGC
CCCAGATAGATGTCCACCAACATGCCTGTTCATTGCCGGCATGGCTGAAC
TGGGAGCTTTTTTCAGCATCCTCCAGGATATGCGCAACACGATTATGGCC
TCCAAGACAGTGGGAACCAGCGAGGAAAAGCTGCGGAAGAAAAGCAGCTT
TTACCAGTCTTACCTGAGGCGGACCCAGTCCATGGGGATCCAACTGGATC
AGCGGATCATTGTGCTGTTTATGGTCGCTTGGGGAAAAGAGGCTGTCGAT
AACTTCCACCTGGGAGATGATATGGATCCTGAACTGCGGACCCTGGCTCA
GTCCCTGATCGATGTGAAAGTGAAAGAAATTAGTAATCAAGAACCCCTCA
AGCTG

Nucleic acid sequences comprising SEQ ID NO: 8 or 9 are particularly well-suited to use in vectors of the invention that also encode nucleoprotein from a Hantavirus strain other than Hantaan virus, such as nucleoprotein from Seoul virus. The inventors determined that the 94 N-terminal amino acids of the wild-type Hantaan virus nucleoprotein display high sequence similarity to the N-terminus of the wild-type nucleoprotein from Seoul virus, and where sequence differences exist within this region, the inventors determined that both sequences contain closely-related amino acids. The 95$^{th}$ residue of the wild-type Hantaan virus nucleoprotein sequence was identified as the first residue that is markedly different from the corresponding residue in the wild-type nucleoprotein sequence from Seoul virus. The inventors believe that nucleic acids encoding the 94 N-terminal amino acids of the Hantaan virus wild-type nucleoprotein are substantially antigenically redundant when present in a vector that also encodes nucleoprotein from Seoul virus (or at least the 94 N-terminal amino acids of the wild-type nucleoprotein from Seoul virus, or an antigenic fragment thereof). Thus, the inventors believe that nucleic acids encoding the 94 N-terminal amino acids of the wild-type Hantaan virus nucleoprotein may be omitted from vectors that also encode nucleoprotein from Seoul virus (or at least the 94 N-terminal amino acids of the wild-type nucleoprotein from Seoul virus, or an antigenic fragment thereof), without sacrificing antigenic diversity. Removal of unnecessary nucleic acid sequences is generally advantageous in the design of vector constructs (e.g. MVA constructs) because it can enhance vector stability.

For the reasons set out above, the inventors believe that similar advantages may be achieved when nucleic acids encoding the 94 N-terminal amino acids of the Seoul virus nucleoprotein are omitted, particularly from vectors that encode the Hantaan virus nucleoprotein (or at least the 94 N-terminal amino acids of the wild-type nucleoprotein from Hantaan virus, or an antigenic fragment thereof).

Translation of the nucleic acid sequence of SEQ ID NO: 8 or SEQ ID NO: 9 yields a Hantavirus NP polypeptide sequence, which is represented by (SEQ ID NO: 10):

(SEQ ID NO: 10)
```
MLSYGNVLDLNHLDIDEPTGQTADWLGIVIYLTSFVVPILLKALYMLTTR
GRQTTKDNKGTRIRFKDDSSFEDVNGIRKPKHLYVSLPNAQSSMKAEEIT
PGRYRTAICGLYPAQIKARQMISPVMSVIGFLALAKDWSDRIEQWLSEPC
KLLPDTAAVSLLGGPATNRDYLRQRQVALGNMETKESKAIRQHAEAAGCS
MIEDIESPSSIWVFAGAPDRCPPTCLFIAGMAELGAFFSILQDMRNTIMA
SKTVGTSEEKLRKKSSFYQSYLRRTQSMGIQLDQRIIVLFMVAWGKEAVD
NFHLGDDMDPELRTLAQSLIDVKVKEISNQEPLKL
```

As used herein, the term "antigenic fragment" means a peptide or protein fragment of a Hantavirus NP which retains the ability to induce an immune response in an individual, as compared to the reference Hantavirus NP. An antigenic fragment may therefore include at least one epitope of the reference protein. By way of example, an antigenic fragment of the present invention may comprise (or consist of) a peptide sequence having at least 5, 10, 15, 20, 25, 30, 35, 40, 45, 50, 60, 70, 80, 90, 100, 125, 150, 175, 200, 225, 250, 275, 300 amino acids, wherein the peptide sequence has at least 70% sequence homology over a corresponding peptide sequence of (contiguous) amino acids of the reference protein. An antigenic fragment may comprise (or consist of) at least 10 consecutive amino acid residues from the sequence of the reference protein (for example, at least 5, 10, 15, 20, 25, 30, 35, 40, 45, 50, 60, 70, 80, 90, 100, 125, 150, 175, 200, 225, 250, 275 or 300 consecutive amino acid residues of said reference protein).

An antigenic fragment of a reference protein may have a common antigenic cross-reactivity and/or substantially the same in vivo biological activity as the reference protein. For example, an antibody capable of binding to an antigenic fragment of a reference protein would also be capable of binding to the reference protein itself. By way of further example, the reference protein and the antigenic fragment thereof may share a common ability to induce a "recall response" of a T lymphocyte (e.g. CD4+, CD8+, effector T cell or memory T cell such as a TEM or TCM), which has been previously exposed to an antigenic component of a Hantavirus infection.

In one aspect, the invention provides a viral vector or bacterial vector, said vector comprising a nucleic acid sequence encoding a Hantavirus nucleoprotein or antigenic fragment thereof, wherein said vector is capable of inducing an immune response in a subject.

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2 and 3.

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NO: 3.

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 5, 6, 8 and 9.

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NO: 9.

"Peptide pool 4" induced a very strong antigen-specific T-cell response (see Examples). The amino acid sequence represented by peptide pool 4 corresponds to SEQ ID NO: 11.

(SEQ ID NO: 11)
```
LYPAQIKARNMVSPVMSVVGFLALAKDWTSRIEEWLGAPCKFMAESPIAG
SLSGNPVNRDYIRQRQGALAGMEPKEFQA
```

The amino acid sequence of SEQ ID NO 11 is encoded by nucleic acid residues 655-891 of SEQ ID NO: 1 (see SEQ ID NO: 15); by residues 613-849 of SEQ ID NO: 2 (see SEQ ID NO: 16); and by residues 613-849 of SEQ ID NO: 3 (see SEQ ID NO: 17).

(SEQ ID NO: 15)
```
CTATACCCTGCACAGATAAAGGCAAGGAACATGGTAAGCCCTGTCATGAG
TGTAGTTGGGTTTTTGGCACTGGCAAAAGACTGGACATCTAGAATTGAAG
AATGGCTTGGTGCACCCTGCAAGTTCATGGCAGAGTCTCCCATTGCCGGG
AGCTTATCTGGGAATCCTGTGAATCGTGATTATATCAGACAGAGACAAGG
TGCACTTGCAGGGATGGAGCCAAAAGAATTTCAAGCT
```

(SEQ ID NO: 16)
```
CTATACCCTGCACAGATAAAGGCAAGGAACATGGTAAGCCCTGTCATGAG
TGTAGTTGGGTTTTTGGCACTGGCAAAAGACTGGACATCTAGAATTGAAG
AATGGCTTGGTGCACCCTGCAAGTTCATGGCAGAGTCTCCCATTGCCGGG
AGCTTATCTGGGAATCCTGTGAATCGTGATTATATCAGACAGAGACAAGG
TGCACTTGCAGGGATGGAGCCAAAAGAATTTCAAGCT
```

(SEQ ID NO: 17)
```
CTGTACCCCGCTCAGATCAAGGCCAGAAACATGGTGTCCCCAGTGATGAG
CGTCGTGGGATTTCTGGCCCTGGCTAAGGACTGGACCAGCAGGATTGAGG
```

-continued

AATGGCTGGGAGCCCCTTGCAAGTTTATGGCCGAGTCTCCTATCGCCGGC

AGCCTGTCTGGCAACCCCGTGAATAGAGACTACATCAGACAGAGGCAGGG

CGCTCTGGCCGGAATGGAACCCAAAGAATTTCAGGCC

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NOs: 15, 16 or 17.

In one embodiment, the nucleic acid sequence encoding a Hantavirus nucleoprotein or antigenic fragment thereof comprises (or consists of) at least 10 consecutive nucleic acid residues from the sequence of SEQ ID NOs: 15, 16 or 17 (for example, at least 10, 11, 12, 13, 14, 15, 20, 25, 30, 35, 40, 45, 50, 55, 60 or 65 nucleic acids of SEQ ID NOs: 15, 16 or 17).

"Peptide pool 9" also induced a very strong antigen-specific T-cell response. The amino acid sequence represented by peptide pool 9 corresponds to SEQ ID NO: 12.

(SEQ ID NO: 12)

IKARQMISPVMSVIGFLALAKDWSDRIEQWLSEPCKLLPDTAAVSLLGGP

ATNRDYLRQRQVALGNMETKESKAIRQHA

The amino acid sequence of SEQ ID NO 12 is encoded by nucleic acid residues 664-900 of SEQ ID NO: 5 (see SEQ ID NO: 18); by residues 628-864 of SEQ ID NO: 6 (see SEQ ID NO: 19); by residues 346-582 of SEQ ID NO: 8 (see SEQ ID NO: 20); and by residues 346-582 of SEQ ID NO: 9 (see SEQ ID NO: 21).

(SEQ ID NO: 18)

ATTAAGGCAAGACAGATGATTAGTCCAGTCATGAGTGTAATCGGATTCTT

GGCTTTGGCAAAAGATTGGAGTGACCGCATTGAGCAGTGGTTAAGTGAAC

CGTGTAAGCTTCTTCCAGATACAGCAGCAGTTAGCCTTCTTGGTGGTCCT

GCAACCAACAGGGACTATTTACGGCAGCGACAAGTAGCATTGGGCAACAT

GGAAACAAAAGAGTCTAAGGCTATACGCCAACATGCA (SEQ ID NO: 19)

ATTAAGGCAAGACAGATGATTAGTCCAGTCATGAGTGTAATCGGATTCTT

GGCTTTGGCAAAAGATTGGAGTGACCGCATTGAGCAGTGGTTAAGTGAAC

CGTGTAAGCTTCTTCCAGATACAGCAGCAGTTAGCCTTCTTGGTGGTCCT

GCAACCAACAGGGACTATTTACGGCAGCGACAAGTAGCATTGGGCAACAT

GGAAACAAAAGAGTCTAAGGCTATACGCCAACATGCA (SEQ ID NO: 20)

ATTAAGGCAAGACAGATGATTAGTCCAGTCATGAGTGTAATCGGATTCTT

GGCTTTGGCAAAAGATTGGAGTGACCGCATTGAGCAGTGGTTAAGTGAAC

CGTGTAAGCTTCTTCCAGATACAGCAGCAGTTAGCCTTCTTGGTGGTCCT

GCAACCAACAGGGACTATTTACGGCAGCGACAAGTAGCATTGGGCAACAT

GGAAACAAAAGAGTCTAAGGCTATACGCCAACATGCA (SEQ ID NO: 21)

ATCAAAGCCCGGCAGATGATCAGCCCCGTGATGTCCGTTATCGGATTCCT

GGCTCTGGCCAAAGATTGGAGCGACAGGATCGAGCAGTGGCTGAGCGAGC

-continued

CTTGCAAGCTGCTTCCTGATACAGCCGCTGTGTCACTGCTTGGCGGCCCT

GCCACAAACAGAGATTACCTGAGACAGAGACAGGTGGCACTGGGCAACAT

GGAAACAAAAGAGAGCAAGGCCATCCGGCAGCATGCC

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NOs: 18, 19, 20 or 21.

In one embodiment, the nucleic acid sequence encoding a Hantavirus nucleoprotein or antigenic fragment thereof comprises (or consists of) at least 10 consecutive nucleic acid residues from the sequence of SEQ ID NOs: 18, 19, 20 or 21 (for example, at least 10, 11, 12, 13, 14, 15, 20, 25, 30, 35, 40, 45, 50, 55, 60 or 65 nucleic acids of SEQ ID NOs: 18, 19, 20 or 21).

As demonstrated herein, peptide pools 4 and 9 induced a very strong antigen-specific T-cell response. By aligning the polypeptide sequence represented by "peptide pool 4" with the polypeptide sequence represented by "peptide pool 9", the inventors identified a region of high sequence identity, as represented by SEQ ID NO: 13 and SEQ ID NO: 14, respectively. Without wishing to be bound by theory, the inventors believe that the amino acid sequences of SEQ ID NOs: 13 and 14 play an important role in eliciting the particularly strong antigen-specific T-cell response observed with peptide pools 4 and 9, respectively.

(SEQ ID NO: 13)

SPVMSVVGFLALAKD (SEQ ID NO: 14)

PVMSVIGFLALAKDW

SEQ ID NO: 13 is encoded inter alia by nucleic acid residues 691-735 of SEQ ID NO: 1 (see SEQ ID NO: 22); by residues 649-693 of SEQ ID NO: 2 (see SEQ ID NO: 23); and by residues 649-693 of SEQ ID NO: 3 (see SEQ ID NO: 24).

(SEQ ID NO: 22)

AGCCCTGTCATGAGTGTAGTTGGGTTTTTGGCACTGGCAAAAGAC (SEQ ID NO: 23)

AGCCCTGTCATGAGTGTAGTTGGGTTTTTGGCACTGGCAAAAGAC (SEQ ID NO: 24)

TCCCCAGTGATGAGCGTCGTGGGATTTCTGGCCCTGGCTAAGGAC

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NOs: 22, 23 or 24.

SEQ ID NO: 14 is encoded inter alia by nucleic acid residues 688-732 of SEQ ID NO: 5 (see SEQ ID NO: 25); by residues 652-696 of SEQ ID NO: 6 (see SEQ ID NO: 26); by residues 370-414 of SEQ ID NO: 8 (see SEQ ID NO: 27); and by residues 370-414 of SEQ ID NO: 9 (see SEQ ID NO: 28).

(SEQ ID NO: 25)
CCAGTCATGAGTGTAATCGGATTCTTGGCTTTGGCAAAAGATTGG (SEQ ID NO: 26)
CCAGTCATGAGTGTAATCGGATTCTTGGCTTTGGCAAAAGATTGG (SEQ ID NO: 27)
CCAGTCATGAGTGTAATCGGATTCTTGGCTTTGGCAAAAGATTGG (SEQ ID NO: 28)
CCCGTGATGTCCGTTATCGGATTCCTGGCTCTGGCCAAAGATTGG

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NOs: 25, 26, 27 or 28.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence is provided by a nucleic acid sequence having at least 70% (such as at least 70, 75, 80, 82, 84, 86, 88, 90, 92, 94, 95, 96, 97, 98, 99 or 100%) sequence identity to SEQ ID NOs: 1, 2 or 3; and (B) the second nucleic acid sequence is provided by a nucleic acid sequence having at least 70% (such as at least 70, 75, 80, 82, 84, 86, 88, 90, 92, 94, 95, 96, 97, 98, 99 or 100%) sequence identity to SEQ ID NOs: 5, 6, 8 or 9.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence is provided by a nucleic acid sequence having at least 70% (such as at least 70, 75, 80, 82, 84, 86, 88, 90, 92, 94, 95, 96, 97, 98, 99 or 100%) sequence identity to SEQ ID NOs: 15, 16, 17, 22, 23 or 24; and (B) the second nucleic acid sequence is provided by a nucleic acid sequence having at least 70% (such as at least 70, 75, 80, 82, 84, 86, 88, 90, 92, 94, 95, 96, 97, 98, 99 or 100%) sequence identity to SEQ ID NOs: 18, 19, 20, 21, 25, 26, 27 or 28.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to a nucleic acid sequence selected from SEQ ID NOs: 15, 16, 17, 22, 23 or 24; and (B) the second nucleic acid sequence has at least 70% sequence identity to a nucleic acid sequence selected from SEQ ID NOs: 18, 19, 20, 21, 25, 26, 27 or 28.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to the nucleic acid sequence of SEQ ID NO: 24; and (B) the second nucleic acid sequence has at least 70% sequence identity to the nucleic acid sequence of SEQ ID NO: 28.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to a nucleic acid sequence selected from SEQ ID NOs: 22 or 23; and (B) the second nucleic acid sequence is provided by a nucleic acid sequence has at least 70% sequence identity to a nucleic acid sequence selected from SEQ ID NOs: 25, 26 or 27.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to the nucleic acid sequence of SEQ ID NO: 17; and (B) the second nucleic acid sequence has at least 70% sequence identity to the nucleic acid sequence of SEQ ID NO: 21.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to a nucleic acid sequence selected from SEQ ID NOs: 15 or 16; and (B) the second nucleic acid sequence has at least 70% sequence identity to a nucleic acid sequence selected from SEQ ID NOs: 18, 19 or 20.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to a nucleic acid sequence selected from SEQ ID NOs: 1, 2 or 3; and (B) the second nucleic acid sequence has at least 70% sequence identity to a nucleic acid sequence selected from SEQ ID NOs: 5, 6, 8 or 9.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to the nucleic acid sequence of SEQ ID NO: 3; and (B) the second nucleic acid sequence has at least 70% sequence identity to the nucleic acid sequence of SEQ ID NO: 9.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to the nucleic acid sequence of SEQ ID NO: 2; and (B) the second nucleic acid sequence has at least 70% sequence identity to the nucleic acid sequence of SEQ ID NO: 8.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid has at least 70% sequence identity to the nucleic acid sequence of SEQ ID NO: 2; and (B) the second nucleic acid sequence has at least 70% sequence identity to the nucleic acid sequence of SEQ ID NO: 6.

In one embodiment, the nucleic acid sequence encoding a Hantavirus nucleoprotein or antigenic fragment thereof comprises a first nucleic acid sequence and a second nucleic acid sequence, wherein:

(A) the first nucleic acid sequence has at least 70% sequence identity to the nucleic acid sequence of SEQ ID NO: 1; and (B) the second nucleic acid sequence has at least 70% sequence identity to the nucleic acid sequence of SEQ ID NO: 5.

In one embodiment, the first nucleic acid sequence is located 5' of the second nucleic acid sequence. In one embodiment, the second nucleic acid sequence is located 5' of the first nucleic acid sequence.

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to SEQ ID NO: 29.

```
                                        (SEQ ID NO: 29)
ATGGCCACAATGGAAGAGATCCAGAGAGAGATCAGCGCCCACGAG
GGACAGCTGGTTATCGCCAGACAGAAAGTGAAGGACGCCGAGAAG
CAGTACGAGAAGGACCCCGACGATCTGAACAAGAGAGCCCTGCAC
GACAGAGAAAGCGTGGCCGCCTCTATCCAGAGCAAGATCGATGAG
CTGAAGAGACAGCTGGCCGACAGAATCGCCGCTGGCAAGAATATT
GGCCAGGACAGAGATCCCACAGGCGTGGAACCTGGCGATCACCTG
AAAGAGAGAAGCGCCCTGTCCTATGGCAACACCCTGGACCTGAAC
AGCCTGGACATTGATGAGCCTACCGGCCAGACAGCCGACTGGCTG
ACAATCATTGTGTACCTGACCAGCTTCGTGGTCCCCATCATCCTG
AAGGCCCTGTACATGCTGACCACCAGAGGCAGACAGACCAGCAAG
GACAACAAGGGCATGAGAATCCGGTTCAAGGATGACAGCAGCTAC
GAGGACGTGAACGGCATTAGAAAGCCCAAGCACCTGTACGTGTCC
ATGCCTAACGCTCAGAGCAGCATGAAGGCCGAGGAAATCACCCCT
GGCAGATTCAGAACAGCCGTGTGCGGACTGTACCCCGCTCAGATC
AAGGCCAGAAACATGGTGTCCCCAGTGATGAGCGTCGTGGGATTT
CTGGCCCTGGCTAAGGACTGGACCAGCAGGATTGAGGAATGGCTG
GGAGCCCCTTGCAAGTTTATGGCCGAGTCTCCTATCGCCGGCAGC
CTGTCTGGCAACCCCGTGAATAGAGACTACATCAGACAGAGGCAG
GGCGCTCTGGCCGGAATGGAACCCAAAGAATTTCAGGCCCTGCGG
CAGCACTCTAAGGATGCCGGATGTACCCTGGTGGAACACATTGAG
AGCCCCAGCAGCATCTGGGTTTTCGCTGGCGCTCCTGATAGATGC
CCTCCTACCTGTCTGTTTGTTGGCGGAATGGCCGAGCTGGGCGCC
TTCTTTAGCATTCTGCAGGACATGCGGAATACCATCATGGCCAGC
AAGACCGTGGGCACCGCCGATGAGAAGCTGAGAAAGAAGTCCAGC
TTCTACCAGAGCTACCTGCGGAGAACCCAGAGCATGGGCATTCAG
CTGGACCAGAGAATCATCGTGATGTTCATGGTGGCCTGGGGCAAA
GAAGCCGTGGACAATTTTCACCTGGGCGACGACATGGACCCCGAG
CTGAGATCTCTGGCCCAGATCCTGATCGACCAGAAAGTCAAAGAG
```

-continued

```
ATCTCCAATCAAGAGCCCATGAAGCTGATGCTGAGCTACGGCAAC
GTGCTGGATCTGAACCACCTGGATATCGACGAGCCAACAGGACAG
ACCGCTGATTGGCTGGGCATCGTGATCTACCTGACCTCCTTTGTG
GTGCCTATTCTGCTCAAAGCCCTCTATATGCTGACAACACGCGGA
AGGCAGACCACCAAAGATAACAAAGGCACCCGGATCAGGTTTAAG
GACGACAGCTCCTTTGAGGATGTCAACGGCATCCGGAAACCTAAG
CACCTCTATGTGTCTCTGCCCAATGCACAGTCCTCCATGAAGGCA
GAAGAGATCACACCAGGCCGGTACAGAACCGCCATCTGTGGACTG
TATCCTGCACAAATCAAAGCCCGGCAGATGATCAGCCCCGTGATG
TCCGTTATCGGATTCCTGGCTCTGGCCAAAGATTGGAGCGACAGG
ATCGAGCAGTGGCTGAGCGAGCCTTGCAAGCTGCTTCCTGATACA
GCCGCTGTGTCACTGCTTGGCGGCCCTGCCACAAACAGAGATTAC
CTGAGACAGAGACAGGTGGCACTGGGCAACATGGAAACAAAAGAG
AGCAAGGCCATCCGGCAGCATGCCGAAGCTGCTGGCTGTAGCATG
ATCGAGGATATCGAGTCCCCTAGCTCCATTTGGGTGTTCGCAGGG
GCCCCAGATAGATGTCCACCAACATGCCTGTTCATTGCCGGCATG
GCTGAACTGGGAGCTTTTTTCAGCATCCTCCAGGATATGCGCAAC
ACGATTATGGCCTCCAAGACAGTGGGAACCAGCGAGGAAAAGCTG
CGGAAGAAAAGCAGCTTTTACCAGTCTTACCTGAGGCGGACCCAG
TCCATGGGGATCCAACTGGATCAGCGGATCATTGTGCTGTTTATG
GTCGCTTGGGGAAAAGAGGCTGTCGATAACTTCCACCTGGGAGAT
GATATGGATCCTGAACTGCGGACCCTGGCTCAGTCCCTGATCGAT
GTGAAAGTGAAAGAAATTAGTAATCAAGAACCCCTCAAGCTG
```

In one embodiment, the nucleic acid sequence encoding a Hantavirus nucleoprotein or antigenic fragment thereof comprises a nucleic acid sequence having at least 70% (such as at least 70, 75, 80, 82, 84, 86, 88, 90, 92, 94, 95, 96, 97, 98, 99 or 100%) sequence identity to SEQ ID NO: 30.

```
                                        (SEQ ID NO: 30)
ATGCTGAGCTACGGCAACGTGCTGGATCTGAACCACCTGGATATC
GACGAGCCAACAGGACAGACCGCTGATTGGCTGGGCATCGTGATC
TACCTGACCTCCTTTGTGGTGCCTATTCTGCTCAAAGCCCTCTAT
ATGCTGACAACACGCGGAAGGCAGACCACCAAAGATAACAAAGGC
ACCCGGATCAGGTTTAAGGACGACAGCTCCTTTGAGGATGTCAAC
GGCATCCGGAAACCTAAGCACCTCTATGTGTCTCTGCCCAATGCA
CAGTCCTCCATGAAGGCAGAAGAGATCACACCAGGCCGGTACAGA
ACCGCCATCTGTGGACTGTATCCTGCACAAATCAAAGCCCGGCAG
ATGATCAGCCCCGTGATGTCCGTTATCGGATTCCTGGCTCTGGCC
AAAGATTGGAGCGACAGGATCGAGCAGTGGCTGAGCGAGCCTTGC
AAGCTGCTTCCTGATACAGCCGCTGTGTCACTGCTTGGCGGCCCT
GCCACAAACAGAGATTACCTGAGACAGAGACAGGTGGCACTGGGC
```

-continued

AACATGGAAACAAAAGAGAGCAAGGCCATCCGGCAGCATGCCGAA

GCTGCTGGCTGTAGCATGATCGAGGATATCGAGTCCCCTAGCTCC

ATTTGGGTGTTCGCAGGGGCCCCAGATAGATGTCCACCAACATGC

CTGTTCATTGCCGGCATGGCTGAACTGGGAGCTTTTTTCAGCATC

CTCCAGGATATGCGCAACACGATTATGGCCTCCAAGACAGTGGGA

ACCAGCGAGGAAAAGCTGCGGAAGAAAAGCAGCTTTTACCAGTCT

TACCTGAGGCGGACCCAGTCCATGGGGATCCAACTGGATCAGCGG

ATCATTGTGCTGTTTATGGTCGCTTGGGGAAAAGAGGCTGTCGAT

AACTTCCACCTGGGAGATGATATGGATCCTGAACTGCGGACCCTG

GCTCAGTCCCTGATCGATGTGAAAGTGAAAGAAATTAGTAATCAA

GAACCCCTCAAGCTGATGGCCACAATGGAAGAGATCCAGAGAGAG

ATCAGCGCCCACGAGGGACAGCTGGTTATCGCCAGACAGAAAGTG

AAGGACGCCGAGAAGCAGTACGAGAAGGACCCCGACGATCTGAAC

AAGAGAGCCCTGCACGACAGAGAAAGCGTGGCCGCCTCTATCCAG

AGCAAGATCGATGAGCTGAAGAGACAGCTGGCCGACAGAATCGCC

GCTGGCAAGAATATTGGCCAGGACAGAGATCCCACAGGCGTGGAA

CCTGGCGATCACCTGAAAGAGAGAAGCGCCCTGTCCTATGGCAAC

ACCCTGGACCTGAACAGCCTGGACATTGATGAGCCTACCGGCCAG

ACAGCCGACTGGCTGACAATCATTGTGTACCTGACCAGCTTCGTG

GTCCCCATCATCCTGAAGGCCCTGTACATGCTGACCACCAGAGGC

AGACAGACCAGCAAGGACAACAAGGGCATGAGAATCCGGTTCAAG

GATGACAGCAGCTACGAGGACGTGAACGGCATTAGAAAGCCCAAG

CACCTGTACGTGTCCATGCCTAACGCTCAGAGCAGCATGAAGGCC

GAGGAAATCACCCCTGGCAGATTCAGAACAGCCGTGTGCGGACTG

TACCCCGCTCAGATCAAGGCCAGAAACATGGTGTCCCCAGTGATG

AGCGTCGTGGGATTTCTGGCCCTGGCTAAGGACTGGACCAGCAGG

ATTGAGGAATGGCTGGGAGCCCCTTGCAAGTTTATGGCCGAGTCT

CCTATCGCCGGCAGCCTGTCTGGCAACCCCGTGAATAGAGACTAC

ATCAGACAGAGGCAGGGCGCTCTGGCCGGAATGGAACCCAAAGAA

TTTCAGGCCCTGCGGCAGCACTCTAAGGATGCCGGATGTACCCTG

GTGGAACACATTGAGAGCCCCAGCAGCATCTGGGTTTTCGCTGGC

GCTCCTGATAGATGCCCTCCTACCTGTCTGTTTGTTGGCGGAATG

GCCGAGCTGGGCGCCTTCTTTAGCATTCTGCAGGACATGCGGAAT

ACCATCATGGCCAGCAAGACCGTGGGCACCGCCGATGAGAAGCTG

AGAAAGAAGTCCAGCTTCTACCAGAGCTACCTGCGGAGAACCCAG

AGCATGGGCATTCAGCTGGACCAGAGAATCATCGTGATGTTCATG

GTGGCCTGGGGCAAAGAAGCCGTGGACAATTTTCACCTGGGCGAC

GACATGGACCCCGAGCTGAGATCTCTGGCCCAGATCCTGATCGAC

CAGAAAGTCAAAGAGATCTCCAATCAAGAGCCCATGAAGCTG

The present inventors have found that Hantavirus NP encoded by the nucleic acid sequences of the invention can be used to generate effective immune responses in individuals against Hantavirus. In particular, the inventors have found that a highly effective immune response against Hantavirus is obtained when Hantavirus NP is delivered to the subject using a bacterial vector or a viral vector, such as a non-replicating poxvirus vector or an adenovirus vector.

Vectors are tools which can be used as vectors for the delivery of genetic material into a target cell. By way of example, viral vectors serve as antigen delivery vehicles and also have the power to activate the innate immune system through binding cell surface molecules that recognise viral elements. A recombinant viral vector can be produced that carries nucleic acid encoding a given antigen. The viral vector can then be used to deliver the nucleic acid to a target cell, where the encoded antigen is produced and then presented to the immune system by the target cell's own molecular machinery. As "non-self", the produced antigen generates an adaptive immune response in the target subject. Advantageously, vectors of the invention have been demonstrated herein to provide a protective immune response.

Viral vectors suitable for use in the present invention include poxvirus vectors (such as non-replicating poxvirus vectors), adenovirus vectors, and influenza virus vectors.

In certain embodiments, a "viral vector" may be a virus-like particle (VLP). VLPs are lipid enveloped particles which contain viral proteins. Certain viral proteins have an inherent ability to self-assemble, and in this process bud out from cellular membranes as independent membrane-enveloped particles. VLPs are simple to purify and can, for example, be used to present viral antigens. VLPs are therefore suitable for use in immunogenic compositions, such as those described below. In certain embodiments, the viral vector is not a virus-like particle.

Bacterial vectors can also be used as antigen delivery vehicles. A recombinant bacterial vector can be produced that carries nucleic acid encoding a given antigen. The recombinant bacterial vector may express the antigen on its surface. Following administration to a subject, the bacterial vector colonises antigen-presenting cells (e.g. dendritic cells or macrophages).

An antigen-specific immune response is induced. The immune response may be a cellular (T cell) immune response, or may comprise both humoral (e.g. B cell) and cellular (T cell) immune responses. Examples of bacteria suitable for use as recombinant bacterial vectors include *Escherichia coli, Shigella, Salmonella* (e.g. *S. typhimurium*), and *Listeria* bacteria. In one embodiment, the vector of the invention is a bacterial vector, wherein the bacterium is a Gram-negative bacterium. In one embodiment, the vector of the invention is a bacterial vector selected from an *Escherichia coli* vector, a *Shigella* vector, a *Salmonella* vector and a *Listeria* vector.

Without wishing to be bound by any one particular theory, the inventors believe that antigen delivery using the vectors of the invention stimulates, amongst other responses, a T cell response in the subject. Thus, the inventors believe that one way in which the present invention provides for protection against Hantavirus infection is by stimulating T cell responses and the cell-mediated immunity system. In addition, humoral (antibody) based protection can also be achieved.

A viral vector of the invention may be a non-replicating viral vector.

As used herein, a non-replicating viral vector is a viral vector which lacks the ability to productively replicate following infection of a target cell. Thus, the ability of a non-replicating viral vector to produce copies of itself following infection of a target cell (such as a human target cell in an individual undergoing vaccination with a non-replicating viral vector) is highly reduced or absent. Such a viral vector may also be referred to as attenuated or replication-deficient. The cause can be loss/deletion of genes essential for replication in the target cell. Thus, a non-replicating viral vector cannot effectively produce copies of itself following infection of a target cell. Non-replicating viral vectors may therefore advantageously have an improved safety profile as compared to replication-competent viral vectors. A non-replicating viral vector may retain the ability to replicate in cells that are not target cells, allowing viral vector production. By way of example, a non-replicating viral vector (e.g. a non-replicating poxvirus vector) may lack the ability to productively replicate in a target cell such as a mammalian cell (e.g. a human cell), but retain the ability to replicate (and hence allow vector production) in an avian cell (e.g. a chick embryo fibroblast, or CEF, cell).

A viral vector of the invention may be a non-replicating poxvirus vector. Thus, in one embodiment, the viral vector encoding a Hantavirus NP or antigenic fragment thereof is a non-replicating poxvirus vector.

In one embodiment, the non-replicating poxvirus vector is selected from: a Modified Vaccinia virus Ankara (MVA) vector, a NYVAC vaccinia virus vector, a canarypox (ALVAC) vector, and a fowlpox (FPV) vector. MVA and NYVAC are both attenuated derivatives of vaccinia virus. Compared to vaccinia virus, MVA lacks approximately 26 of the approximately 200 open reading frames.

In one embodiment, the non-replicating poxvirus vector is a FPV vector.

In a preferred embodiment, the non-replicating poxvirus vector is an MVA vector.

A viral vector of the invention may be an adenovirus vector. Thus, in one embodiment, the viral vector encoding a Hantavirus NP or antigenic fragment thereof is an adenovirus vector.

In one embodiment, the adenovirus vector is a non-replicating adenovirus vector (wherein non-replicating is defined as above). Adenoviruses can be rendered non-replicating by deletion of the E1 or both the E1 and E3 gene regions. Alternatively, an adenovirus may be rendered non-replicating by alteration of the E1 or of the E1 and E3 gene regions such that said gene regions are rendered non-functional. For example, a non-replicating adenovirus may lack a functional E1 region or may lack functional E1 and E3 gene regions. In this way the adenoviruses are rendered replication incompetent in most mammalian cell lines and do not replicate in immunised mammals. Most preferably, both E1 and E3 gene region deletions are present in the adenovirus, thus allowing a greater size of transgene to be inserted. This is particularly important to allow larger antigens to be expressed, or when multiple antigens are to be expressed in a single vector, or when a large promoter sequence, such as the CMV promoter, is used. Deletion of the E3 as well as the E1 region is particularly favoured for recombinant Ad5 vectors. Optionally, the E4 region can also be engineered.

In one embodiment, the adenovirus vector is selected from: a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector, and an Ad5 vector.

A viral vector of the invention may be a measles virus vector. Thus, in one embodiment, the viral vector encoding a Hantavirus NP or antigenic fragment thereof is a measles virus vector.

In one embodiment, the expression cassette comprising the nucleic acid sequence encoding a Hantavirus NP (or antigenic fragment thereof) is less than 9 kb (such as less than 9.0, 8.5, 8.0, 7.5, 7.0, 6, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, the expression cassette comprising the nucleic acid sequence encoding a Hantavirus NP (or antigenic fragment thereof) is less than 8 kb (such as less than 8.0, 7.9, 7.8, 7.7, 7.6, 7.5, 7.4, 7.3, 7.2, 7.1, 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, the expression cassette comprising the nucleic acid sequence encoding a Hantavirus NP (or antigenic fragment thereof) is less than 7 kb (such as less than 7.0, 6.9, 6.8, 6.7, 6.6, 6.5, 6.4, 6.3, 6.2, 6.1, 6.0, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, the expression cassette comprising the nucleic acid sequence encoding a Hantavirus NP (or antigenic fragment thereof) is less than 6 kb (such as less than 6, 5.9, 5.8, 5.7, 5.6, 5.5, 5.4, 5.3, 5.2, 5.1, 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, the expression cassette comprising the nucleic acid sequence encoding a Hantavirus NP (or antigenic fragment thereof) is less than 5 kb (such as less than 5.0, 4.9, 4.8, 4.7, 4.6, 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, the expression cassette comprising the nucleic acid sequence encoding a Hantavirus NP (or antigenic fragment thereof) is less than 4.5 kb (such as less than 4.5, 4.4, 4.3, 4.2, 4.1, 4.0, 3.9, 3.8, 3.7, 3.6, 3.5, 3.4, 3.3, 3.2, 3.1, 3.0, 2.9, 2.8, 2.7, 2.6, 2.5, 2.4, 2.3, 2.2, 2.1, 2.0, 1.9, 1.8, 1.7, 1.6, 1.5, 1.4, 1.3, 1.2, 1.1, 1.0 kb).

In one embodiment, wherein the vector is a viral vector, the virus (i.e. viral vector) is not a pseudotyped virus. Thus, in one embodiment, the envelope of the viral vector does not comprise foreign glycoproteins (i.e. glycoproteins that are not native to said viral vector).

In one embodiment, wherein the vector is a non-replicating poxvirus vector (such as an MVA vector), the nucleic acid sequence encoding a Hantavirus NP or antigenic fragment thereof comprises a nucleic acid sequence encoding a Hantavirus glycoprotein.

In one embodiment, wherein the vector is a non-replicating poxvirus vector (such as an MVA vector), the nucleic acid sequence encoding a Hantavirus NP or antigenic fragment thereof comprises a nucleic acid sequence encoding an epitope of a Hantavirus glycoprotein (GP).

In one embodiment, wherein the vector is a non-replicating poxvirus vector (such as an MVA vector), the nucleic acid sequence encoding a Hantavirus NP or antigenic fragment thereof does not comprise a nucleic acid sequence encoding a Hantavirus glycoprotein (GP).

In one embodiment, wherein the vector is a non-replicating poxvirus vector (such as an MVA vector), the nucleic acid sequence encoding a Hantavirus NP or antigenic fragment thereof does not comprise a nucleic acid sequence encoding an epitope of a Hantavirus glycoprotein (GP).

In one embodiment, Hantavirus nucleoprotein or antigenic fragment thereof is the only Hantavirus nucleic acid sequence in the vector.

In one embodiment, wherein the vector is a non-replicating poxvirus vector, the vector is stable, expresses a Hantavirus NP product, and induces a protective immune response in a subject.

In one embodiment, wherein the vector is an adenovirus vector, the vector is stable, expresses a Hantavirus NP product, and induces a protective immune response in a subject.

The nucleic acid sequences as described above may comprise a nucleic acid sequence encoding a Hantavirus NP wherein said NP comprises a fusion protein. The fusion protein may comprise a Hantavirus NP polypeptide fused to one or more further polypeptides, for example an epitope tag, another antigen, or a protein that increases immunogenicity (e.g. a flagellin).

In one embodiment, the nucleic acid sequence encoding a Hantavirus NP (as described above) further encodes a Tissue Plasminogen Activator (tPA) signal sequence, and/or a V5 fusion protein sequence. In certain embodiments, the presence of a tPA signal sequence can provide for increased immunogenicity; the presence of a V5 fusion protein sequence can provide for identification of expressed protein by immunolabeling.

In one embodiment, the vector (as described above) further comprises a nucleic acid sequence encoding an adjuvant (for example, a cholera toxin, an *E. coli* lethal toxin, or a flagellin).

In one embodiment, the vector does not comprise a nucleic acid sequence encoding an adjuvant. In one embodiment, the vector does not comprise a nucleic acid sequence encoding Hsp70.

A bacterial vector of the invention may be generated by the use of any technique for manipulating and generating recombinant bacteria known in the art.

In another aspect, the invention provides a nucleic acid sequence encoding a viral vector, as described above. Thus, the nucleic acid sequence may encode a non-replicating poxvirus vector as described above. Alternatively, the nucleic acid sequence may encode an adenovirus vector as described above.

The nucleic acid sequence encoding a viral vector (as described above) may be generated by the use of any technique for manipulating and generating recombinant nucleic acid known in the art.

In one aspect, the invention provides a method of making a viral vector (as described above), comprising providing a nucleic acid, wherein the nucleic acid comprises a nucleic acid sequence encoding a vector (as described above); transfecting a host cell with the nucleic acid; culturing the host cell under conditions suitable for the propagation of the vector; and obtaining the vector from the host cell.

As used herein, "transfecting" may mean any non-viral method of introducing nucleic acid into a cell. The nucleic acid may be any nucleic acid suitable for transfecting a host cell. Thus, in one embodiment, the nucleic acid is a plasmid. The host cell may be any cell in which a vector (e.g. a non-replicating poxvirus vector or an adenovirus vector, as described above) may be grown. As used herein, "culturing the host cell under conditions suitable for the propagation of the vector" means using any cell culture conditions and techniques known in the art which are suitable for the chosen host cell, and which enable the vector to be produced in the host cell. As used herein, "obtaining the vector", means using any technique known in the art that is suitable for separating the vector from the host cell. Thus, the host cells may be lysed to release the vector. The vector may subsequently be isolated and purified using any suitable method or methods known in the art.

In one aspect, the invention provides a host cell comprising a nucleic acid sequence encoding a viral vector, as described above. The host cell may be any cell in which a viral vector (e.g. a non-replicating poxvirus vector or an adenovirus vector, as described above) may be grown or propagated. In one embodiment, the host cell is selected from: a 293 cell (also known as a HEK, or human embryonic kidney, cell), a CHO cell (Chinese Hamster Ovary), a CCL81.1 cell, a Vero cell, a HELA cell, a Per.C6 cell, a BHK cell (Baby Hamster Kidney), a primary CEF cell (Chick Embryo Fibroblast), a duck embryo fibroblast cell, a DF-1 cell, or a rat IEC-6 cell.

The present invention also provides compositions comprising vectors as described above.

In one aspect, the invention provides a composition comprising a vector (as described above) and a pharmaceutically-acceptable carrier.

Substances suitable for use as pharmaceutically-acceptable carriers are known in the art. Non-limiting examples of pharmaceutically-acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage. Examples of buffering agents include, but are not limited to, sodium succinate (pH 6.5), and phosphate buffered saline (PBS; pH 7.4).

In addition to a pharmaceutically-acceptable carrier, the composition of the invention can be further combined with one or more of a salt, excipient, diluent, adjuvant, immunoregulatory agent and/or antimicrobial compound.

Advantageously, vectors of the invention have been demonstrated to provide a protective immune response even without the use of an adjuvant. Thus, in one embodiment, the composition of the invention does not comprise an adjuvant.

The composition may be formulated as a neutral or salt form. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In one embodiment, the composition (as described above) further comprises at least one Hantavirus NP antigen (i.e. an antigen present in the composition in the form of a polypeptide). Thus, the composition may comprise both vector and polypeptide. In one embodiment, the polypeptide antigen is a Hantavirus NP. In one embodiment, the polypeptide antigen is a Hantavirus GP. In one embodiment, the presence of a polypeptide antigen means that, following administration of the composition to a subject, an improved simultaneous T cell and antibody response can be achieved. In one embodiment, the T cell and antibody response achieved surpasses that achieved when either a vector or a polypeptide antigen is used alone.

In one embodiment, the polypeptide antigen is not bonded to the vector. In one embodiment, the polypeptide antigen is a separate component to the vector. In one embodiment, the polypeptide antigen is provided separately from the vector.

In one embodiment, the polypeptide antigen is a variant of the antigen encoded by the vector. In one embodiment, the polypeptide antigen is a fragment of the antigen encoded by the vector. In one embodiment, the polypeptide antigen comprises at least part of a polypeptide sequence encoded by a nucleic acid sequence of the vector. Thus, the polypeptide antigen may correspond to at least part of the antigen encoded by the vector.

In one embodiment, the polypeptide antigen is a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 4, 7 and 10.

In one embodiment, the polypeptide antigen is a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 11 and 12.

In one embodiment, the polypeptide antigen is a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 13 and 14.

In one embodiment, the polypeptide antigen is a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 31 and 32.

```
                                          (SEQ ID NO: 31)
MATMEEIQREISAHEGQLVIARQKVKDAEKQYEKDPDDLNKRALH

DRESVAASIQSKIDELKRQLADRIAAGKNIGQDRDPTGVEPGDHL

KERSALSYGNTLDLNSLDIDEPTGQTADWLTIIVYLTSFVVPIIL

KALYMLTTRGRQTSKDNKGMRIRFKDDSSYEDVNGIRKPKHLYVS

MPNAQSSMKAEEITPGRFRTAVCGLYPAQIKARNMVSPVMSVVGF

LALAKDWTSRIEEWLGAPCKFMAESPIAGSLSGNPVNRDYIRQRQ

GALAGMEPKEFQALRQHSKDAGCTLVEHIESPSSIWVFAGAPDRC

PPTCLFVGGMAELGAFFSILQDMRNTIMASKTVGTADEKLRKKSS

FYQSYLRRTQSMGIQLDQRIIVMFMVAWGKEAVDNFHLGDDMDPE

LRSLAQILIDQKVKEISNQEPMKLMLSYGNVLDLNHLDIDEPTGQ

TADWLGIVIYLTSFVVPILLKALYMLTTRGRQTTKDNKGTRIRFK

DDSSEEDVNGIRKPKHLYVSLPNAQSSMKAEEITPGRYRTAICGL

YPAQIKARQMISPVMSVIGFLALAKDWSDRIEQWLSEPCKLLPDT

AAVSLLGGPATNRDYLRQRQVALGNMETKESKAIRQHAEAAGCSM

IEDIESPSSIWVFAGAPDRCPPTCLFIAGMAELGAFFSILQDMRN
```

-continued

```
TIMASKTVGTSEEKLRKKSSFYQSYLRRTQSMGIQLDQRIIVLFM

VAWGKEAVDNFHLGDDMDPELRTLAQSLIDVKVKEISNQEPLKL

                                          (SEQ ID NO: 32)
MLSYGNVLDLNHLDIDEPTGQTADWLGIVIYLTSFVVPILLKALY

MLTTRGRQTTKDNKGTRIRFKDDSSEEDVNGIRKPKHLYVSLPNA

QSSMKAEEITPGRYRTAICGLYPAQIKARQMISPVMSVIGFLALA

KDWSDRIEQWLSEPCKLLPDTAAVSLLGGPATNRDYLRQRQVALG

NMETKESKAIRQHAEAAGCSMIEDIESPSSIWVFAGAPDRCPPTC

LFIAGMAELGAFFSILQDMRNTIMASKTVGTSEEKLRKKSSFYQS

YLRRTQSMGIQLDQRIIVLEMVAWGKEAVDNEHLGDDMDPELRTL

AQSLIDVKVKEISNQEPLKLMATMEEIQREISAHEGQLVIARQKV

KDAEKQYEKDPDDLNKRALHDRESVAASIQSKIDELKRQLADRIA

AGKNIGQDRDPTGVEPGDHLKERSALSYGNTLDLNSLDIDEPTGQ

TADWLTIIVYLTSFVVPIILKALYMLTTRGRQTSKDNKGMRIRFK

DDSSYEDVNGIRKPKHLYVSMPNAQSSMKAEEITPGRFRTAVCGL

YPAQIKARNMVSPVMSVVGFLALAKDWTSRIEEWLGAPCKFMAES

PIAGSLSGNPVNRDYIRQRQGALAGMEPKEFQALRQHSKDAGCTL

VEHIESPSSIWVFAGAPDRCPPTCLFVGGMAELGAFFSILQDMRN

TIMASKTVGTADEKLRKKSSFYQSYLRRTQSMGIQLDQRIIVMFM

VAWGKEAVDNFHLGDDMDPELRSLAQILIDQKVKEISNQEPMKL
```

The polypeptide antigen may be the same as (or similar to) that encoded by a nucleic acid sequence of the vector of the composition. Thus, administration of the composition comprising a vector and a polypeptide antigen may be used to achieve an enhanced immune response against a single antigen, wherein said enhanced immune response comprises a combined T cell and an antibody response, as described above.

In one embodiment, a composition of the invention (as described above) further comprises at least one naked DNA (i.e. a DNA molecule that is separate from, and not part of, the viral vector of the invention) encoding a Hantavirus NP or antigenic fragment thereof. In one embodiment, the naked DNA comprises (or consists of) a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2, 3, 5, 6, 8, 9, and 15-30. In one embodiment, the naked DNA encodes a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 4, 7, 10-14, 31 and 32.

In one embodiment, a composition of the invention (as described above) further comprises an adjuvant. Non-limiting examples of adjuvants suitable for use with compositions of the present invention include aluminium phosphate, aluminium hydroxide, and related compounds; monophosphoryl lipid A, and related compounds; outer membrane vesicles from bacteria; oil-in-water emulsions such as MF59; liposomal adjuvants, such as virosomes, Freund's adjuvant and related mixtures; poly-lactid-co-glycolid acid (PLGA) particles; cholera toxin; *E. coli* lethal toxin; and flagellin.

The vectors and compositions of the invention (as described above) can be employed as vaccines. Thus, a composition of the invention may be a vaccine composition.

As used herein, a vaccine is a formulation that, when administered to an animal subject such as a mammal (e.g. a human, bovine, porcine, ovine, caprine, equine, cervine, canine or feline subject; in particular a human subject), stimulates a protective immune response against an infectious disease. The immune response may be a humoral and/or a cell-mediated immune response. Thus, the vaccine may stimulate B cells and/or T cells.

The term "vaccine" is herein used interchangeably with the terms "therapeutic/prophylactic composition", "immunogenic composition", "formulation", "antigenic composition", or "medicament".

In one aspect, the invention provides a vector (as described above) or a composition (as described above) for use in medicine.

In one aspect, the invention provides a vector (as described above) or a composition (as described above) for use in a method of inducing an immune response in a subject. The immune response may be against a Hantavirus antigen (e.g. a Hantavirus NP) and/or a Hantavirus infection. Thus, the vectors and compositions of the invention can be used to induce an immune response in a subject against a Hantavirus NP (for example, as immunogenic compositions or as vaccines).

In one embodiment, the immune response comprises a T cell response.

In one embodiment, the method of inducing an immune response in a subject comprises administering to a subject an effective amount of a vector (as described above) or a composition (as described above).

In one aspect, the invention provides a vector (as described above) or a composition (as described above) for use in a method of preventing or treating a Hantavirus infection in a subject.

In one embodiment, the invention provides a vector (as described above) or a composition (as described above) for use in a method of preventing or treating HFRS in a subject.

The vectors and compositions of the invention are ideally-suited to use in the prevention or treatment of HFRS, particularly when the Hantavirus nucleoprotein or antigenic fragment thereof is from Seoul virus. As noted above, Seoul virus is typically associated with causing HFRS.

The vectors and compositions of the invention are ideally-suited to use in the prevention or treatment of HFRS, particularly when the Hantavirus nucleoprotein or antigenic fragment thereof is from Hantaan virus. As noted above, Hantaan virus is typically associated with causing HFRS.

The vectors and compositions of the invention are ideally-suited to use in the prevention or treatment of HFRS, particularly when the Hantavirus nucleoprotein or antigenic fragment thereof is a chimeric sequence comprising a chimera of Seoul virus nucleoprotein (or antigenic fragment thereof) and Hantaan virus nucleoprotein (or antigenic fragment thereof), e.g. as demonstrated in the Examples.

As used herein, the term "preventing" includes preventing the initiation of Hantavirus infection and/or reducing the severity of intensity of a Hantavirus infection. Thus, "preventing" encompasses vaccination.

As used herein, the term "treating" embraces therapeutic and preventative/prophylactic measures (including post-exposure prophylaxis) and includes post-infection therapy and amelioration of a Hantavirus infection.

In one embodiment, the Hantavirus infection is Seoul virus infection. In one embodiment, the Hantavirus infection is Hantaan virus infection. In one embodiment, the Hantavirus infection is Seoul virus and/or Hantaan virus infection.

Each of the above-described methods can comprise the step of administering to a subject an effective amount, such as a therapeutically effective amount, of a vector or a composition of the invention.

In this regard, as used herein, an effective amount is a dosage or amount that is sufficient to achieve a desired biological outcome. As used herein, a therapeutically effective amount is an amount which is effective, upon single or multiple dose administration to a subject (such as a mammalian subject, in particular a human subject) for treating, preventing, suppressing curing, delaying, reducing the severity of, ameliorating at least one symptom of a disorder or recurring disorder, or prolonging the survival of the subject beyond that expected in the absence of such treatment.

Accordingly, the quantity of active ingredient to be administered depends on the subject to be treated, capacity of the subject's immune system to generate a protective immune response, and the degree of protection required. Precise amounts of active ingredient required to be administered may depend on the judgement of the practitioner and may be particular to each subject.

Administration to the subject can comprise administering to the subject a vector (as described above) or a composition (as described above) wherein the composition is sequentially administered multiple times (for example, wherein the composition is administered two, three or four times). Thus, in one embodiment, the subject is administered a vector (as described above) or a composition (as described above) and is then administered the same vector or composition (or a substantially similar vector or composition) again at a different time.

In one embodiment, administration to a subject comprises administering a vector (as described above) or a composition (as described above) to a subject, wherein said composition is administered substantially prior to, simultaneously with, or subsequent to, another immunogenic composition.

Prior, simultaneous and sequential administration regimes are discussed in more detail below.

In certain embodiments, the above-described methods further comprise the administration to the subject of a second vector, wherein the second vector comprises a nucleic acid sequence encoding a Hantavirus NP. Preferably, the second vector is a vector of the invention as described above (such as a viral vector, for example a non-replicating poxvirus vector or an adenovirus vector as described above).

In one embodiment, the first and second vectors are of the same vector type. In one embodiment, the first and second vectors are of different vector types. In one embodiment, the first vector is an adenovirus vector (as described above) and the second vector is a non-replicating poxvirus vector (as described above). In one embodiment, the first vector is a non-replicating poxvirus vector (as described above) and the second vector is an adenovirus vector (as described above).

In one embodiment, the first and second vectors are administered sequentially, in any order. Thus, the first ("1") and second ("2") vectors may be administered to a subject in the order 1-2, or in the order 2-1.

As used herein, "administered sequentially" has the meaning of "sequential administration", as defined below. Thus, the first and second vectors are administered at (substantially) different times, one after the other.

In one embodiment, the first and second vectors are administered as part of a prime-boost administration protocol. Thus, the first vector may be administered to a subject as the "prime" and the second vector subsequently administered to the same subject as the "boost". Prime-boost protocols are discussed below.

In one embodiment, each of the above-described methods further comprises the step of administration to the subject of a Hantavirus polypeptide antigen. In one embodiment, the Hantavirus polypeptide antigen is a Hantavirus NP (or antigenic fragment thereof) as described above. In one embodiment, the Hantavirus polypeptide antigen is a Hantavirus NP comprising an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 4, 7, 10-14, 31 and 32.

In one embodiment, the polypeptide antigen is administered separately from the administration of a vector; preferably the polypeptide antigen and a vector are administered sequentially. In one embodiment, the vector ("V") and the polypeptide antigen ("P") may be administered in the order V-P, or in the order P-V.

In one embodiment, each of the above-described methods further comprises the step of administration to the subject of a naked DNA encoding a Hantavirus NP or antigenic fragment thereof. In one embodiment, the naked DNA comprises (or consists of) a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2, 3, 5, 6, 8, 9, and 15-30. In one embodiment, the naked DNA encodes a Hantavirus NP comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 4, 7, 10-14, 31 and 32.

In one embodiment, the naked DNA is administered separately from the administration of a vector; preferably the naked DNA and a vector are administered sequentially. In one embodiment, the vector ("V") and the naked DNA ("D") may be administered in the order V-D, or in the order D-V.

In one embodiment, a naked DNA (as described above) is administered to a subject as part of a prime-boost protocol.

Heterologous prime-boosting approaches can improve immune responses, by allowing repeated vaccinations without increasing anti-vector immunity. A Hantavirus NP or an antigenic fragment thereof can be serially delivered via different vectors (as described above) or naked DNA vectors (as described above). In any heterologous prime-boost vaccination regime, NP-specific antibody response is increased, NP-specific T-cell response is increased, and/or clinical illness is reduced, as compared to use of a single vector. Suitable combinations of vectors include but are not limited to:

DNA prime, MVA boost
DNA prime, Fowlpox boost
Fowlpox prime, MVA boost
MVA prime, Fowlpox boost
DNA prime, Fowlpox boost, MVA boost
MVA prime, Adenovirus boost As used herein, the term polypeptide embraces peptides and proteins.

In certain embodiments, the above-described methods further comprise the administration to the subject of an adjuvant. Adjuvant may be administered with one, two, three, or all four of: a first vector, a second vector, a polypeptide antigen, and a naked DNA.

The immunogenic compositions, therapeutic formulations, medicaments, pharmaceutical compositions, and prophylactic formulations (e.g. vaccines) of the invention may be given in a single dose schedule (i.e. the full dose is given at substantially one time). Alternatively, the immunogenic compositions, therapeutic formulations, medicaments, pharmaceutical compositions, and prophylactic formulations (e.g. vaccines) of the invention may be given in a multiple dose schedule.

A multiple dose schedule is one in which a primary course of treatment (e.g. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (e.g. doctor or veterinarian).

Simultaneous administration means administration at (substantially) the same time.

Sequential administration of two or more compositions/therapeutic agents/vaccines means that the compositions/therapeutic agents/vaccines are administered at (substantially) different times, one after the other.

For example, sequential administration may encompass administration of two or more compositions/therapeutic agents/vaccines at different times, wherein the different times are separated by a number of days (for example, at least 1, 2, 5, 10, 15, 20, 30, 60, 90, 100, 150 or 200 days).

For example, in one embodiment, the vaccine of the present invention may be administered as part of a 'prime-boost' vaccination regime.

In one embodiment, the immunogenic compositions, therapeutic formulations, medicaments, pharmaceutical compositions, and prophylactic formulations (e.g. vaccines) of the invention can be administered to a subject such as a mammal (e.g. a human, bovine, porcine, ovine, caprine, equine, cervine, ursine, canine or feline subject) in conjunction with (simultaneously or sequentially) one or more immunoregulatory agents selected from, for example, immunoglobulins, antibiotics, interleukins (e.g. IL-2, IL-12), and/or cytokines (e.g. IFNγ).

The immunogenic compositions, therapeutic formulations, medicaments, pharmaceutical compositions, and prophylactic formulations (e.g. vaccines) may contain 5% to 95% of active ingredient, such as at least 10% or 25% of active ingredient, or at least 40% of active ingredient or at least 50, 55, 60, 70 or 75% active ingredient.

The immunogenic compositions, therapeutic formulations, medicaments, pharmaceutical compositions, and prophylactic formulations (e.g. vaccines) are administered in a manner compatible with the dosage formulation, and in such amount as will be prophylactically and/or therapeutically effective.

Administration of immunogenic compositions, therapeutic formulations, medicaments, pharmaceutical compositions, and prophylactic formulations (e.g. vaccines) is generally by conventional routes e.g. intravenous, subcutaneous, intraperitoneal, or mucosal routes. The administration may be by parenteral administration; for example, a subcutaneous or intramuscular injection.

Accordingly, immunogenic compositions, therapeutic formulations, medicaments, pharmaceutical compositions, and prophylactic formulations (e.g. vaccines) of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the immunogenic compositions, therapeutic formulations, medicaments, pharmaceutical compositions, and prophylactic formulations (e.g. vaccines) may contain minor amounts of auxiliary substances such as wetting or emulsifying agents, and/or pH buffering agents.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

It may be desired to direct the compositions of the present invention (as described above) to the respiratory system of a subject. Efficient transmission of a therapeutic/prophylactic composition or medicament to the site of infection in the lungs may be achieved by oral or intra-nasal administration.

Formulations for intranasal administration may be in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm.

Aerosol particles may be for delivery using a nebulizer (e.g. via the mouth) or nasal spray. An aerosol formulation may optionally contain a propellant and/or surfactant.

In one embodiment, the immunogenic compositions, therapeutic formulations, medicaments, pharmaceutical compositions, and prophylactic formulations (e.g. vaccines) of the invention comprise a pharmaceutically acceptable carrier, and optionally one or more of a salt, excipient, diluent and/or adjuvant.

In one embodiment, the immunogenic compositions, therapeutic formulations, medicaments, pharmaceutical compositions, and prophylactic formulations (e.g. vaccines) of the invention may comprise one or more immunoregulatory agents selected from, for example, immunoglobulins, antibiotics, interleukins (e.g. IL-2, IL-12), and/or cytokines (e.g. IFNγ).

The present invention encompasses polypeptides that are substantially homologous to polypeptides based on any one of the polypeptide antigens identified in this application (including fragments thereof). The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences. Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (e.g. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\frac{\text{Total number of identical matches}}{\left[\begin{array}{c}\text{length of the longer sequence plus the number of gaps} \\ \text{Introduced into the longer sequence in order} \\ \text{to align the two sequences}\end{array}\right]} \times 100$$

BLOSUM62 table

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | −1 | 5 | | | | | | | | | | | | | | | | | | |
| N | −2 | 0 | 6 | | | | | | | | | | | | | | | | | |
| D | −2 | −2 | 1 | 6 | | | | | | | | | | | | | | | | |
| C | 0 | −3 | −3 | −3 | 9 | | | | | | | | | | | | | | | |
| Q | −1 | 1 | 0 | 0 | −3 | 5 | | | | | | | | | | | | | | |

-continued

BLOSUM62 table

| | A | R | N | D | C | Q | E | G | H | I | L | K | M | F | P | S | T | W | Y | V |
|---|---|---|---|---|---|---|---|---|---|---|---|---|---|---|---|---|---|---|---|---|
| E | −1 | 0 | 0 | 2 | −4 | 2 | 5 | | | | | | | | | | | | | |
| G | 0 | −2 | 0 | −1 | −3 | −2 | −2 | 6 | | | | | | | | | | | | |
| H | −2 | 0 | 1 | −1 | −3 | 0 | 0 | −2 | 8 | | | | | | | | | | | |
| I | −1 | −3 | −3 | −3 | −1 | −3 | −3 | −4 | −3 | 4 | | | | | | | | | | |
| L | −1 | −2 | −3 | −4 | −1 | −2 | −3 | −4 | −3 | 2 | 4 | | | | | | | | | |
| K | −1 | 2 | 0 | −1 | −3 | 1 | 1 | −2 | −1 | −3 | −2 | 5 | | | | | | | | |
| M | −1 | −1 | −2 | −3 | −1 | 0 | −2 | −3 | −2 | 1 | 2 | −1 | 5 | | | | | | | |
| F | −2 | −3 | −3 | −3 | −2 | −3 | −3 | −3 | −1 | 0 | 0 | −3 | 0 | 6 | | | | | | |
| P | −1 | −2 | −2 | −1 | −3 | −1 | −1 | −2 | −2 | −3 | −3 | −1 | −2 | −4 | 7 | | | | | |
| S | 1 | −1 | 1 | 0 | −1 | 0 | 0 | 0 | −1 | −2 | −2 | 0 | −1 | −2 | −1 | 4 | | | | |
| T | 0 | −1 | 0 | −1 | −1 | −1 | −1 | −2 | −2 | −1 | −1 | −1 | −1 | −2 | −1 | 1 | 5 | | | |
| W | −3 | −3 | −4 | −4 | −2 | −2 | −3 | −2 | −2 | −3 | −2 | −3 | −1 | 1 | −4 | −3 | −2 | 11 | | |
| Y | −2 | −2 | −2 | −3 | −2 | −1 | −2 | −3 | 2 | −1 | −1 | −2 | −1 | 3 | −3 | −2 | −2 | 2 | 7 | |
| V | 0 | −3 | −3 | −3 | −1 | −2 | −2 | −3 | −3 | 3 | 1 | −2 | 1 | −1 | −2 | −2 | 0 | −3 | −1 | 4 |

In a homology comparison, the identity may exist over a region of the sequences that is at least 10 amino acid residues in length (e.g. at least 15, 20, 25, 30, 35, 40, 45, 50, 60, 70, 80, 90, 100, 125, 150, 175, 200, 225, 250, 275, 300, 325, 350, 375, 400, 425, 450, 475, 500, 525, 550 or 570 amino acid residues in length—e.g. up to the entire length of the reference sequence).

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

As used herein, the terms “nucleic acid sequence” and “polynucleotide” are used interchangeably and do not imply any length restriction. As used herein, the terms “nucleic acid” and “nucleotide” are used interchangeably. The terms “nucleic acid sequence” and “polynucleotide” embrace DNA (including cDNA) and RNA sequences.

The polynucleotide sequences of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, e.g. by the phosphoramidite method or the tri-ester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

When applied to a nucleic acid sequence, the term “isolated” in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC AGT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |

-continued

| Amino Acid | Codons | Degenerate Codon |
|---|---|---|
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/Asp | | RAY |
| Glu/Gln | | SAR |
| Any | | NNN |

One of ordinary skill in the art will appreciate that flexibility exists when determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82%, 84%, 86%, 88%, 90%, 92%, 94%, 96%, 98% or 99% of the nucleotide bases. Methods for homology determination of nucleic acid sequences are known in the art.

Alternatively, a "variant" nucleic acid sequence is substantially homologous with (or substantially identical to) a reference sequence (or a fragment thereof) if the "variant" and the reference sequence they are capable of hybridizing under stringent (e.g. highly stringent) hybridization conditions. Nucleic acid sequence hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

Methods of determining nucleic acid percentage sequence identity are known in the art. By way of example, when assessing nucleic acid sequence identity, a sequence having a defined number of contiguous nucleotides may be aligned with a nucleic acid sequence (having the same number of contiguous nucleotides) from the corresponding portion of a nucleic acid sequence of the present invention. Tools known in the art for determining nucleic acid percentage sequence identity include Nucleotide BLAST.

One of ordinary skill in the art appreciates that different species exhibit "preferential codon usage". As used herein, the term "preferential codon usage" refers to codons that are most frequently used in cells of a certain species, thus favouring one or a few representatives of the possible codons encoding each amino acid. For example, the amino acid threonine (Thr) may be encoded by ACA, ACC, ACG, or ACT, but in mammalian host cells ACC is the most commonly used codon; in other species, different Thr codons may be preferential. Preferential codons for a particular host cell species can be introduced into the polynucleotides of the present invention by a variety of methods known in the art. Introduction of preferential codon sequences into recombinant DNA can, for example, enhance production of the protein by making protein translation more efficient within a particular cell type or species.

Thus, in one embodiment of the invention, the nucleic acid sequence is codon optimized for expression in a host cell.

A "fragment" of a polynucleotide of interest comprises a series of consecutive nucleotides from the sequence of said full-length polynucleotide. By way of example, a "fragment" of a polynucleotide of interest may comprise (or consist of) at least 30 consecutive nucleotides from the sequence of said polynucleotide (e.g. at least 35, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, or 1710 consecutive nucleic acid residues of said polynucleotide). A fragment may include at least one antigenic determinant and/or may encode at least one antigenic epitope of the corresponding polypeptide of interest and/or may have a common antigenic cross-reactivity and/or substantially the same in vivo biological activity as the polypeptide of interest.

FIGURE LEGENDS

FIG. 1A-B. Example MVA vector construction. FIG. 1A provides a schematic representation of cassette "MVAHantaNP". FIG. 1B provides a schematic representation of plasmid 17ACNHBP_MVA-SEOV-HNT-NP_pMS-RQ (pMVAHantaNP).

Figure 2:
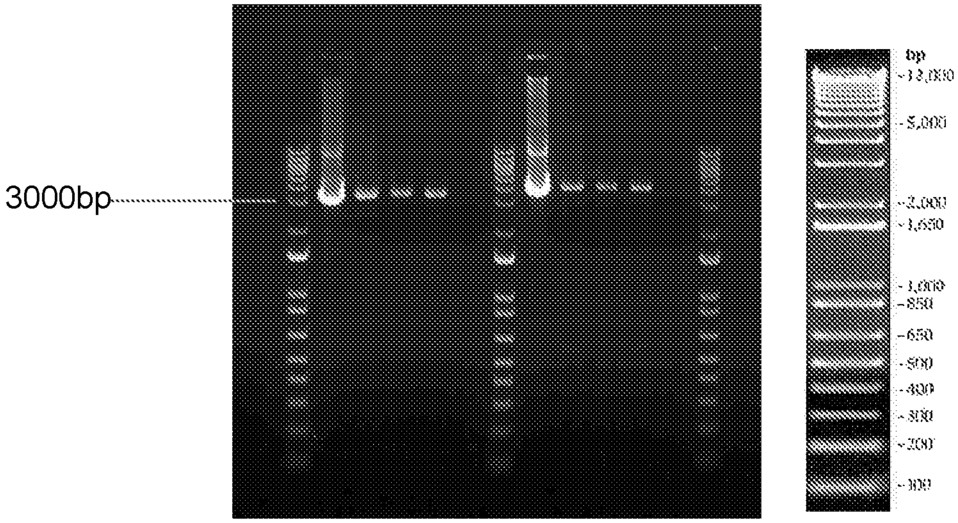

FIG. 2. PCR confirmation of pure recombinant Nucleoprotein-agarose gel confirming the presence of the MVAHantaNP construct. Flank to flank primers (SEQ ID NOs: 46 and 47) cover the entire insert and run from the MVA flanking regions at either end of the vaccine insert yielding an expected amplification product size. Contents of wells are as follows (numbered left to right): 1. Ladder; 2. Positive control (MVA-HantaNP plasmid) GFP to flank primers—expected size 3260 bp; 3. MVA-HantaNP "Batch 1"; 4. MVA-HantaNP "Batch 2+3"; 5. MVA-HantaNP "Batch 4+5+6"; 6. Negative control; 7. Ladder; 8. Positive control (MVA-HantaNP plasmid) flank to flank primers—expected size 3788 bp; 9. MVA-HantaNP "Batch 1"; 10. MVA- HantaNP "Batch 2+3"; 11. MVA-HantaNP "Batch 4+5+6"; 12. Negative control; 13. Ladder.

Figure 3:
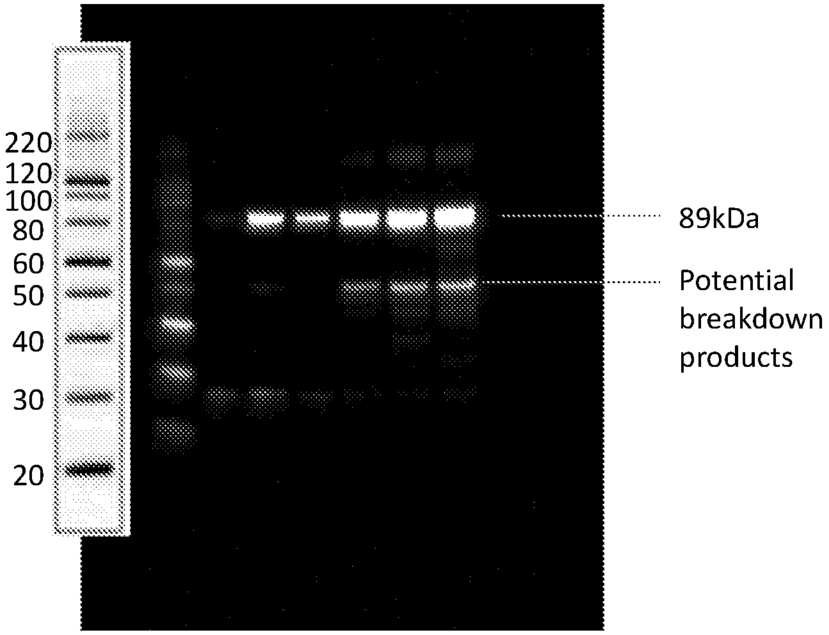

FIG. 3. Western blot confirming expression of the NP/Flag tag. The expected size of the protein is 89 kDa. Contents of wells are as follows (numbered left to right): 1. Ladder; 2. "Passage 3" P3 (1.1.1); 3. P3(4.1.1); 4.P3(4.1.2); 5. Vaccine Batch 1; 6. Vaccine batch 2+3 combined; 7. Vaccine batch 4+5+6 combined.

Figure 4:
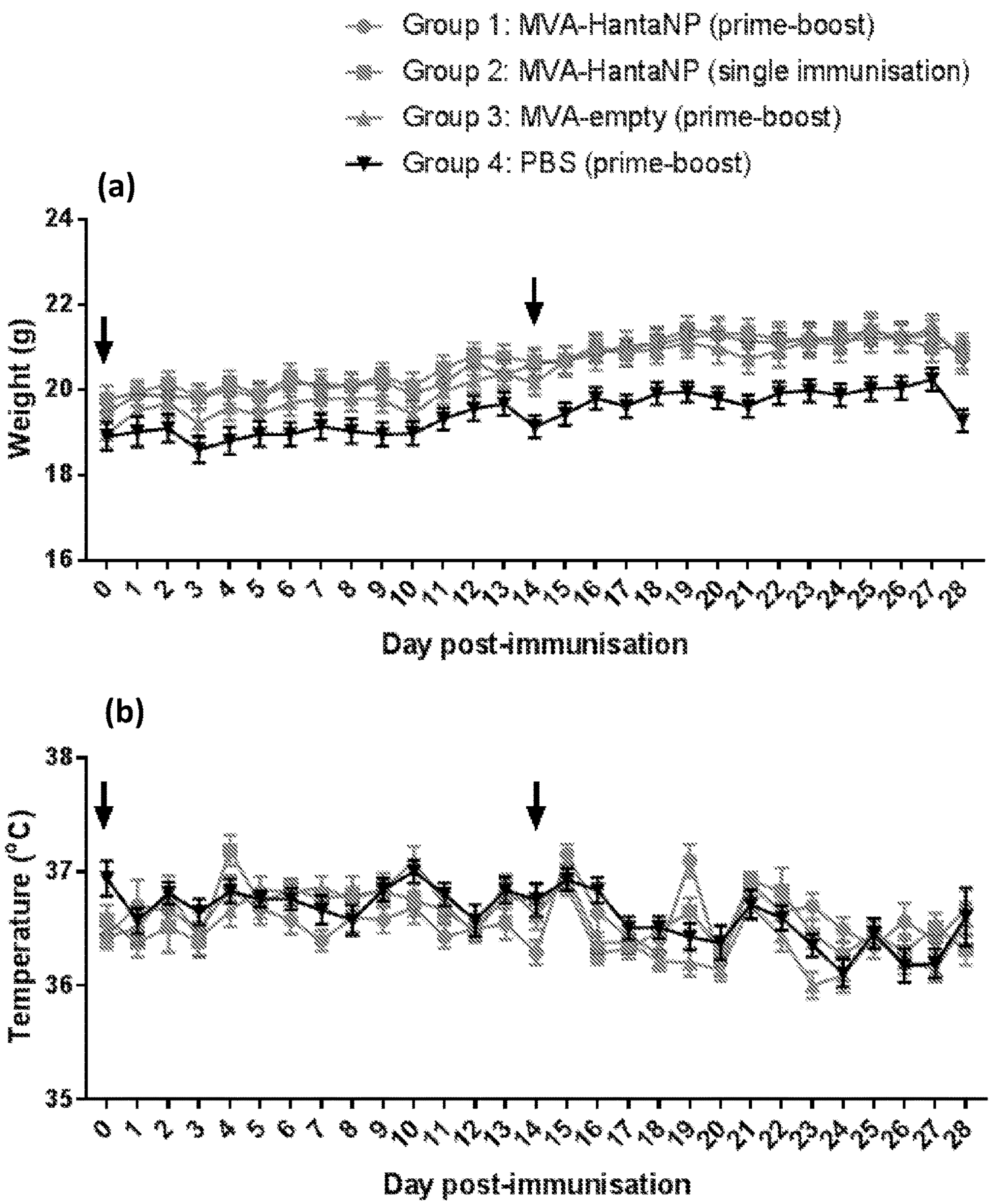

FIG. 4. Clinical scores (% daily weight gain) during the immunisation study. (a) Weight and (b) temperature of mice following prime immunisation (first arrow, day 0) and boost immunisation (second arrow, day 14).

Figure 5:
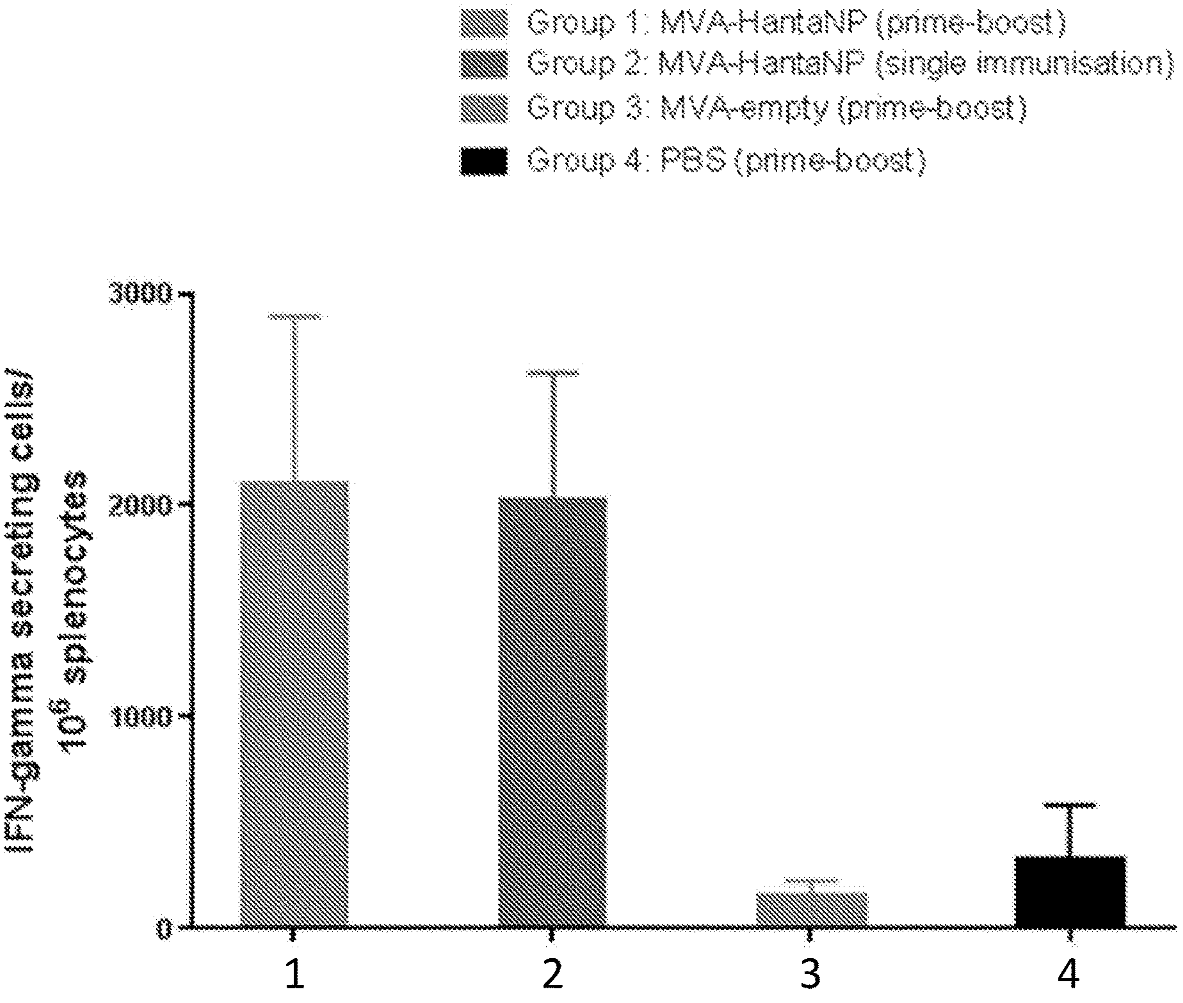

FIG. 5. Total ELISPOT response from vaccinated and unvaccinated mice.

Figure 6:
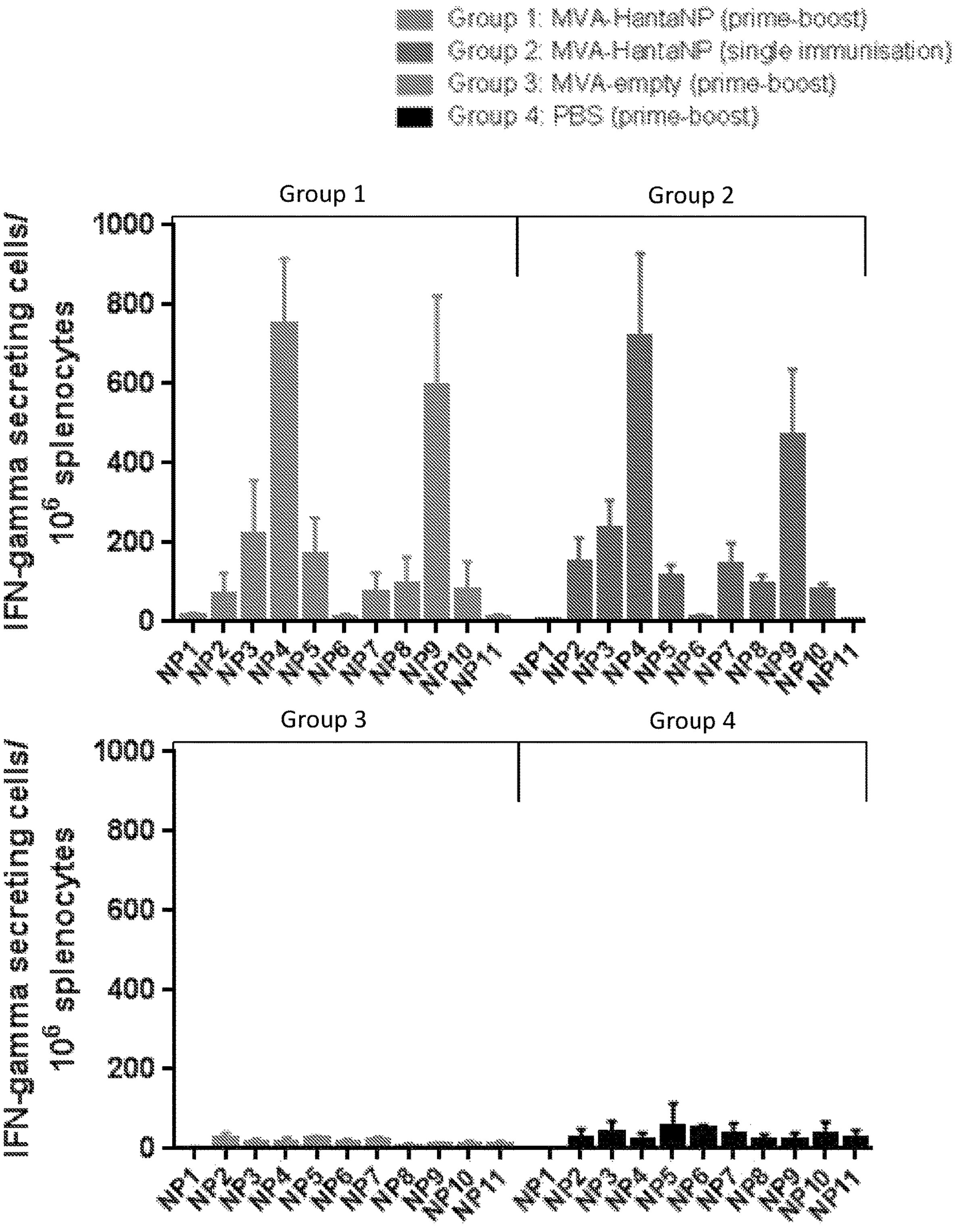

FIG. 6. Splenocyte IFN-γ ELISPOT re-stimulation responses to individual peptide pools ("NP1"-"NP11" therein). i) Group 1 indicates mice vaccinated with MVA-HantaNP prime and boost; ii) Group 2 indicates mice vaccinated with a single dose of MVA-HantaNP; iii) Group 3 indicates mice vaccinated with empty MVA wild-type prime and boost; and iv) Group 4 indicates PBS controls, prime and boost.

Figure 7:
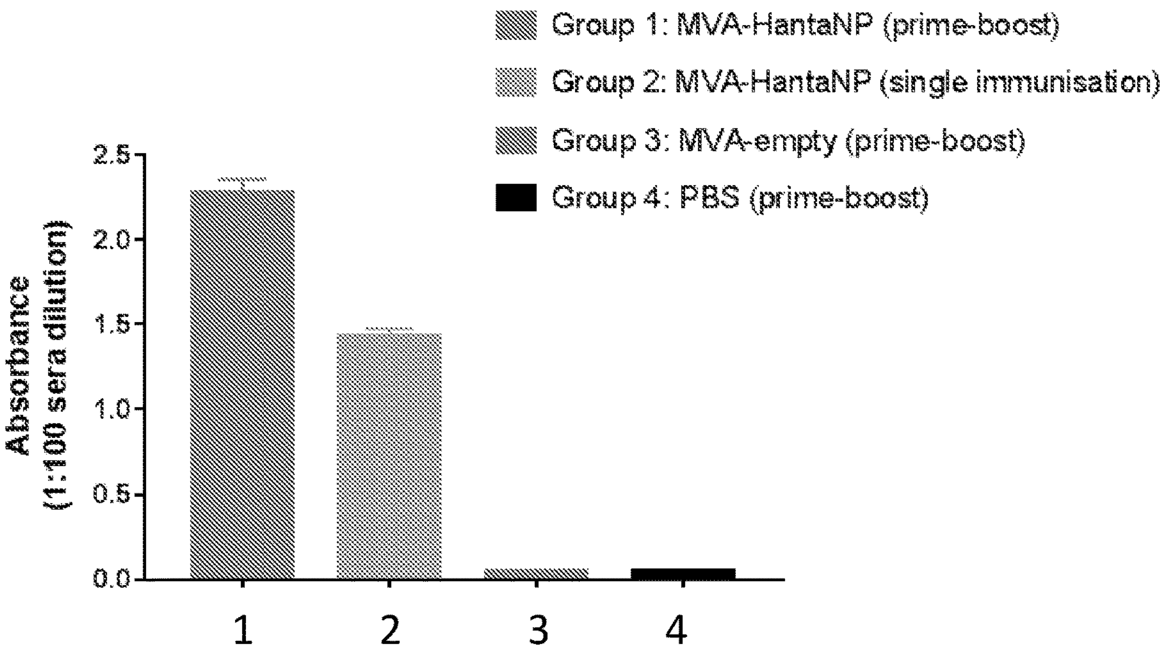

FIG. 7. IgG response to Hantavirus NP in mouse sera. Absorbance readings provide a readout of antibody binding activity to recombinant Hantavirus NP.

Figure 8:
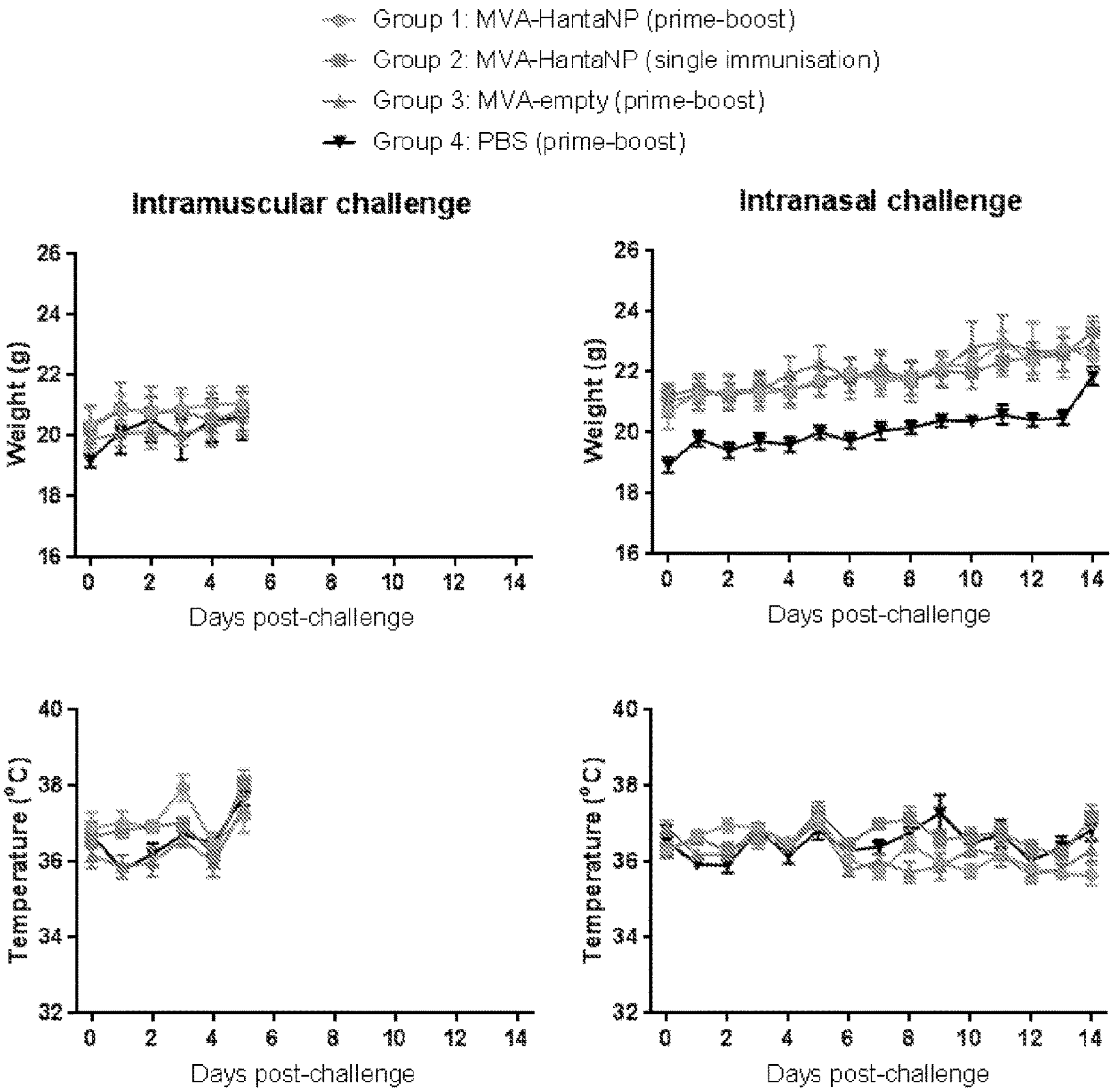

FIG. 8. Weight and temperature of mice following intramuscular challenge (left column) or intranasal challenge (right column) with Hantavirus.

Figure 9:
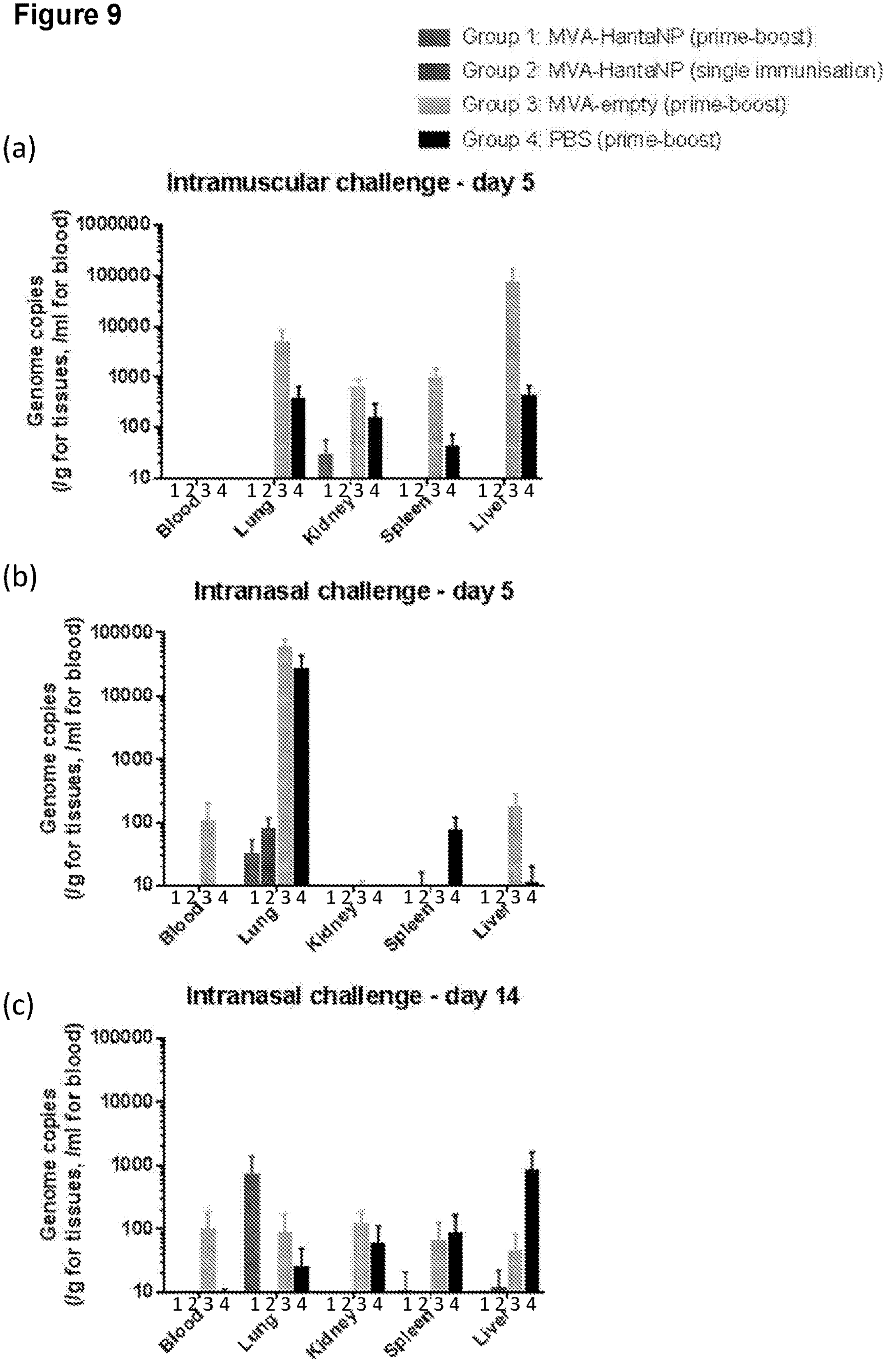

FIG. 9. Viral load in the blood, lung, kidney, spleen and liver of mice at (a) day 5 following intramuscular challenge; (b) day 5 following intranasal challenge; (c) day 14 following intranasal challenge.

Figure 10:
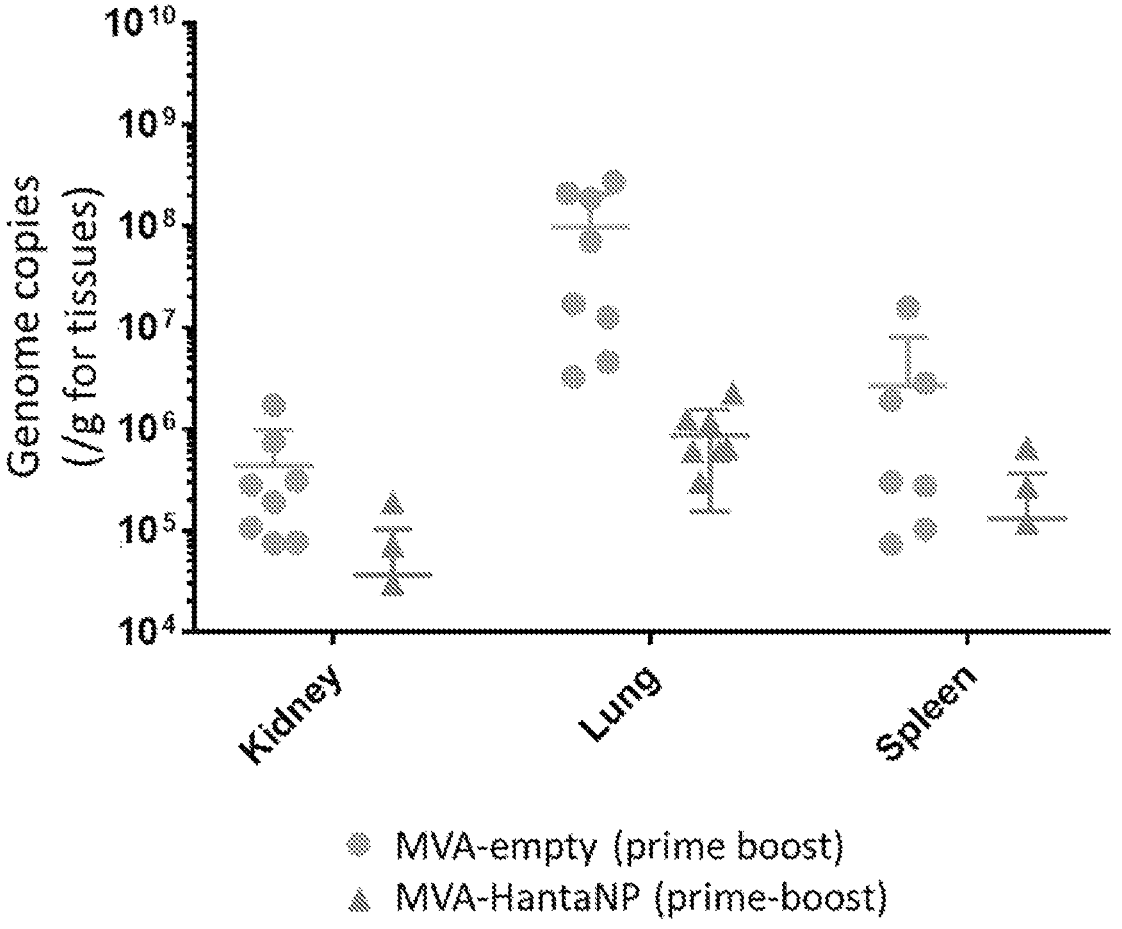

FIG. 10. Viral load in the kidney, lung and spleen of mice at day 5 following intranasal challenge. Results relating to immunisation with empty MVA wild-type vector are represented by circles; results relating to immunisation with MVA-HantaNP are represented by triangles.

EXAMPLES

Example 1. Preparation of an Example MVA-NP (Nucleoprotein) Vector

A cassette for MVAHantaNP (denoted "MVAHantaNP") was generated by GeneArt (Thermofisher) to contain a P11 promotor, Green fluorescence Protein (GFP) and MH5 promotor followed by a kozak sequence upstream of the NP sequence. The nucleoprotein sequence is a chimeric sequence containing two distinct sequences of Seoul and Hantaan. Downstream is a 24 residue linker sequence followed by a Flagtag epitope and stop codon. A schematic representation of MVAHantaNP is provided in FIG. 1(A).

The cassette was inserted into an SfiI/SfiI cloning site of plasmid pMS-RQ-Bb to produce plasmid 17ACNHBP_MVA-SEOV-HNT-NP_pMS-RQ (pMVAHantaNP).

A schematic representation of pMVAHantaNP is provided in FIG. 1(B), and the nucleic acid sequence of pMVAHantaNP is provided in SEQ ID NO: 33.

(SEQ ID NO: 33)

```
GTTGGTGGTCGCCATGGATGGTGTTATTGTATACTGTCTAAACGCGTTAGTAAAA

CATGGCGAGGAAATAAATCATATAAAAAATGATTTCATGATTAAACCATGTTGTG

AAAAAGTCAAGAACGTTCACATTGGCGGACAATCTAAAAACAATACAGTGATTG

CAGATTTGCCATATATGGATAATGCGGTATCCGATGTATGCAATTCACTGTATAA

AAAGAATGTATCAAGAATATCCAGATTTGCTAATTTGATAAAGATAGATGACGA

TGACAAGACTCCTACTGGTGTATATAATTATTTTAAACCTAAAGATGCCATTCCT

GTTATTATATCCATAGGAAAGGATAGAGATGTTTGTGAACTATTAATCTCATCTG

ATAAAGCGTGTGCGTGTATAGAGTTAAATTCATATAAAGTAGCCATTCTTCCCAT

GGATGTTTCCTTTTTTACCAAAGGAAATGCATCATTGATTATTCTCCTGTTTGATT

TCTCTATCGATGCGGCACCTCTCTTAAGAAGTGTAACCGATAATAATGTTATTAT

ATCTAGACACCAGCGTCTACATGACGAGCTTCCGAGTTCCAATTGGTTCAAGTTT

TACATAAGTATAAAGTCCGACTATTGTTCTATATTATATATGGTTGTTGATGGATC

TGTGATGCATGCAATAGCTGATAATAGAACTTACGCAAATATTAGCAAAAATAT

ATTAGACAATACTACAATTAACGATGAGTGTAGATGCTGTTATTTTGAACCACAG

ATTAGGATTCTTGATAGAGATGAGATGCTCAATGGATCATCGTGTGATATGAACA

GACATTGTATTATGATGAATTTACCTGATGTAGGCGAATTTGGATCTAGTATGTT

GGGGAAATATGAACCTGACATGATTAAGATTGCTCTTTCGGTGGCTGGGTACCAG

GCGCGCCTTTCATTTTGTTTTTTTCTATGCTATAAATGGTGAGCAAGGGCGAGGA

GCTGTTCACCGGGGTGGTGCCCATCCTGGTCGAGCTGGACGGCGACGTAAACGG

CCACAAGTTCAGCGTGTCCGGCGAGGGCGAGGGCGATGCCACCTACGGCAAGCT

GACCCTGAAGTTCATCTGCACCACCGGCAAGCTGCCCGTGCCCTGGCCCACCCTC
```

-continued

GTGACCACCCTGACCTACGGCGTGCAGTGCTTCAGCCGCTACCCCGACCACATGA

AGCAGCACGACTTCTTCAAGTCCGCCATGCCCGAAGGCTACGTCCAGGAGCGCA

CCATCTTCTTCAAGGACGACGGCAACTACAAGACCCGCGCCGAGGTGAAGTTCG

AGGGCGACACCCTGGTGAACCGCATCGAGCTGAAGGGCATCGACTTCAAGGAGG

ACGGCAACATCCTGGGGCACAAGCTGGAGTACAACTACAACAGCCACAACGTCT

ATATCATGGCCGACAAGCAGAAGAACGGCATCAAGGTGAACTTCAAGATCCGCC

ACAACATCGAGGACGGCAGCGTGCAGCTCGCCGACCACTACCAGCAGAACACCC

CCATCGGCGACGGCCCCGTGCTGCTGCCCGACAACCACTACCTGAGCACCCAGTC

CGCCCTGAGCAAAGACCCCAACGAGAAGCGCGATCACATGGTCCTGCTGGAGTT

CGTGACCGCCGCCGGGATCACTCTCGGCATGGACGAGCTGTACAAGTAAGAGCT

CCGGCCCGCTCGAGGCCGCTGGTACCCAACCTAAAAATTGAAAATAAATACAAA

GGTTCTTGAGGGTTGTGTTAAATTGAAAGCGAGAAATAATCATAAATAAGCCCG

GTGCCACCATGGCCACAATGGAAGAGATCCAGAGAGAGATCAGCGCCCACGAG

GGACAGCTGGTTATCGCCAGACAGAAAGTGAAGGACGCCGAGAAGCAGTACGA

GAAGGACCCCGACGATCTGAACAAGAGAGCCCTGCACGACAGAGAAAGCGTGG

CCGCCTCTATCCAGAGCAAGATCGATGAGCTGAAGAGACAGCTGGCCGACAGAA

TCGCCGCTGGCAAGAATATTGGCCAGGACAGAGATCCCACAGGCGTGGAACCTG

GCGATCACCTGAAAGAGAGAAGCGCCCTGTCCTATGGCAACACCCTGGACCTGA

ACAGCCTGGACATTGATGAGCCTACCGGCCAGACAGCCGACTGGCTGACAATCA

TTGTGTACCTGACCAGCTTCGTGGTCCCCATCATCCTGAAGGCCCTGTACATGCT

GACCACCAGAGGCAGACAGACCAGCAAGGACAACAAGGGCATGAGAATCCGGT

TCAAGGATGACAGCAGCTACGAGGACGTGAACGGCATTAGAAAGCCCAAGCACC

TGTACGTGTCCATGCCTAACGCTCAGAGCAGCATGAAGGCCGAGGAAATCACCC

CTGGCAGATTCAGAACAGCCGTGTGCGGACTGTACCCCGCTCAGATCAAGGCCA

GAAACATGGTGTCCCCAGTGATGAGCGTCGTGGGATTTCTGGCCCTGGCTAAGG

ACTGGACCAGCAGGATTGAGGAATGGCTGGGAGCCCCCTTGCAAGTTTATGGCCG

AGTCTCCTATCGCCGGCAGCCTGTCTGGCAACCCCGTGAATAGAGACTACATCAG

ACAGAGGCAGGGCGCTCTGGCCGGAATGGAACCCAAAGAATTTCAGGCCCTGCG

GCAGCACTCTAAGGATGCCGGATGTACCCTGGTGGAACACATTGAGAGCCCCAG

CAGCATCTGGGTTTTCGCTGGCGCTCCTGATAGATGCCCTCCTACCTGTCTGTTTG

TTGGCGGAATGGCCGAGCTGGGCGCCTTCTTTAGCATTCTGCAGGACATGCGGAA

TACCATCATGGCCAGCAAGACCGTGGGCACCGCCGATGAGAAGCTGAGAAAGAA

GTCCAGCTTCTACCAGAGCTACCTGCGGAGAACCCAGAGCATGGGCATTCAGCT

GGACCAGAGAATCATCGTGATGTTCATGGTGGCCTGGGGCAAAGAAGCCGTGGA

CAATTTTCACCTGGGCGACGACATGGACCCCGAGCTGAGATCTCTGGCCCAGATC

CTGATCGACCAGAAAGTCAAAGAGATCTCCAATCAAGAGCCCATGAAGCTGATG

CTGAGCTACGGCAACGTGCTGGATCTGAACCACCTGGATATCGACGAGCCAACA

GGACAGACCGCTGATTGGCTGGGCATCGTGATCTACCTGACCTCCTTTGTGGTGC

CTATTCTGCTCAAAGCCCTCTATATGCTGACAACACGCGGAAGGCAGACCACCA

AAGATAACAAAGGCACCCGGATCAGGTTTAAGGACGACAGCTCCTTTGAGGATG

TCAACGGCATCCGGAAACCTAAGCACCTCTATGTGTCTCTGCCCAATGCACAGTC

-continued

CTCCATGAAGGCAGAAGAGATCACACCAGGCCGGTACAGAACCGCCATCTGTGG

ACTGTATCCTGCACAAATCAAAGCCCGGCAGATGATCAGCCCCGTGATGTCCGTT

ATCGGATTCCTGGCTCTGGCCAAAGATTGGAGCGACAGGATCGAGCAGTGGCTG

AGCGAGCCTTGCAAGCTGCTTCCTGATACAGCCGCTGTGTCACTGCTTGGCGGCC

CTGCCACAAACAGAGATTACCTGAGACAGAGACAGGTGGCACTGGGCAACATGG

AAACAAAAGAGAGCAAGGCCATCCGGCAGCATGCCGAAGCTGCTGGCTGTAGCA

TGATCGAGGATATCGAGTCCCCTAGCTCCATTTGGGTGTTCGCAGGGGCCCCAGA

TAGATGTCCACCAACATGCCTGTTCATTGCCGGCATGGCTGAACTGGGAGCTTTT

TTCAGCATCCTCCAGGATATGCGCAACACGATTATGGCCTCCAAGACAGTGGGA

ACCAGCGAGGAAAAGCTGCGGAAGAAAAGCAGCTTTTACCAGTCTTACCTGAGG

CGGACCCAGTCCATGGGGATCCAACTGGATCAGCGGATCATTGTGCTGTTTATGG

TCGCTTGGGGAAAAGAGGCTGTCGATAACTTCCACCTGGGAGATGATATGGATC

CTGAACTGCGGACCCTGGCTCAGTCCCTGATCGATGTGAAAGTGAAAGAAATTA

GTAATCAAGAACCCCTCAAGCTGGACCTGGAAGGCCCTAGATTCGAGGACTACA

AGGACGATGACGACAAGTGACTCGACCTGCAGTTTTTATGGAAAGTTTTATAGGT

AGTTGATAGAACAAAATACATAATTTTGTAAAAATAAATCACTTTTTATACTAAT

ATGACACGATTACCAATACTTTTGTTACTAATATCATTAGTATACGCTACACCTTT

TCCTCAGACATCTAAAAAAATAGGTGATGATGCAACTTTATCATGTAATCGAAAT

AATACAAATGACTACGTTGTTATGAGTGCTTGGTATAAGGAGCCCAATTCCATTA

TTCTTTTAGCTGCTAAAAGCGACGTCTTGTATTTTGATAATTATACCAAGGATAA

AATATCTTACGACTCTCCATACGATGATCTAGTTACAACTATCACAATTAAATCA

TTGACTGCTAGAGATGCCGGTACTTATGTATGTGCATTCTTTATGACATCGCCTAC

AAATGACACTGATAAAGTAGATTATGAAGAATACTCCACAGAGTTGATTGTAAA

TACAGATAGTGAATCGACTATAGACATAATACTATCTGGATCTACACATTCACCG

GAAACTAGTTG pMVAHantaNP comprises:
DelIII Left flank:

(SEQ ID NO: 34)

GTTGGTGGTCGCCATGGATGGTGTTATTGTATACTGTCTAAACGCGTTAGTAAAA

CATGGCGAGGAAATAAATCATATAAAAAATGATTTCATGATTAAACCATGTTGTG

AAAAAGTCAAGAACGTTCACATTGGCGGACAATCTAAAAACAATACAGTGATTG

CAGATTTGCCATATATGGATAATGCGGTATCCGATGTATGCAATTCACTGTATAA

AAAGAATGTATCAAGAATATCCAGATTTGCTAATTTGATAAAGATAGATGACGA

TGACAAGACTCCTACTGGTGTATATAATTATTTTAAACCTAAAGATGCCATTCCT

GTTATTATATCCATAGGAAAGGATAGAGATGTTTGTGAACTATTAATCTCATCTG

ATAAAGCGTGTGCGTGTATAGAGTTAAATTCATATAAAGTAGCCATTCTTCCCAT

GGATGTTTCCTTTTTTACCAAAGGAAATGCATCATTGATTATTCTCCTGTTTGATT

TCTCTATCGATGCGGCACCTCTCTTAAGAAGTGTAACCGATAATAATGTTATTAT

ATCTAGACACCAGCGTCTACATGACGAGCTTCCGAGTTCCAATTGGTTCAAGTTT

TACATAAGTATAAAGTCCGACTATTGTTCTATATTATATATGGTTGTTGATGGATC

TGTGATGCATGCAATAGCTGATAATAGAACTTACGCAAATATTAGCAAAAATAT

ATTAGACAATACTACAATTAACGATGAGTGTAGATGCTGTTATTTTGAACCACAG

-continued

ATTAGGATTCTTGATAGAGATGAGATGCTCAATGGATCATCGTGTGATATGAACA

GACATTGTATTATGATGAATTTACCTGATGTAGGCGAATTTGGATCTAGTATGTT

GGGGAAATATGAACCTGACATGATTAAGATTGCTCTTTCGGTGGCTGG

First linker:

(SEQ ID NO: 35)

GTACCAGGCGCGCC p11:

(SEQ ID NO: 36)

TTTCATTTTGTTTTTTTCTATGCTATAA

GFP:

(SEQ ID NO: 37)

ATGGTGAGCAAGGGCGAGGAGCTGTTCACCGGGGTGGTGCCCATCCTGGTCGAG

CTGGACGGCGACGTAAACGGCCACAAGTTCAGCGTGTCCGGCGAGGGCGAGGGC

GATGCCACCTACGGCAAGCTGACCCTGAAGTTCATCTGCACCACCGGCAAGCTG

CCCGTGCCCTGGCCCACCCTCGTGACCACCCTGACCTACGGCGTGCAGTGCTTCA

GCCGCTACCCCGACCACATGAAGCAGCACGACTTCTTCAAGTCCGCCATGCCCGA

AGGCTACGTCCAGGAGCGCACCATCTTCTTCAAGGACGACGGCAACTACAAGAC

CCGCGCCGAGGTGAAGTTCGAGGGCGACACCCTGGTGAACCGCATCGAGCTGAA

GGGCATCGACTTCAAGGAGGACGGCAACATCCTGGGGCACAAGCTGGAGTACAA

CTACAACAGCCACAACGTCTATATCATGGCCGACAAGCAGAAGAACGGCATCAA

GGTGAACTTCAAGATCCGCCACAACATCGAGGACGGCAGCGTGCAGCTCGCCGA

CCACTACCAGCAGAACACCCCCATCGGCGACGGCCCCGTGCTGCTGCCCGACAA

CCACTACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCATGGAC

GAGCTGTACAAGTAA

Second linker:

(SEQ ID NO: 38)

GAGCTCCGGCCCGCTCGAGGCCGCTGGTACCCAACCT

MH5 promoter:

(SEQ ID NO: 39)

AAAAATTGAAAATAAATACAAAGGTTCTTGAGGGTTGTGTTAAATTGAAAGCGA

GAAATAATCATAAATA

Third linker:
AGCCCGGT

Kozak sequence:

(SEQ ID NO: 41)

GCCACCATGG.
The 3' end of the Kozak sequence overlaps with the four nucleic acids at the 5' end of SEQ ID NO: 29.

Nucleoprotein (SEQ ID NO: 29)

Fourth linker:

(SEQ ID NO: 42)

GACCTGGAAGGCCCTAGATTCGAG

Flag tag:

(SEQ ID NO: 43)

GACTACAAGGACGATGACGACAAG

STOP:
TGA

Fifth linker:

(SEQ ID NO: 44)

CTCGACCTGCAGTTTTTATG

-continued

```
DelIII Right flank:
                                              (SEQ ID NO: 45)
GAAAGTTTTATAGGTAGTTGATAGAACAAAATACATAATTTTGTAAAAATAAATC

ACTTTTTATACTAATATGACACGATTACCAATACTTTTGTTACTAATATCATTAGT

ATACGCTACACCTTTTCCTCAGACATCTAAAAAAATAGGTGATGATGCAACTTTA

TCATGTAATCGAAATAATACAAATGACTACGTTGTTATGAGTGCTTGGTATAAGG

AGCCCAATTCCATTATTCTTTTAGCTGCTAAAAGCGACGTCTTGTATTTTGATAAT

TATACCAAGGATAAAATATCTTACGACTCTCCATACGATGATCTAGTTACAACTA

TCACAATTAAATCATTGACTGCTAGAGATGCCGGTACTTATGTATGTGCATTCTTT

ATGACATCGCCTACAAATGACACTGATAAAGTAGATTATGAAGAATACTCCACA

GAGTTGATTGTAAATACAGATAGTGAATCGACTATAGACATAATACTATCTGGAT

CTACACATTCACCGGAAACTAGTTG
```

The plasmid DNA was purified from transformed bacteria (*E. coli* K12 DH10B™ T1R) and concentration determined by UV spectroscopy by GeneArt (Thermofisher).

BHK-21 cells were infected with MVA 1974 at a multiplicity of infection of 0.05. Infected cells were transfected with pMVAHantaNP using lipofectamine (Life Technologies) as directed by the manufacturer. The resulting recombinant MVAHantaNP was serially plaque-purified 4 times in Chick Embryo Fibroblast ("CEF") cells, based on GFP expression. MVAHantaNP was amplified on CEF cells, purified by sucrose cushion centrifugation and titrated by plaque assay on CEF cells prior to in vivo use. Plaques were visualised using GFP fluorescence and by immunostaining with rabbit anti-vaccinia antibody (AbD Serotec, UK) and Vectastain Universal ABC-AP kit (Vector laboratories, USA). Genomic DNA from infected cells was extracted using Wizard SV genomic DNA purification system (Promega, USA) and used as a template in PCR with KAPA2G Fast HotStart PCR Kit (KAPABiosystems, USA) for genotype analysis.

Polymerase chain reaction (PCR) confirmed presence of the MVAHantaNP construct. One set of primers was designed specifically to check for the Hanta NP to the MVA flanking region with an expected size of 3260 bp—this is shown in FIG. 2.

Sequencing of the expressed protein confirmed very high sequence fidelity. Recombinant purified MVAHantaNP was then bulked-up in stages, by tissue culture into increasing sized flasks. Initially the MVAHantaNP was grown in a small flask of Chicken Embryo Fibroblast (CEF) cells and harvested before infecting into a slightly larger flask of CEF cells. This process was repeated into increasingly larger flasks until the MVAHantaNP successfully infected 10× large flasks of CEF cells. Sucrose cushion centrifugation was performed; viral pellets were re-suspended in PBS ready for immunogenicity studies. A total of six batches was produced. Batches 2+3 and 4+5+6 were pooled into single samples and titrated for viral concentration.

The purified vaccine batches align to a positive control (the original received plasmid from Geneart). A second set of primers were designed to identify the entire insert, from both MVA flanking regions. The results indicate presence of pure recombinant MVA (MVA containing the insert) in all vaccine batches. Again the original plasmid was used as a positive control and all vaccine batches have the same expected size product as the positive control.

Primer details are as follows:

```
SEQ ID NO: 46:
CGGCACCTCTCTTAAGAAGT (Fwd targets Del III Left
flank)

SEQ ID NO: 47:
GTGTAGCGTATACTAATGATATTAG (Rev targets Del III
Right flank)

SEQ ID NO: 48:
GGAGTACAACTACAACAGCCACAACG (Fwd targets GFP)
```

The GFP Fwd primer binds to the GFP sequence and, when used in combination with the Rev Del III Right flank primer, covers the GFP through the nucleoprotein to the right MVA flank, and specifically identifies presence of the NP gene.

Detection of Protein Expression

CEF cells were infected with MVAHantaNP at a multiplicity of infection of 0.05 and incubated at 37° C. in Modified Eagle Medium (MEM) supplemented with 2% FBS (Sigma-Aldrich. UK). The medium was removed after 48 hours once good GFP fluorescence and CPE was observed microscopically. Cells were lysed with 1×LDS Nupage® reducing sample buffer (Nupage® LDS sample buffer containing 1× Nupage® sample reducing buffer) (Thermofisher, UK), transferred to Eppendorf tubes and heated at 70° C. for 10 minutes. Uninfected cells were treated in the same manner as a negative control. MVAHantaNP lysates were subjected to SDS-PAGE on a 4-12% Bis-Tris gel (Life technologies) and proteins transferred to a nitrocellulose membrane. The nitrocellulose membrane was blocked using 5% milk powder (Merck Millipore), then incubated in the presence of a primary antibody (Rabbit anti-V5 polyclonal (Invitrogen) at 1/1000 in PBS-0.05% Tween) for 1-2 hours rocking, before washing in PBS containing 0.05% Tween-20 (Sigma-Aldrich) 3 times. Membranes were incubated in the presence of a HRP-conjugated secondary antibody (anti-rabbit IgG peroxidase (Sigma-Aldrich) at 1/1000 in PBS-0.05% Tween) for 1 hour rocking and washed as before. Protein expression was determined by detection of bound antibody using Pierce ECL WB substrate kit (Thermofisher) according to the manufacturer's instructions and visualised in a Chemi-Illuminescent Imager (Syngene). Molecular weights were determined using molecular ladder MagicMark XP Western Protein Standard (Invitrogen) as a reference.

Western blot analysis (see FIG. 3) confirms expression of the flag tag located downstream from the NP. The expected size of the protein (the NP+linker and flag tag) is 89 kDa and the protein sequence is provided in SEQ ID NO: 49. Expression is observed from the passage 3 picks through to the vaccine batches (the inventors observed low level protein degradation, which is not believed to be significant). The band of interest is located at the expected size of the protein which again suggests good expression.

(SEQ ID NO: 49)

```
MATMEEIQREISAHEGQLVIARQKVKDAEKQYEKDPDDLNKRALHDRESV
AASIQSKIDELKRQLADRIAAGKNIGQDRDPTGVEPGDHLKERSALSYGN
TLDLNSLDIDEPTGQTADWLTIIVYLTSFVVPIILKALYMLTTRGRQTSK
DNKGMRIRFKDDSSYEDVNGIRKPKHLYVSMPNAQSSMKAEEITPGRFRT
AVCGLYPAQIKARNMVSPVMSVVGFLALAKDWTSRIEEWLGAPCKFMAES
PIAGSLSGNPVNRDYIRQRQGALAGMEPKEFQALRQHSKDAGCTLVEHIE
SPSSIWVFAGAPDRCPPTCLFVGGMAELGAFFSILQDMRNTIMASKTVGT
ADEKLRKKSSFYQSYLRRTQSMGIQLDQRIIVMFMVAWGKEAVDNFHLGD
DMDPELRSLAQILIDQKVKEISNQEPMKLMLSYGNVLDLNHLDIDEPTGQ
TADWLGIVIYLTSFVVPILLKALYMLTTRGRQTTKDNKGTRIRFKDDSSE
EDVNGIRKPKHLYVSLPNAQSSMKAEEITPGRYRTAICGLYPAQIKARQM
ISPVMSVIGFLALAKDWSDRIEQWLSEPCKLLPDTAAVSLLGGPATNRDY
LRQRQVALGNMETKESKAIRQHAEAAGCSMIEDIESPSSIWVFAGAPDRC
PPTCLFIAGMAELGAFFSILQDMRNTIMASKTVGTSEEKLRKKSSFYQSY
LRRTQSMGIQLDQRIIVLFMVAWGKEAVDNFHLGDDMDPELRTLAQSLID
VKVKEISNQEPLKLDLEGPRFEDYKDDDDK
```

The amino acid sequence of SEQ ID NO 49 corresponds to the amino acid sequence of SEQ ID NO: 31 plus the expressed fourth linker and flag tag.

Example 2. MVAHantaNP Immunogenicity in A129 Mice 80 male 6-8 week old A129 mice were randomly divided into 4 groups and ear tagged prior to vaccinations.

Group 1 received a two dose vaccination of MVAHantaNP in endotoxin free phosphate buffered saline (PBS) at $1\times10^7$ pfu per animal on days 0 and 14.

Group 2 received a single vaccine shot of MVAHantaNP in endotoxin free PBS at $1\times10^7$ plaque forming units (pfu) per animal on day 14.

Group 3 received a two dose vaccination of MVA empty vector in endotoxin free PBS at $1\times10^7$ pfu per animal on days 0 and 14.

Group 4 received a two dose vaccination of endotoxin free PBS as a negative control on days 0 and 14.

All mice were injected intramuscularly into the caudal thigh. 100 μl was administered at each vaccination (50 μl into each thigh). Animal weights were recorded daily throughout the study. 5 animals were euthanised from each group and spleen tissue and blood collected on day 28 after the primary vaccination. All efforts were made to minimise animal suffering. These studies were approved by the ethical review process of PHE, Porton Down, UK and the Home Office, UK via project license number 30/2993. Work was performed in accordance with the Animals (Scientific procedures) Act 1986 and the Home Office (UK) Code of Practice for the Housing and Care of Animals Used in Scientific Procedures (1989).

Throughout the study, no clinical signs were observed with regards to the vaccinations and all mice gained weight as expected (see FIG. 4*a*). All four groups gained weight throughout the study as expected, and group 4 body weights were consistently lower than groups 1-3. By the end of the study all the groups observed a similar % weight gain. These clinical data demonstrate that the mice tolerated the vaccine without adverse effects.

To determine the T-cell responses in immunised animals, an interferon-gamma ELISPOT assay was used to measure frequencies of responsive T-cells after stimulation with Hantavirus specific peptides.

Spleens from test animals were collected aseptically, homogenised, and red blood cells lysed. Splenocytes were resuspended in RPMI medium (Sigma-Aldrich) supplemented with 5% FBS, 2 mM L-Glutamine, 100 U penicillin & 0.1 mg/ml streptomycin, 50 mM 2-mercaptoethanol and 25 mM HEPES solution (Sigma-Aldrich). Splenocytes were assessed for antigen recall response via IFN-γ ELISPOT (Mabtech, Sweden), performed as per the manufacturer's instructions. Cells were seeded in PVDF microtitre plates at 2×10e6 per well and re-stimulated with peptide pools (JPT, Berlin).

Peptides spanning the Hanta NP protein sequence were 15 residues long, with an overlap of 11 residues between peptides. 189 peptides were produced in total that were tested in eleven peptide pools (see Table 1).

TABLE 1

Peptide pools (start amino acid ("AA") numbering corresponds to the amino acid numbering in SEQ ID NO: 31)

| SEQ ID NO | Start AA | Sequence | Pool number |
|---|---|---|---|
| 50 | 1 | MATMEEIQREISAHE | 1 |
| 51 | 5 | EEIQREISAHEGQLV | |
| 52 | 9 | REISAHEGQLVIARQ | |
| 53 | 13 | AHEGQLVIARQKVKD | |
| 54 | 17 | QLVIARQKVKDAEKQ | |
| 55 | 21 | ARQKVKDAEKQYEKD | |
| 56 | 25 | VKDAEKQYEKDPDDL | |
| 57 | 29 | EKQYEKDPDDLNKRA | |
| 58 | 33 | EKDPDDLNKRALHDR | |
| 59 | 37 | DDLNKRALHDRESVA | |
| 60 | 41 | KRALHDRESVAASIQ | |
| 61 | 45 | HDRESVAASIQSKID | |
| 62 | 49 | SVAASIQSKIDELKR | |
| 63 | 53 | SIQSKIDELKRQLAD | |
| 64 | 57 | KIDELKRQLADRIAA | |
| 65 | 61 | LKRQLADRIAAGKNI | |
| 66 | 65 | LADRIAAGKNIGQDR | |
| 67 | 69 | IAAGKNIGQDRDPTG | 2 |
| 68 | 73 | KNIGQDRDPTGVEPG | |
| 69 | 77 | QDRDPTGVEPGDHLK | |
| 70 | 81 | PTGVEPGDHLKERSA | |
| 71 | 85 | EPGDHLKERSALSYG | |
| 72 | 89 | HLKERSALSYGNTLD | |
| 73 | 93 | RSALSYGNTLDLNSL | |
| 74 | 97 | SYGNTLDLNSLDIDE | |
| 75 | 101 | TLDLNSLDIDEPTGQ | |
| 76 | 105 | NSLDIDEPTGQTADW | |
| 77 | 109 | IDEPTGQTADWLTII | |
| 78 | 113 | TGQTADWLTIIVYLT | |
| 79 | 117 | ADWLTIINYLTSEVV | |
| 80 | 121 | TIIVYLTSFVVPIIL | |
| 81 | 125 | YLTSFVVPIILKALY | |
| 82 | 129 | FVVPIILKALYMLTT | |
| 83 | 133 | IILKALYMLTTRGRQ | |
| 84 | 137 | ALYMLTTRGRQTSKD | 3 |
| 85 | 141 | LTTRGRQTSKDNKGM | |
| 86 | 145 | GRQTSKDNKGMRIRF | |

TABLE 1-continued

Peptide pools (start amino acid ("AA") numbering corresponds to the amino acid numbering in SEQ ID NO: 31)

| SEQ ID NO | Start AA | Sequence | Pool number |
|---|---|---|---|
| 87 | 149 | SKDNKGMRIRFKDDS | |
| 88 | 153 | KGMRIRFKDDSSYED | |
| 89 | 157 | IRFKDDSSYEDVNGI | |
| 90 | 161 | DDSSYEDVNGIRKPK | |
| 91 | 165 | YEDVNGIRKPKHLYV | |
| 92 | 169 | NGIRKPKHLYVSMPN | |
| 93 | 173 | KPKHLYVSMPNAQSS | |
| 94 | 177 | LYVSMPNAQSSMKAE | |
| 95 | 181 | MPNAQSSMKAEEITP | |
| 96 | 185 | QSSMKAEEITPGRFR | |
| 97 | 189 | KAEEITPGRFRTAVC | |
| 98 | 193 | ITPGRFRIAVCGLYP | |
| 99 | 197 | RFRTAVCGLYPAQIK | |
| 100 | 201 | AVCGLYPAQIKARNM | |
| 101 | 205 | LYPAQIKARNMVSPV | 4 |
| 102 | 209 | QIKARNMVSPVMSVV | |
| 103 | 213 | RNMVSPVMSVVGFLA | |
| 13 | 217 | SPVMSVVGFLALAKD | |
| 104 | 221 | SVVGFLALAKDWTSR | |
| 105 | 225 | FLALAKDWTSRIEEW | |
| 106 | 229 | AKDWTSRIEEWLGAP | |
| 107 | 233 | TSRIEEWLGAPCKFM | |
| 108 | 237 | EEWLGAPCKFMAESP | |
| 109 | 241 | GAPCKFMAESPIAGS | |
| 110 | 245 | KFMAESPIAGSLSGN | |
| 111 | 249 | ESPIAGSLSGNPVNR | |
| 112 | 253 | AGSLSGNPVNRDYIR | |
| 113 | 257 | SGNPVNRDYIRQRQG | |
| 114 | 261 | VNRDYIRQRQGALAG | |
| 115 | 265 | YIRQRQGALAGMEPK | |
| 116 | 269 | RQGALAGMEPKEFQA | |
| 117 | 273 | LAGMEPKEFQALRQH | 5 |
| 118 | 277 | EPKEFQALRQHSKDA | |
| 119 | 281 | FQALRQHSKDAGCTL | |
| 120 | 285 | RQHSKDAGCTLVEHI | |
| 121 | 289 | KDAGCTLVEHIESPS | |
| 122 | 293 | CTLVEHIESPSSIWV | |
| 123 | 297 | EHIESPSSIWVFAGA | |
| 124 | 301 | SPSSIWVFAGAPDRC | |
| 125 | 305 | IWVFAGAPDRCPPTC | |
| 126 | 309 | AGAPDRCPPTCLFVG | |
| 127 | 313 | DRCPPTCLFVGGMAF | |
| 128 | 317 | PTCLEVGGMAELGAF | |
| 179 | 321 | FVGGMAELGAFFSIL | |
| 130 | 325 | MAELGAFFSILQDMR | |
| 131 | 329 | GAFFSILQDMRNTIM | |
| 132 | 333 | SILQDMRNTIMASKT | |
| 133 | 337 | DMRNTIMASKTVGTA | |
| 134 | 341 | TIMASKTVGTADEKL | 6 |
| 135 | 345 | SKTVGTADEKLRKKS | |
| 136 | 349 | GTADEKLRKKSSFYQ | |
| 137 | 353 | EKLRKKSSFYQSYLR | |
| 138 | 357 | KKSSFYQSYLRRTQS | |
| 139 | 361 | FYQSYLRRTQSMGIQ | |
| 140 | 365 | YLRRTQSMGIQLDQR | |
| 141 | 369 | TQSMGIQLDQRIIVM | |
| 142 | 373 | GIQLDQRIIVMFMVA | |
| 143 | 377 | DQRIIVMFMVAWGKE | |
| 144 | 381 | IVMFMVAWGKEAVDN | |
| 145 | 385 | MVAWGKEAVDNFHLG | |
| 146 | 389 | GKEAVDNFHLGDDMD | |
| 147 | 393 | VDNFHLGDDMDPELR | |
| 148 | 397 | HLGDDMDPELRSLAQ | |
| 149 | 401 | DMDPELRSLAQILID | |
| 150 | 405 | ELRSLAQILIDQKVK | |
| 151 | 409 | LAQILIDQKVKEISN | 7 |
| 152 | 413 | LIDQKKVEISNQEPM | |
| 153 | 417 | KNKEISNQEMIKLML | |
| 154 | 421 | ISNQEPMKLMLSYGN | |
| 155 | 425 | EPMKLMLSYGNVLDL | |
| 156 | 429 | LMLSYGNVLDLNHLD | |
| 157 | 433 | YGNYLDLNHLDIDEP | |
| 158 | 437 | LDLNHLDIDEPTGQI | |
| 159 | 441 | HIDIDEPTGQTADWL | |
| 160 | 445 | DEPTGQTADWLGIVI | |
| 161 | 449 | GQTADWLGIVIYLTS | |
| 162 | 453 | DWLGIVIYLTSFVVP | |
| 163 | 457 | IVIYLTSFVVPILLK | |
| 164 | 461 | LTSFVVPILLKALYM | |
| 165 | 465 | VVPILLKALYMLTTR | |
| 166 | 469 | LLKALYMLTTRGRQT | |
| 167 | 473 | LYMLTTRGRQTTKDN | |
| 168 | 477 | TTRGRQTTKDNKGTR | 8 |
| 169 | 481 | RQTTKDNKGTRIRFK | |
| 170 | 485 | KDNKGTRIRFKDDSS | |
| 171 | 489 | GTRIRFKDDSSFEDV | |
| 172 | 493 | RFKDDSSFEDVNGIR | |
| 173 | 497 | DSSFEDVNGIRKPKH | |
| 174 | 501 | EDVNGIRKPKHLYVS | |
| 175 | 505 | GIRKPKHLYVSLPNA | |
| 176 | 509 | PKHLYVSLPNAQSSM | |
| 177 | 513 | YVSLPNAQSSMKAEE | |
| 178 | 517 | PNAQSSMKAEEITPG | |
| 179 | 521 | SSMKAEEITPGRYRT | |
| 180 | 525 | AEEITPGRYRTAICG | |
| 181 | 529 | TPGRYRTAICGLYPA | |
| 182 | 533 | YRTAICGLYPAQIKA | |
| 183 | 537 | ICGLYPAQIKARQMI | |
| 184 | 541 | YPAQIKARQMISPVM | |
| 185 | 545 | IKARQMISPVMSVIG | 9 |
| 186 | 549 | QMISPVMSVIGFLAL | |
| 14 | 553 | PVMSVIGFLALAKDW | |
| 187 | 557 | VIGFLALAKDWSDRI | |
| 188 | 561 | LALAKDWSDRIEQWL | |
| 189 | 565 | KDWSDRIEQWLSEPC | |
| 190 | 569 | DRIEQWLSEPCKLLP | |
| 191 | 573 | QWLSEPCKLLPDTAA | |
| 192 | 577 | EPCKLLPDTAAVSLL | |
| 193 | 581 | LLPDTAAVSLLGGPA | |
| 194 | 585 | TAAVSLLGGPATNRD | |
| 195 | 589 | SLLGGPATNRDYLRQ | |
| 196 | 593 | GPATNRDYLRQRQVA | |
| 197 | 597 | NRDYLRQRQVALGNM | |
| 198 | 601 | LRQRQVALGNMETKE | |
| 199 | 605 | QVALGNMETKESKAI | |
| 200 | 609 | GNMETKESKAIRQHA | |
| 201 | 613 | TKESKAIRQHAEAAG | 10 |
| 202 | 617 | KAIRQHAEAAGCSMI | |
| 203 | 621 | QHAEAAGCSMIEDIE | |
| 204 | 625 | AAGCSMIEDIESPSS | |
| 205 | 629 | SMIEDIESPSSIWVF | |
| 206 | 633 | DIESPSSIWVFAGAP | |
| 207 | 637 | PSSIWVFAGAPDRCP | |
| 208 | 641 | WVFAGAPDRCPPTCL | |
| 209 | 645 | GAPDRCPPTCLFIAG | |
| 210 | 649 | RCPPICLFIAGMAEL | |
| 211 | 653 | TCLFIAGMAELGAFF | |
| 212 | 657 | IAGMAELGAFFSILQ | |
| 213 | 661 | AELGAFFSILQDMRN | |
| 214 | 665 | AFFSILQDMRNTIMA | |
| 215 | 669 | ILQDMRNTIMASKTV | |
| 216 | 673 | MRNTIMASKTVGTSE | |
| 217 | 677 | IMASKTVGTSEEKLR | |
| 218 | 681 | KTVGTSEEKLRKKSS | 11 |
| 719 | 685 | TSEEKLRKKSSFYQS | |
| 770 | 689 | KLRKKSSFYQSYLRR | |
| 221 | 693 | KSSFYQSYLRRTQSM | |
| 222 | 697 | YQSYLRRTQSMGIQL | |
| 223 | 701 | LRRTQSMGIQLDQRI | |
| 224 | 705 | QSMGIQLDQRIIVLF | |

TABLE 1-continued

Peptide pools (start amino acid ("AA") numbering corresponds to the amino acid numbering in SEQ ID NO: 31)

| SEQ ID NO | Start AA | Sequence | Pool number |
|---|---|---|---|
| 225 | 709 | IQLDQRIIVLFMVAW | |
| 226 | 713 | QRIIVLFMVAWGKEA | |
| 227 | 717 | VLFMVAWGKEAVDNF | |
| 228 | 721 | VAWGKEAVDNFHLGD | |
| 229 | 725 | KEAVDNFHLGDDMDP | |
| 230 | 729 | DNFHLGDDMDPELRT | |
| 231 | 733 | LGDDMDPELRTLAQS | |
| 232 | 737 | MDPELRTLAQSLIDV | |
| 233 | 741 | LRTLAQSLIDVKVKE | |
| 234 | 745 | AQSLIDVKVKEISNQ | |
| 235 | 749 | IDVKVKEISNQEPLK | |
| 40 | 753 | DVKVKEISNQEPLKL, | |

They were applied to cells at a final concentration of 2.5 μg/ml per peptide, with 17 peptides in each of pools 1 to 10, and with 19 peptides in pool 11. Plates were developed after 18 hours at 37° C., 500 $CO_2$ in a humidified incubator. Spots were counted visually on an automated ELISPOT reader (Cellular Technologies Limited, USA). Background values from wells containing cells and medium but no peptides were subtracted and data presented as response to individual pools or summed across the target protein. Results were expressed as spot forming units (SFU) per $10^6$ cells.

The MVA-WT group and PBS group (groups 3&4) were negative when stimulated with all Hanta NP pools. In the prime/boost and prime groups, an IFN-γ response was detected to several peptide pools, and a particularly strong response was directed to 2 distinct regions of the NP (corresponding to pools 4 and 9).

The inventors found that T-cell (IFN-γ) stimulation increased greatly in respect of SEQ ID NOs: 11 and 12.

Increased responses were also detected against pools 2, 3, 5, 7, 8 and 10 for the prime/boost and prime groups compared to the control groups. Total ELISPOT responses from vaccinated and unvaccinated mice are provided in FIG. 5; and FIG. 6 shows ELISPOT responses to individual peptide pools.

To measure the antibody responses in immunised mice, ELISA analysis was undertaken to assess binding of antibodies to Hantavirus specific protein. Recombinant Hanta NP as a crude lysate (Native Antigen Company, UK) was diluted in 0.2M carbonate-bicarbonate buffer pH 9.4 (Thermo Scientific) and used to coat Maxisorp 96-well plates (Nunc, Denmark) at 10 μg/ml in 100 μl. Plates were incubated at 4° C. overnight, then washed with PBS+0.01% Tween-20 (Sigma-Aldrich) and blocked with 100 μl of 5% Milk powder (Merck, Millipore) in PBS+0.01% Tween-20 at 37° C. for 1 hour, before re-washing in PBS+0.01% Tween-20. Samples were diluted 1:50 in 5% milk powder in PBS+0.01% Tween-20 buffer, added to the plates in triplicate (100 μl per well) and incubated at 37° C. for 1 hour. Normal mouse serum (Sigma-Aldrich) and a polyclonal Anti-Hantavirus hyper immune mouse ascetic fluid sample (BEI Resources, USA) were used as positive and negative control samples respectively. Plates were washed with PBS+0.01% Tween-20 and 100 μl of a polyclonal anti-mouse HRP conjugate (Sigma-Aldrich) at a 1:20,000 dilution in 5% milk PBS+0.01% Tween-20 was added to each well. Following a further 1 hour incubation at 37° C., plates were washed with PBS+0.01% Tween-20 and 100 μl of TMB substrate (Surmodics) added to each well then incubated at 20° C. for 1 hour. The reaction was stopped by addition of 100 μl of Stop solution (Surmodics) prepared according to the manufacturer's instructions and plates read at 450 nm using a molecular devices plate reader and Softmax Pro version 5.2 software (Molecular Devices). Background absorbance values were subtracted from the sample values and results reported as Absorbance (450 nm) at a 1:50 dilution. Data was illustrated and analysed using Graph Pad Prism 7 (see FIG. 7).

The MVA-WT and the PBS control groups showed very little absorbance with values similar to those in the blank wells. The response of all mice in both the prime and the prime/boost vaccinated groups were markedly higher. The prime only group recorded an average absorbance of ~2.3 and the prime/boost an average OD of ~1.5.

Therefore, vector of the invention demonstrates highly desirable induction of cellular and humoral immune responses.

Example 3. Efficacy Testing 60 male A129 mice at a weight of 19-21 g were previously randomly divided into 4 groups prior to ear tagging and microchipping for identification, weight monitoring and temperature monitoring.

The remaining mice that were not culled on Day 28 for immunogenicity studies were challenged with Hanta SEOV on Day 28. From each group, n=10 animals were challenged via the intranasal route and n=5 animals were challenged via intramuscular route at $1.36\times10^6$ TCID50/dose.

Intramuscularly challenged animals were euthanised at day 33. Intranasally challenged mice were euthanised at day 33 (5 per group) or day 42 (5 per group). Blood, saliva, liver, kidney, lung and spleen were collected for histology and viral burden analysis. All efforts were made to minimise animal suffering. These studies were approved by the ethical review process of PHE, Porton Down, UK and the Home Office, UK via project license number 30/2993. Work was performed in accordance with the Animals (Scientific procedures) Act 1986 and the Home Office (UK) Code of Practice for the Housing and Care of Animals Used in Scientific Procedures (1989).

Clinical Signs:

Animal weights and temperatures were recorded daily throughout the study. All challenged animals remained healthy, and no clinical signs were observed following challenge with Hantavirus. Temperature and bodyweight throughout the study are reported in FIG. 8.

Viral Loads:

Viral load was assessed at 5- and 14-days post-challenge. As shown in FIG. 9, at day 5, immunisation with MVAHantaNP had achieved a reduction or complete clearance of Hantavirus from tested tissues. The highly advantageous reduction in viral load was also observed in most tissues at 14 days post-challenge.

Viral Loads—Follow-Up Study:

In a follow-up study, 28 female A129 mice were previously randomly divided into two groups prior to ear tagging and microchipping for identification, weight monitoring and temperature monitoring.

Of these 28 mice, 16 were primed with GLP-grade MVAHantaNP at Day 0 followed by a boost immunisation at Day 14 ("Group A"); and 12 mice received prime and boost immunisations with empty MVA wild-type vector at Days 0 and 14, respectively ("Group B"). Immunisations were performed according to Example 2, above.

At Day 28, 8 of the Group A mice and 8 of the Group B mice were challenged intranasally with Hanta SEOV, at a dose of $3\times10^6$ TCID50/mouse.

In this follow-study, viral load was assessed at 5-days post challenge. As shown in FIG. 10, immunisation with MVA-HantaNP achieved advantageous reduction of Hantavirus from tested tissues, even when the challenge dose was more than doubled.

Example 4: Preparation of an Example Adenovirus Vector

A non-replicating adenovirus is engineered to express Hantavirus NP nucleic acid of the invention or a fragment thereof. The genetic sequence for the Hantavirus NP is inserted into the genome of the adenovirus vector. Expression of the Hantavirus NP is indicated by reactivity between a NP-specific antibody and products from the adenovirus by Western blotting or ELISA as follows:

Cellular lysate of cells infected with the recombinant adenovirus, subjected to SDS-PAGE and Western blotting with an antibody specific for the Hanta virus NP, show a specific reactivity compared to negative controls.

Alternatively, products from cells infected with the recombinant adenovirus are used to coat an ELISA plate. Hanta virus-specific antibodies bind to the coating and are detected via a chemical reaction.

Example 5: Hanta Virus Vaccine Provides Cross-Strain Protection

A vaccine expressing Hanta virus NP nucleic acid of the invention or a fragment thereof, in an adenovirus or non-replicating poxvirus vector, is delivered via a parenteral route into mice that are susceptible to disease caused by Hanta virus. They are challenged with a lethal dose of Hanta virus, from a strain other than that on which the vaccine is based. The challenged animals show no or mild clinical signs of illness, and do not require euthanasia. Control animals which received the same challenge dose of Hanta virus, but did not receive the vaccine, show severe signs of illness, reach humane clinical endpoints and require euthanasia.

Example 6. Preparation and Efficacy of a Recombinant Influenza Virus Vector

Reverse genetics are used to construct a recombinant influenza virus that carries a protective epitope of Hanta virus NP in the neuraminidase stalk. Hanta virus-specific cytotoxic T lymphocytes (CTLs) are induced in mice after intranasal or parenteral administration. These CTLs provide a reduction in viral load and clinical illness after challenge with Hanta virus.

Example 7. Preparation and Efficacy of a Recombinant Bacterial Vector

Hanta virus NP nucleic acid of the invention or a fragment thereof, is expressed on the surface of genetically attenuated, gram-negative bacteria. After intranasal or parenteral administration to mice, the bacterial vector colonises antigen-presenting cells (e.g. dendritic cells or macrophages). A humoral and cellular Hanta virus-specific immune response is induced. These immune responses provide a reduction in viral load and clinical illness after challenge with Hanta virus.

The invention claimed is:

1. A viral vector or bacterial vector:

(A) said vector comprising:

(i) a first nucleic acid sequence comprising SEQ ID NOs: 17 or 24; and (ii) a second nucleic acid sequence selected from comprising SEQ ID NOs: 21 or 28;

and/or (B) said vector comprising a nucleic acid sequence comprising SEQ ID NO: 29 or 30;

wherein a peptide or peptides encoded by said first and second nucleic acid sequences can induce an immune response in a subject; and wherein a peptide or peptides encoded by SEQ ID NO: 29 or 30 can induce an immune response in a subject.

2. The vector of claim 1, wherein the immune response is a protective immune response.

3. The vector of claim 1, wherein the vector is a viral vector.

4. The vector of claim 3, wherein the vector is a non-replicating poxvirus vector.

5. The vector of claim 4, wherein the non-replicating poxvirus vector is a Modified Vaccinia virus Ankara (MVA) vector, a NYVAC vaccinia virus vector, a canarypox (ALVAC) vector, or a fowlpox (FPV) vector.

6. The vector of claim 4, wherein the non-replicating poxvirus vector is an MVA vector.

7. The vector of claim 4, wherein the non-replicating poxvirus vector is a fowlpox vector.

8. The vector of claim 3, wherein the vector is an adenovirus vector.

9. The vector of claim 8, wherein the adenovirus vector is a non-replicating adenovirus vector.

10. The vector of claim 8, wherein the adenovirus vector is a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector, or an Ad5 vector.

11. The vector of claim 3, wherein the vector is a measles virus vector.

12. The vector of claim 11, wherein the measles virus vector is a non-replicating measles virus vector.

13. A method of making a viral vector, comprising:

providing a nucleic acid, wherein the nucleic acid comprises a nucleic acid sequence encoding a vector according to claim 1;

transfecting a host cell with the nucleic acid;

culturing the host cell under conditions suitable for the propagation of the vector; and obtaining the vector from the host cell.

14. A host cell comprising a vector according to claim 1.

15. A composition comprising a vector according to claim 1, and a pharmaceutically-acceptable carrier.

16. The composition of claim 15, further comprising an adjuvant.

17. A method of treating a subject in need thereof, comprising administering an effective amount of the vector according to claim 1 or a composition comprising the vector and a pharmaceutically-acceptable carrier.

18. A method of inducing an immune response in a subject, comprising administering to the subject an effective amount of the vector according to claim 1 or a composition comprising the vector and a pharmaceutically-acceptable carrier.

19. The method of claim 18, wherein the immune response comprises a T cell response.

20. A method of preventing or treating a Hantavirus infection in a subject, comprising administering to the subject an effective amount of the vector according to claim 1 or a composition comprising the vector and a pharmaceutically-acceptable carrier.

21. A method of preventing or treating hemorrhagic fever with renal syndrome in a subject, comprising administering to the subject an effective amount of the vector according to claim 1 or a composition comprising the vector and a pharmaceutically-acceptable carrier.

* * * * *

SEQUENCE LISTING

```
<160> NUMBER OF SEQ ID NOS: 235

<210> SEQ ID NO 1
<211> LENGTH: 1768
<212> TYPE: DNA
<213> ORGANISM: Seoul virus

<400> SEQUENCE: 1

tagtagtagg ctccctaaag agctactaca ctaacaagga aaatggcaac tatggaagaa      60

atccagagag aaatcagtgc gcacgagggg cagcttgtaa tagcacgcca gaaggtcaag     120

gatgcagaaa agcagtatga gaaggatcct gatgacctaa ataagagggc actgcatgat     180

cgggagagtg tcgcagcttc aatacaatca aaaattgatg aattgaagcg ccaacttgct     240

gacaggattg cagcagggaa gaacatcggg caagaccggg atcctacagg ggtagagccg     300

ggtgatcatc tcaaggaaag atcagcacta agctacggga atacactgga cctgaatagc     360

cttgacattg atgaacctac aggacagaca gctgattggt tgaccataat tgtctatttg     420

acatcattcg tggtcccgat catcttgaag gcactgtaca tgttgacaac aagaggcagg     480

cagacttcaa aggacaacaa gggaatgagg atcagattca aggatgacag ctcatatgaa     540

gatgtcaatg gaatcagaaa gcccaaacat ctgtatgtgt caatgccaaa cgcccaatca     600

agcatgaagg ctgaagagat aacacctgga agattccgca ctgcagtatg tgggctatac     660

cctgcacaga taaaggcaag gaacatggta agccctgtca tgagtgtagt tgggtttttg     720

gcactggcaa aagactggac atctagaatt gaagaatggc ttggtgcacc ctgcaagttc     780

atggcagagt ctcccattgc cgggagctta tctgggaatc ctgtgaatcg tgattatatc     840
```

agacagagac aaggtgcact tgcagggatg gagccaaaag aatttcaagc tctcaggcaa 900
cattcaaagg atgctggatg tacactggtt gaacatattg agtcaccatc atcaatatgg 960
gtatttgctg ggcccctga taggtgccca ccgacatgcc tgtttgttgg agggatggct 1020
gagttaggtg ctttcttttc tatacttcag gatatgagga acacaatcat ggcttcaaag 1080
actgtgggaa cagctgatga aaagcttcga aagaagtcat cattctatca atcatacctc 1140
agacgcacac aatcaatggg aatacaactg gaccagagga taattgttat gtttatggtt 1200
gcctggggaa aggaggcagt ggacaacttt catctcggtg atgacatgga tccagagctt 1260
cgcagcctgg ctcagatcct gattgaccag aaagtgaagg aaatctcaaa ccaggaacct 1320
atgaaattat aagtacataa ttatgtaatc catactaact ataggttaag aaatactaat 1380
cattagttaa taagaatata gatttattga ataatcatat taaataatta ggtaagttaa 1440
ctattagtta gttaagttag ctaattgatt tatatgatta tcacaattga atgtaatcat 1500
aagcacaatc actgccatgt ataatcacgg gtatacgggt ggttttcata tggggaacag 1560
ggtgggctta gggccaggtc accttaagtg accttttttg tatatatgga tgtagatttc 1620
aattgatcga gtactaatcc tactgttctc ttttcctttc ctttctcctt ctttactaac 1680
aacaacaaac tacctcacaa ccttctacct caacacatac tacctcattc agttgtttcc 1740
ttttgtcttt ttagggagca tactacta 1768

<210> SEQ ID NO 2
<211> LENGTH: 1287
<212> TYPE: DNA
<213> ORGANISM: Seoul virus

<400> SEQUENCE: 2
atggcaacta tggaagaaat ccagagagaa atcagtgcgc acgaggggca gcttgtaata 60
gcacgccaga aggtcaagga tgcagaaaag cagtatgaga aggatcctga tgacctaaat 120
aagagggcac tgcatgatcg ggagagtgtc gcagcttcaa tacaatcaaa aattgatgaa 180
ttgaagcgcc aacttgctga caggattgca gcagggaaga acatcgggca agaccgggat 240
cctacagggg tagagccggg tgatcatctc aaggaaagat cagcactaag ctacgggaat 300
acactggacc tgaatagcct tgacattgat gaacctacag gacagacagc tgattggttg 360
accataattg tctatttgac atcattcgtg gtcccgatca tcttgaaggc actgtacatg 420
ttgacaacaa gaggcaggca gacttcaaag gacaacaagg gaatgaggat cagattcaag 480
gatgacagct catatgaaga tgtcaatgga atcagaaagc ccaaacatct gtatgtgtca 540
atgccaaacg cccaatcaag catgaaggct gaagagataa cacctggaag attccgcact 600
gcagtatgtg ggctataccc tgcacagata aaggcaagga acatggtaag ccctgtcatg 660
agtgtagttg ggtttttggc actggcaaaa gactggacat ctagaattga agaatggctt 720
ggtgcaccct gcaagttcat ggcagagtct cccattgccg ggagcttatc tgggaatcct 780
gtgaatcgtg attatatcag acagagacaa ggtgcacttg cagggatgga gccaaaagaa 840
tttcaagctc tcaggcaaca ttcaaaggat gctggatgta cactggttga acatattgag 900
tcaccatcat caatatgggt atttgctggg gcccctgata ggtgcccacc gacatgcctg 960
tttgttggag ggatggctga gttaggtgct ttcttttcta tacttcagga tatgaggaac 1020
acaatcatgg cttcaaagac tgtgggaaca gctgatgaaa agcttcgaaa gaagtcatca 1080
ttctatcaat catacctcag acgcacacaa tcaatgggaa tacaactgga ccagaggata 1140
attgttatgt ttatggttgc ctggggaaag gaggcagtgg acaactttca tctcggtgat 1200
gacatggatc cagagcttcg cagcctggct cagatcctga ttgaccagaa agtgaaggaa 1260
atctcaaacc aggaacctat gaaatta 1287

<210> SEQ ID NO 3
<211> LENGTH: 1287
<212> TYPE: DNA
<213> ORGANISM: Artificial
<220> FEATURE:
<223> OTHER INFORMATION: Codon optimised

<400> SEQUENCE: 3
atggccacaa tggaagagat ccagagagag atcagcgccc acgagggaca gctggttatc 60
gccagacaga aagtgaagga cgccgagaag cagtacgaga aggaccccga cgatctgaac 120
aagagagccc tgcacgacag agaaagcgtg gccgcctcta tccagagcaa gatcgatgag 180
ctgaagagac agctggccga cagaatcgcc gctggcaaga atattggcca ggacagagat 240
cccacaggcg tggaacctgg cgatcacctg aaagagagaa gcgccctgtc ctatggcaac 300
accctggacc tgaacagcct ggacattgat gagcctaccg gccagacagc cgactggctg 360
acaatcattg tgtacctgac cagcttcgtg gtccccatca tcctgaaggc cctgtacatg 420
ctgaccacca gaggcagaca gaccagcaag gacaacaagg gcatgagaat ccggttcaag 480
gatgacagca gctacgagga cgtgaacggc attagaaagc ccaagcacct gtacgtgtcc 540
atgcctaacg ctcagagcag catgaaggcc gaggaaatca cccctggcag attcagaaca 600
gccgtgtgcg gactgtaccc cgctcagatc aaggccagaa acatggtgtc cccagtgatg 660
agcgtcgtgg gatttctggc cctggctaag gactggacca gcaggattga ggaatggctg 720
ggagcccctt gcaagtttat ggccgagtct cctatcgccg gcagcctgtc tggcaacccc 780
gtgaatagag actacatcag acagaggcag ggcgctctgg ccggaatgga acccaaagaa 840
tttcaggccc tgcggcagca ctctaaggat gccggatgta ccctggtgga acacattgag 900
agccccagca gcatctgggt tttcgctggc gctcctgata gatgccctcc tacctgtctg 960
tttgttggcg gaatggccga gctgggcgcc ttctttagca ttctgcagga catgcggaat 1020
accatcatgg ccagcaagac cgtgggcacc gccgatgaga agctgagaaa gaagtccagc 1080
ttctaccaga gctacctgcg gagaacccag agcatgggca ttcagctgga ccagagaatc 1140
atcgtgatgt tcatggtggc ctggggcaaa gaagccgtgg acaattttca cctgggcgac 1200
gacatggacc ccgagctgag atctctggcc cagatcctga tcgaccagaa agtcaaagag 1260
atctccaatc aagagcccat gaagctg 1287

<210> SEQ ID NO 4
<211> LENGTH: 429
<212> TYPE: PRT
<213> ORGANISM: Seoul virus

<400> SEQUENCE: 4

Met Ala Thr Met Glu Glu Ile Gln Arg Glu Ile Ser Ala His Glu Gly
1 5 10 15

Gln Leu Val Ile Ala Arg Gln Lys Val Lys Asp Ala Glu Lys Gln Tyr
20 25 30

Glu Lys Asp Pro Asp Asp Leu Asn Lys Arg Ala Leu His Asp Arg Glu
35 40 45

Ser Val Ala Ala Ser Ile Gln Ser Lys Ile Asp Glu Leu Lys Arg Gln
50 55 60

```
Leu Ala Asp Arg Ile Ala Ala Gly Lys Asn Ile Gly Gln Asp Arg Asp
65                  70                  75                  80

Pro Thr Gly Val Glu Pro Gly Asp His Leu Lys Glu Arg Ser Ala Leu
                85                  90                  95

Ser Tyr Gly Asn Thr Leu Asp Leu Asn Ser Leu Asp Ile Asp Glu Pro
            100                 105                 110

Thr Gly Gln Thr Ala Asp Trp Leu Thr Ile Ile Val Tyr Leu Thr Ser
        115                 120                 125

Phe Val Val Pro Ile Ile Leu Lys Ala Leu Tyr Met Leu Thr Thr Arg
    130                 135                 140

Gly Arg Gln Thr Ser Lys Asp Asn Lys Gly Met Arg Ile Arg Phe Lys
145                 150                 155                 160

Asp Asp Ser Ser Tyr Glu Asp Val Asn Gly Ile Arg Lys Pro Lys His
                165                 170                 175

Leu Tyr Val Ser Met Pro Asn Ala Gln Ser Ser Met Lys Ala Glu Glu
            180                 185                 190

Ile Thr Pro Gly Arg Phe Arg Thr Ala Val Cys Gly Leu Tyr Pro Ala
        195                 200                 205

Gln Ile Lys Ala Arg Asn Met Val Ser Pro Val Met Ser Val Val Gly
    210                 215                 220

Phe Leu Ala Leu Ala Lys Asp Trp Thr Ser Arg Ile Glu Glu Trp Leu
225                 230                 235                 240

Gly Ala Pro Cys Lys Phe Met Ala Glu Ser Pro Ile Ala Gly Ser Leu
                245                 250                 255

Ser Gly Asn Pro Val Asn Arg Asp Tyr Ile Arg Gln Arg Gln Gly Ala
            260                 265                 270

Leu Ala Gly Met Glu Pro Lys Glu Phe Gln Ala Leu Arg Gln His Ser
        275                 280                 285

Lys Asp Ala Gly Cys Thr Leu Val Glu His Ile Glu Ser Pro Ser Ser
    290                 295                 300

Ile Trp Val Phe Ala Gly Ala Pro Asp Arg Cys Pro Pro Thr Cys Leu
305                 310                 315                 320

Phe Val Gly Gly Met Ala Glu Leu Gly Ala Phe Phe Ser Ile Leu Gln
                325                 330                 335

Asp Met Arg Asn Thr Ile Met Ala Ser Lys Thr Val Gly Thr Ala Asp
            340                 345                 350

Glu Lys Leu Arg Lys Lys Ser Ser Phe Tyr Gln Ser Tyr Leu Arg Arg
        355                 360                 365

Thr Gln Ser Met Gly Ile Gln Leu Asp Gln Arg Ile Ile Val Met Phe
    370                 375                 380

Met Val Ala Trp Gly Lys Glu Ala Val Asp Asn Phe His Leu Gly Asp
385                 390                 395                 400

Asp Met Asp Pro Glu Leu Arg Ser Leu Ala Gln Ile Leu Ile Asp Gln
                405                 410                 415

Lys Val Lys Glu Ile Ser Asn Gln Glu Pro Met Lys Leu
            420                 425
```

<210> SEQ ID NO 5
<211> LENGTH: 1698
<212> TYPE: DNA
<213> ORGANISM: Hantaan virus

<400> SEQUENCE: 5

```
tagtagtaga ctccctaaag agctactaga acaacgatgg caactatgga ggaattgcag      60
```

agggaaatca atgcccatga gggtcaactg gtgatagcca ggcagaaggt gagggatgca 120
gaaaagcagt atgaaaagga tccagatgag ttaaacaaga gagcattgac agatcgagag 180
ggtgttgcag tatccattca agcaaagatt gatgagttaa agaggcaatt ggcagatagg 240
attgcaaccg ggaagaacct tggaaaggaa caagacccaa caggggtaga acctggagat 300
catctgaaag agagatcaat gctcagttat ggaaatgttc ttgacttaaa ccacctggat 360
attgatgagc caacaggaca gacagcagac tggctgggca ttgttatcta tctcacatcc 420
tttgttgtcc cgatacttct gaaagccctg tacatgttaa caacaagagg gaggcagacc 480
accaaggaca ataaaggaac tcggattcga ttcaaggatg atagctcctt cgaggatgtc 540
aatggcattc ggaagccgaa acatctatat gtgtccttac caaatgcaca gtcaagtatg 600
aaagcagaag agattacacc tggtagatat agaacagcaa tttgtggact ttaccctgca 660
caaattaagg caagacagat gattagtcca gtcatgagtg taatcggatt cttggctttg 720
gcaaaagatt ggagtgaccg cattgagcag tggttaagtg aaccgtgtaa gcttcttcca 780
gatacagcag cagttagcct tcttggtggt cctgcaacca acagggacta tttacggcag 840
cgacaagtag cattgggcaa catggaaaca aaagagtcta aggctatacg ccaacatgca 900
gaagcagcag gctgtagtat gattgaggac attgagtcac catcatcaat atgggtgttt 960
gctggggcac cggaccgctg tccaccaaca tgtctcttta ttgcaggtat ggctgagctt 1020
ggggcatttt tttccatcct gcaggacatg cgaaatacaa ttatggcatc caagacagtt 1080
ggaacctctg aggagaagct acggaagaaa tcctcattct atcagtctta tctcaggaga 1140
acacaatcaa tgggaataca actggatcag aggataattg tgctcttcat ggtagcctgg 1200
gggaaagaag cagtggataa cttccaccta ggagatgata tggaccctga gctgcgaaca 1260
ctagcacaga gcctgattga tgttaaagtg aaggaaattt ccaaccaaga gcctttaaaa 1320
ctataatcag tgaatgtata accctcatta tgtgattatt atatactact gaatcattat 1380
caatcatatt tgcactatta ttatcagggg aattagtata tcagggtaag ggcacattta 1440
tgggtgggaa tcattactca gagggtgggt cagttaatcc gttgtgggtg ggtttagttc 1500
ctggctgcct taagtagcct ttttttgtat atatggatgt agatttcatt tgatctttaa 1560
actaatcttg ctctttttcc ttttcctcct gctttctctg cttactaaca acaacattct 1620
acctcaacac acaactacct caactaaact acctcatttg attgctcctt gattgtctct 1680
ttagggagtc tactacta 1698

<210> SEQ ID NO 6
<211> LENGTH: 1287
<212> TYPE: DNA
<213> ORGANISM: Hantaan virus

<400> SEQUENCE: 6
atggcaacta tggaggaatt gcagagggaa atcaatgccc atgagggtca actggtgata 60
gccaggcaga aggtgaggga tgcagaaaag cagtatgaaa aggatccaga tgagttaaac 120
aagagagcat tgacagatcg agagggtgtt gcagtatcca ttcaagcaaa gattgatgag 180
ttaaagaggc aattggcaga taggattgca accgggaaga accttggaaa ggaacaagac 240
ccaacagggg tagaacctgg agatcatctg aaagagagat caatgctcag ttatggaaat 300
gttcttgact taaaccacct ggatattgat gagccaacag gacagacagc agactggctg 360
ggcattgtta tctatctcac atcctttgtt gtcccgatac ttctgaaagc cctgtacatg 420
ttaacaacaa gagggaggca gaccaccaag gacaataaag gaactcggat tcgattcaag 480

```
gatgatagct ccttcgagga tgtcaatggc attcggaagc cgaaacatct atatgtgtcc    540

ttaccaaatg cacagtcaag tatgaaagca gaagagatta cacctggtag atatagaaca    600

gcaatttgtg gactttaccc tgcacaaatt aaggcaagac agatgattag tccagtcatg    660

agtgtaatcg gattcttggc tttggcaaaa gattggagtg accgcattga gcagtggtta    720

agtgaaccgt gtaagcttct tccagataca gcagcagtta gccttcttgg tggtcctgca    780

accaacaggg actatttacg gcagcgacaa gtagcattgg gcaacatgga aacaaaagag    840

tctaaggcta tacgccaaca tgcagaagca gcaggctgta gtatgattga ggacattgag    900

tcaccatcat caatatgggt gtttgctggg gcaccggacc gctgtccacc aacatgtctc    960

tttattgcag gtatggctga gcttggggca tttttttcca tcctgcagga catgcgaaat   1020

acaattatgg catccaagac agttggaacc tctgaggaga agctacggaa gaaatcctca   1080

ttctatcagt cttatctcag gagaacacaa tcaatgggaa tacaactgga tcagaggata   1140

attgtgctct tcatggtagc ctgggggaaa gaagcagtgg ataacttcca cctaggagat   1200

gatatggacc ctgagctgcg aacactagca cagagcctga ttgatgttaa agtgaaggaa   1260

atttccaacc aagagccttt aaaacta                                      1287


<210> SEQ ID NO 7
<211> LENGTH: 429
<212> TYPE: PRT
<213> ORGANISM: Hantaan virus

<400> SEQUENCE: 7

Met Ala Thr Met Glu Glu Leu Gln Arg Glu Ile Asn Ala His Glu Gly
1               5                   10                  15

Gln Leu Val Ile Ala Arg Gln Lys Val Arg Asp Ala Glu Lys Gln Tyr
            20                  25                  30

Glu Lys Asp Pro Asp Glu Leu Asn Lys Arg Ala Leu Thr Asp Arg Glu
        35                  40                  45

Gly Val Ala Val Ser Ile Gln Ala Lys Ile Asp Glu Leu Lys Arg Gln
    50                  55                  60

Leu Ala Asp Arg Ile Ala Thr Gly Lys Asn Leu Gly Lys Glu Gln Asp
65                  70                  75                  80

Pro Thr Gly Val Glu Pro Gly Asp His Leu Lys Glu Arg Ser Met Leu
                85                  90                  95

Ser Tyr Gly Asn Val Leu Asp Leu Asn His Leu Asp Ile Asp Glu Pro
            100                 105                 110

Thr Gly Gln Thr Ala Asp Trp Leu Gly Ile Val Ile Tyr Leu Thr Ser
        115                 120                 125

Phe Val Val Pro Ile Leu Leu Lys Ala Leu Tyr Met Leu Thr Thr Arg
    130                 135                 140

Gly Arg Gln Thr Thr Lys Asp Asn Lys Gly Thr Arg Ile Arg Phe Lys
145                 150                 155                 160

Asp Asp Ser Ser Phe Glu Asp Val Asn Gly Ile Arg Lys Pro Lys His
                165                 170                 175

Leu Tyr Val Ser Leu Pro Asn Ala Gln Ser Ser Met Lys Ala Glu Glu
            180                 185                 190

Ile Thr Pro Gly Arg Tyr Arg Thr Ala Ile Cys Gly Leu Tyr Pro Ala
        195                 200                 205

Gln Ile Lys Ala Arg Gln Met Ile Ser Pro Val Met Ser Val Ile Gly
    210                 215                 220
```

```
Phe Leu Ala Leu Ala Lys Asp Trp Ser Asp Arg Ile Glu Gln Trp Leu
225                 230                 235                 240

Ser Glu Pro Cys Lys Leu Leu Pro Asp Thr Ala Ala Val Ser Leu Leu
                245                 250                 255

Gly Gly Pro Ala Thr Asn Arg Asp Tyr Leu Arg Gln Arg Gln Val Ala
            260                 265                 270

Leu Gly Asn Met Glu Thr Lys Glu Ser Lys Ala Ile Arg Gln His Ala
        275                 280                 285

Glu Ala Ala Gly Cys Ser Met Ile Glu Asp Ile Glu Ser Pro Ser Ser
    290                 295                 300

Ile Trp Val Phe Ala Gly Ala Pro Asp Arg Cys Pro Pro Thr Cys Leu
305                 310                 315                 320

Phe Ile Ala Gly Met Ala Glu Leu Gly Ala Phe Phe Ser Ile Leu Gln
                325                 330                 335

Asp Met Arg Asn Thr Ile Met Ala Ser Lys Thr Val Gly Thr Ser Glu
            340                 345                 350

Glu Lys Leu Arg Lys Lys Ser Ser Phe Tyr Gln Ser Tyr Leu Arg Arg
        355                 360                 365

Thr Gln Ser Met Gly Ile Gln Leu Asp Gln Arg Ile Ile Val Leu Phe
    370                 375                 380

Met Val Ala Trp Gly Lys Glu Ala Val Asp Asn Phe His Leu Gly Asp
385                 390                 395                 400

Asp Met Asp Pro Glu Leu Arg Thr Leu Ala Gln Ser Leu Ile Asp Val
                405                 410                 415

Lys Val Lys Glu Ile Ser Asn Gln Glu Pro Leu Lys Leu
            420                 425


<210> SEQ ID NO 8
<211> LENGTH: 1005
<212> TYPE: DNA
<213> ORGANISM: Hantaan virus

<400> SEQUENCE: 8

atgctcagtt atggaaatgt tcttgactta aaccacctgg atattgatga gccaacagga     60

cagacagcag actggctggg cattgttatc tatctcacat cctttgttgt cccgatactt    120

ctgaaagccc tgtacatgtt aacaacaaga gggaggcaga ccaccaagga caataaagga    180

actcggattc gattcaagga tgatagctcc ttcgaggatg tcaatggcat tcggaagccg    240

aaacatctat atgtgtcctt accaaatgca cagtcaagta tgaaagcaga agagattaca    300

cctggtagat atagaacagc aatttgtgga ctttaccctg cacaaattaa ggcaagacag    360

atgattagtc cagtcatgag tgtaatcgga ttcttggctt tggcaaaaga ttggagtgac    420

cgcattgagc agtggttaag tgaaccgtgt aagcttcttc cagatacagc agcagttagc    480

cttcttggtg gtcctgcaac caacagggac tatttacggc agcgacaagt agcattgggc    540

aacatggaaa caaaagagtc taaggctata cgccaacatg cagaagcagc aggctgtagt    600

atgattgagg acattgagtc accatcatca atatgggtgt ttgctggggc accggaccgc    660

tgtccaccaa catgtctctt tattgcaggt atggctgagc ttggggcatt tttttccatc    720

ctgcaggaca tgcgaaatac aattatggca tccaagacag ttggaacctc tgaggagaag    780

ctacggaaga aatcctcatt ctatcagtct tatctcagga gaacacaatc aatgggaata    840

caactggatc agaggataat tgtgctcttc atggtagcct gggggaaaga agcagtggat    900

aacttccacc taggagatga tatggaccct gagctgcgaa cactagcaca gagcctgatt    960
```

gatgttaaag tgaaggaaat ttccaaccaa gagcctttaa aacta 1005

<210> SEQ ID NO 9
<211> LENGTH: 1005
<212> TYPE: DNA
<213> ORGANISM: Artificial
<220> FEATURE:
<223> OTHER INFORMATION: Codon optimised

<400> SEQUENCE: 9
atgctgagct acggcaacgt gctggatctg aaccacctgg atatcgacga gccaacagga 60
cagaccgctg attggctggg catcgtgatc tacctgacct cctttgtggt gcctattctg 120
ctcaaagccc tctatatgct gacaacacgc ggaaggcaga ccaccaaaga taacaaaggc 180
acccggatca ggtttaagga cgacagctcc tttgaggatg tcaacggcat ccggaaacct 240
aagcacctct atgtgtctct gcccaatgca cagtcctcca tgaaggcaga agagatcaca 300
ccaggccggt acagaaccgc catctgtgga ctgtatcctg cacaaatcaa agcccggcag 360
atgatcagcc ccgtgatgtc cgttatcgga ttcctggctc tggccaaaga ttggagcgac 420
aggatcgagc agtggctgag cgagccttgc aagctgcttc ctgatacagc cgctgtgtca 480
ctgcttggcg gccctgccac aaacagagat tacctgagac agagacaggt ggcactgggc 540
aacatggaaa caaaagagag caaggccatc cggcagcatg ccgaagctgc tggctgtagc 600
atgatcgagg atatcgagtc ccctagctcc atttgggtgt tcgcaggggc cccagataga 660
tgtccaccaa catgcctgtt cattgccggc atggctgaac tgggagcttt tttcagcatc 720
ctccaggata tgcgcaacac gattatggcc tccaagacag tgggaaccag cgaggaaaag 780
ctgcggaaga aaagcagctt ttaccagtct tacctgaggc ggacccagtc catggggatc 840
caactggatc agcggatcat tgtgctgttt atggtcgctt ggggaaaaga ggctgtcgat 900
aacttccacc tgggagatga tatggatcct gaactgcgga ccctggctca gtccctgatc 960
gatgtgaaag tgaaagaaat tagtaatcaa gaacccctca agctg 1005

<210> SEQ ID NO 10
<211> LENGTH: 335
<212> TYPE: PRT
<213> ORGANISM: Hantaan virus

<400> SEQUENCE: 10

Met Leu Ser Tyr Gly Asn Val Leu Asp Leu Asn His Leu Asp Ile Asp
1 5 10 15

Glu Pro Thr Gly Gln Thr Ala Asp Trp Leu Gly Ile Val Ile Tyr Leu
20 25 30

Thr Ser Phe Val Val Pro Ile Leu Leu Lys Ala Leu Tyr Met Leu Thr
35 40 45

Thr Arg Gly Arg Gln Thr Thr Lys Asp Asn Lys Gly Thr Arg Ile Arg
50 55 60

Phe Lys Asp Asp Ser Ser Phe Glu Asp Val Asn Gly Ile Arg Lys Pro
65 70 75 80

Lys His Leu Tyr Val Ser Leu Pro Asn Ala Gln Ser Ser Met Lys Ala
85 90 95

Glu Glu Ile Thr Pro Gly Arg Tyr Arg Thr Ala Ile Cys Gly Leu Tyr
100 105 110

Pro Ala Gln Ile Lys Ala Arg Gln Met Ile Ser Pro Val Met Ser Val
115 120 125

Ile Gly Phe Leu Ala Leu Ala Lys Asp Trp Ser Asp Arg Ile Glu Gln

```
    130                 135                 140

Trp Leu Ser Glu Pro Cys Lys Leu Leu Pro Asp Thr Ala Ala Val Ser
145                 150                 155                 160

Leu Leu Gly Gly Pro Ala Thr Asn Arg Asp Tyr Leu Arg Gln Arg Gln
                165                 170                 175

Val Ala Leu Gly Asn Met Glu Thr Lys Glu Ser Lys Ala Ile Arg Gln
            180                 185                 190

His Ala Glu Ala Ala Gly Cys Ser Met Ile Glu Asp Ile Glu Ser Pro
        195                 200                 205

Ser Ser Ile Trp Val Phe Ala Gly Ala Pro Asp Arg Cys Pro Pro Thr
    210                 215                 220

Cys Leu Phe Ile Ala Gly Met Ala Glu Leu Gly Ala Phe Phe Ser Ile
225                 230                 235                 240

Leu Gln Asp Met Arg Asn Thr Ile Met Ala Ser Lys Thr Val Gly Thr
                245                 250                 255

Ser Glu Glu Lys Leu Arg Lys Lys Ser Ser Phe Tyr Gln Ser Tyr Leu
            260                 265                 270

Arg Arg Thr Gln Ser Met Gly Ile Gln Leu Asp Gln Arg Ile Ile Val
        275                 280                 285

Leu Phe Met Val Ala Trp Gly Lys Glu Ala Val Asp Asn Phe His Leu
    290                 295                 300

Gly Asp Asp Met Asp Pro Glu Leu Arg Thr Leu Ala Gln Ser Leu Ile
305                 310                 315                 320

Asp Val Lys Val Lys Glu Ile Ser Asn Gln Glu Pro Leu Lys Leu
                325                 330                 335


<210> SEQ ID NO 11
<211> LENGTH: 79
<212> TYPE: PRT
<213> ORGANISM: Artificial
<220> FEATURE:
<223> OTHER INFORMATION: Peptide pool 4

<400> SEQUENCE: 11

Leu Tyr Pro Ala Gln Ile Lys Ala Arg Asn Met Val Ser Pro Val Met
1               5                   10                  15

Ser Val Val Gly Phe Leu Ala Leu Ala Lys Asp Trp Thr Ser Arg Ile
            20                  25                  30

Glu Glu Trp Leu Gly Ala Pro Cys Lys Phe Met Ala Glu Ser Pro Ile
        35                  40                  45

Ala Gly Ser Leu Ser Gly Asn Pro Val Asn Arg Asp Tyr Ile Arg Gln
    50                  55                  60

Arg Gln Gly Ala Leu Ala Gly Met Glu Pro Lys Glu Phe Gln Ala
65                  70                  75


<210> SEQ ID NO 12
<211> LENGTH: 79
<212> TYPE: PRT
<213> ORGANISM: Artificial
<220> FEATURE:
<223> OTHER INFORMATION: Peptide pool 9

<400> SEQUENCE: 12

Ile Lys Ala Arg Gln Met Ile Ser Pro Val Met Ser Val Ile Gly Phe
1               5                   10                  15

Leu Ala Leu Ala Lys Asp Trp Ser Asp Arg Ile Glu Gln Trp Leu Ser
            20                  25                  30
```

-continued

```
Glu Pro Cys Lys Leu Leu Pro Asp Thr Ala Ala Val Ser Leu Leu Gly
        35                  40                  45

Gly Pro Ala Thr Asn Arg Asp Tyr Leu Arg Gln Arg Gln Val Ala Leu
    50                  55                  60

Gly Asn Met Glu Thr Lys Glu Ser Lys Ala Ile Arg Gln His Ala
65                  70                  75


<210> SEQ ID NO 13
<211> LENGTH: 15
<212> TYPE: PRT
<213> ORGANISM: Artificial
<220> FEATURE:
<223> OTHER INFORMATION: Peptide pool sub-region

<400> SEQUENCE: 13

Ser Pro Val Met Ser Val Val Gly Phe Leu Ala Leu Ala Lys Asp
1               5                   10                  15


<210> SEQ ID NO 14
<211> LENGTH: 15
<212> TYPE: PRT
<213> ORGANISM: Artificial
<220> FEATURE:
<223> OTHER INFORMATION: Peptide pool sub-region

<400> SEQUENCE: 14

Pro Val Met Ser Val Ile Gly Phe Leu Ala Leu Ala Lys Asp Trp
1               5                   10                  15


<210> SEQ ID NO 15
<211> LENGTH: 237
<212> TYPE: DNA
<213> ORGANISM: Seoul virus

<400> SEQUENCE: 15

ctataccctg cacagataaa ggcaaggaac atggtaagcc ctgtcatgag tgtagttggg      60

tttttggcac tggcaaaaga ctggacatct agaattgaag aatggcttgg tgcaccctgc     120

aagttcatgg cagagtctcc cattgccggg agcttatctg ggaatcctgt gaatcgtgat     180

tatatcagac agagacaagg tgcacttgca gggatggagc caaaagaatt tcaagct        237


<210> SEQ ID NO 16
<211> LENGTH: 237
<212> TYPE: DNA
<213> ORGANISM: Seoul virus

<400> SEQUENCE: 16

ctataccctg cacagataaa ggcaaggaac atggtaagcc ctgtcatgag tgtagttggg      60

tttttggcac tggcaaaaga ctggacatct agaattgaag aatggcttgg tgcaccctgc     120

aagttcatgg cagagtctcc cattgccggg agcttatctg ggaatcctgt gaatcgtgat     180

tatatcagac agagacaagg tgcacttgca gggatggagc caaaagaatt tcaagct        237


<210> SEQ ID NO 17
<211> LENGTH: 237
<212> TYPE: DNA
<213> ORGANISM: Artificial
<220> FEATURE:
<223> OTHER INFORMATION: Codon optimised

<400> SEQUENCE: 17

ctgtaccccg ctcagatcaa ggccagaaac atggtgtccc cagtgatgag cgtcgtggga      60
```

tttctggccc tggctaagga ctggaccagc aggattgagg aatggctggg agccccttgc 120
aagtttatgg ccgagtctcc tatcgccggc agcctgtctg gcaaccccgt gaatagagac 180
tacatcagac agaggcaggg cgctctggcc ggaatggaac ccaaagaatt tcaggcc 237

<210> SEQ ID NO 18
<211> LENGTH: 237
<212> TYPE: DNA
<213> ORGANISM: Hantaan virus

<400> SEQUENCE: 18
attaaggcaa gacagatgat tagtccagtc atgagtgtaa tcggattctt ggctttggca 60
aaagattgga gtgaccgcat tgagcagtgg ttaagtgaac cgtgtaagct tcttccagat 120
acagcagcag ttagccttct tggtggtcct gcaaccaaca gggactattt acggcagcga 180
caagtagcat tgggcaacat ggaaacaaaa gagtctaagg ctatacgcca acatgca 237

<210> SEQ ID NO 19
<211> LENGTH: 237
<212> TYPE: DNA
<213> ORGANISM: Hantaan virus

<400> SEQUENCE: 19
attaaggcaa gacagatgat tagtccagtc atgagtgtaa tcggattctt ggctttggca 60
aaagattgga gtgaccgcat tgagcagtgg ttaagtgaac cgtgtaagct tcttccagat 120
acagcagcag ttagccttct tggtggtcct gcaaccaaca gggactattt acggcagcga 180
caagtagcat tgggcaacat ggaaacaaaa gagtctaagg ctatacgcca acatgca 237

<210> SEQ ID NO 20
<211> LENGTH: 237
<212> TYPE: DNA
<213> ORGANISM: Hantaan virus

<400> SEQUENCE: 20
attaaggcaa gacagatgat tagtccagtc atgagtgtaa tcggattctt ggctttggca 60
aaagattgga gtgaccgcat tgagcagtgg ttaagtgaac cgtgtaagct tcttccagat 120
acagcagcag ttagccttct tggtggtcct gcaaccaaca gggactattt acggcagcga 180
caagtagcat tgggcaacat ggaaacaaaa gagtctaagg ctatacgcca acatgca 237

<210> SEQ ID NO 21
<211> LENGTH: 237
<212> TYPE: DNA
<213> ORGANISM: Artificial
<220> FEATURE:
<223> OTHER INFORMATION: Codon optimised

<400> SEQUENCE: 21
atcaaagccc ggcagatgat cagccccgtg atgtccgtta tcggattcct ggctctggcc 60
aaagattgga gcgacaggat cgagcagtgg ctgagcgagc cttgcaagct gcttcctgat 120
acagccgctg tgtcactgct tggcggccct gccacaaaca gagattacct gagacagaga 180
caggtggcac tgggcaacat ggaaacaaaa gagagcaagg ccatccggca gcatgcc 237

<210> SEQ ID NO 22
<211> LENGTH: 45
<212> TYPE: DNA
<213> ORGANISM: Seoul virus

<400> SEQUENCE: 22
agccctgtca tgagtgtagt tgggtttttg gcactggcaa aagac 45

<210> SEQ ID NO 23
<211> LENGTH: 45
<212> TYPE: DNA
<213> ORGANISM: Seoul virus

<400> SEQUENCE: 23
agccctgtca tgagtgtagt tgggtttttg gcactggcaa aagac 45

<210> SEQ ID NO 24
<211> LENGTH: 45
<212> TYPE: DNA
<213> ORGANISM: Artificial
<220> FEATURE:
<223> OTHER INFORMATION: Codon optimised

<400> SEQUENCE: 24
tccccagtga tgagcgtcgt gggatttctg gccctggcta aggac 45

<210> SEQ ID NO 25
<211> LENGTH: 45
<212> TYPE: DNA
<213> ORGANISM: Hantaan virus

<400> SEQUENCE: 25
ccagtcatga gtgtaatcgg attcttggct ttggcaaaag attgg 45

<210> SEQ ID NO 26
<211> LENGTH: 45
<212> TYPE: DNA
<213> ORGANISM: Hantaan virus

<400> SEQUENCE: 26
ccagtcatga gtgtaatcgg attcttggct ttggcaaaag attgg 45

<210> SEQ ID NO 27
<211> LENGTH: 45
<212> TYPE: DNA
<213> ORGANISM: Hantaan virus

<400> SEQUENCE: 27
ccagtcatga gtgtaatcgg attcttggct ttggcaaaag attgg 45

<210> SEQ ID NO 28
<211> LENGTH: 45
<212> TYPE: DNA
<213> ORGANISM: Artificial
<220> FEATURE:
<223> OTHER INFORMATION: Codon optimised

<400> SEQUENCE: 28
cccgtgatgt ccgttatcgg attcctggct ctggccaaag attgg 45

<210> SEQ ID NO 29
<211> LENGTH: 2292
<212> TYPE: DNA
<213> ORGANISM: Artificial
<220> FEATURE:
<223> OTHER INFORMATION: Chimeric sequence

<400> SEQUENCE: 29
atggccacaa tggaagagat ccagagagag atcagcgccc acgagggaca gctggttatc 60

```
gccagacaga aagtgaagga cgccgagaag cagtacgaga aggaccccga cgatctgaac    120
aagagagccc tgcacgacag agaaagcgtg gccgcctcta tccagagcaa gatcgatgag    180
ctgaagagac agctggccga cagaatcgcc gctggcaaga atattggcca ggacagagat    240
cccacaggcg tggaacctgg cgatcacctg aaagagagaa gcgccctgtc ctatggcaac    300
accctggacc tgaacagcct ggacattgat gagcctaccg gccagacagc cgactggctg    360
acaatcattg tgtacctgac cagcttcgtg gtccccatca tcctgaaggc cctgtacatg    420
ctgaccacca gaggcagaca gaccagcaag gacaacaagg gcatgagaat ccggttcaag    480
gatgacagca gctacgagga cgtgaacggc attagaaagc ccaagcacct gtacgtgtcc    540
atgcctaacg ctcagagcag catgaaggcc gaggaaatca cccctggcag attcagaaca    600
gccgtgtgcg gactgtaccc cgctcagatc aaggccagaa acatggtgtc cccagtgatg    660
agcgtcgtgg gatttctggc cctggctaag gactggacca gcaggattga ggaatggctg    720
ggagcccctt gcaagtttat ggccgagtct cctatcgccg gcagcctgtc tggcaacccc    780
gtgaatagag actacatcag acagaggcag ggcgctctgg ccggaatgga acccaaagaa    840
tttcaggccc tgcggcagca ctctaaggat gccggatgta ccctggtgga acacattgag    900
agccccagca gcatctgggt tttcgctggc gctcctgata gatgccctcc tacctgtctg    960
tttgttggcg gaatggccga gctgggcgcc ttctttagca ttctgcagga catgcggaat   1020
accatcatgg ccagcaagac cgtgggcacc gccgatgaga agctgagaaa gaagtccagc   1080
ttctaccaga gctacctgcg gagaacccag agcatgggca ttcagctgga ccagagaatc   1140
atcgtgatgt tcatggtggc ctggggcaaa gaagccgtgg acaattttca cctgggcgac   1200
gacatggacc ccgagctgag atctctggcc cagatcctga tcgaccagaa agtcaaagag   1260
atctccaatc aagagcccat gaagctgatg ctgagctacg gcaacgtgct ggatctgaac   1320
cacctggata tcgacgagcc aacaggacag accgctgatt ggctgggcat cgtgatctac   1380
ctgacctcct ttgtggtgcc tattctgctc aaagccctct atatgctgac aacacgcgga   1440
aggcagacca ccaaagataa caaaggcacc cggatcaggt ttaaggacga cagctccttt   1500
gaggatgtca acggcatccg gaaacctaag cacctctatg tgtctctgcc caatgcacag   1560
tcctccatga aggcagaaga gatcacacca ggccggtaca gaaccgccat ctgtggactg   1620
tatcctgcac aaatcaaagc ccggcagatg atcagccccg tgatgtccgt tatcggattc   1680
ctggctctgg ccaaagattg gagcgacagg atcgagcagt ggctgagcga gccttgcaag   1740
ctgcttcctg atacagccgc tgtgtcactg cttggcggcc ctgccacaaa cagagattac   1800
ctgagacaga gacaggtggc actgggcaac atggaaacaa aagagagcaa ggccatccgg   1860
cagcatgccg aagctgctgg ctgtagcatg atcgaggata tcgagtcccc tagctccatt   1920
tgggtgttcg caggggcccc agatagatgt ccaccaacat gcctgttcat tgccggcatg   1980
gctgaactgg gagctttttt cagcatcctc caggatatgc gcaacacgat tatggcctcc   2040
aagacagtgg gaaccagcga ggaaaagctg cggaagaaaa gcagctttta ccagtcttac   2100
ctgaggcgga cccagtccat ggggatccaa ctggatcagc ggatcattgt gctgtttatg   2160
gtcgcttggg gaaaagaggc tgtcgataac ttccacctgg gagatgatat ggatcctgaa   2220
ctgcggaccc tggctcagtc cctgatcgat gtgaaagtga aagaaattag taatcaagaa   2280
cccctcaagc tg                                                       2292
```

<210> SEQ ID NO 30
<211> LENGTH: 2292

```
<212> TYPE: DNA
<213> ORGANISM: Artificial
<220> FEATURE:
<223> OTHER INFORMATION: Chimeric sequence

<400> SEQUENCE: 30

atgctgagct acggcaacgt gctggatctg aaccacctgg atatcgacga gccaacagga     60

cagaccgctg attggctggg catcgtgatc tacctgacct cctttgtggt gcctattctg    120

ctcaaagccc tctatatgct gacaacacgc ggaaggcaga ccaccaaaga taacaaaggc    180

acccggatca ggtttaagga cgacagctcc tttgaggatg tcaacggcat ccggaaacct    240

aagcacctct atgtgtctct gcccaatgca cagtcctcca tgaaggcaga agagatcaca    300

ccaggccggt acagaaccgc catctgtgga ctgtatcctg cacaaatcaa agcccggcag    360

atgatcagcc ccgtgatgtc cgttatcgga ttcctggctc tggccaaaga ttggagcgac    420

aggatcgagc agtggctgag cgagccttgc aagctgcttc ctgatacagc cgctgtgtca    480

ctgcttggcg gccctgccac aaacagagat tacctgagac agagacaggt ggcactgggc    540

aacatggaaa caaaagagag caaggccatc cggcagcatg ccgaagctgc tggctgtagc    600

atgatcgagg atatcgagtc ccctagctcc atttgggtgt tcgcaggggc cccagataga    660

tgtccaccaa catgcctgtt cattgccggc atggctgaac tgggagcttt tttcagcatc    720

ctccaggata tgcgcaacac gattatggcc tccaagacag tgggaaccag cgaggaaaag    780

ctgcggaaga aaagcagctt ttaccagtct tacctgaggc ggacccagtc catggggatc    840

caactggatc agcggatcat tgtgctgttt atggtcgctt ggggaaaaga ggctgtcgat    900

aacttccacc tgggagatga tatggatcct gaactgcgga ccctggctca gtccctgatc    960

gatgtgaaag tgaaagaaat tagtaatcaa gaacccctca agctgatggc cacaatggaa   1020

gagatccaga gagagatcag cgcccacgag ggacagctgg ttatcgccag acagaaagtg   1080

aaggacgccg agaagcagta cgagaaggac cccgacgatc tgaacaagag agccctgcac   1140

gacagagaaa gcgtggccgc ctctatccag agcaagatcg atgagctgaa gagacagctg   1200

gccgacagaa tcgccgctgg caagaatatt ggccaggaca gagatcccac aggcgtggaa   1260

cctggcgatc acctgaaaga gagaagcgcc ctgtcctatg gcaacaccct ggacctgaac   1320

agcctggaca ttgatgagcc taccggccag acagccgact ggctgacaat cattgtgtac   1380

ctgaccagct tcgtggtccc catcatcctg aaggccctgt acatgctgac caccagaggc   1440

agacagacca gcaaggacaa caagggcatg agaatccggt tcaaggatga cagcagctac   1500

gaggacgtga acggcattag aaagcccaag cacctgtacg tgtccatgcc taacgctcag   1560

agcagcatga aggccgagga aatcacccct ggcagattca gaacagccgt gtgcggactg   1620

taccccgctc agatcaaggc cagaaacatg gtgtccccag tgatgagcgt cgtgggattt   1680

ctggccctgg ctaaggactg gaccagcagg attgaggaat ggctgggagc cccttgcaag   1740

tttatggccg agtctcctat cgccggcagc ctgtctggca accccgtgaa tagagactac   1800

atcagacaga ggcagggcgc tctggccgga atggaaccca aagaatttca ggccctgcgg   1860

cagcactcta aggatgccgg atgtaccctg gtggaacaca ttgagagccc cagcagcatc   1920

tgggttttcg ctggcgctcc tgatagatgc cctcctacct gtctgtttgt tggcggaatg   1980

gccgagctgg gcgccttctt tagcattctg caggacatgc ggaataccat catggccagc   2040

aagaccgtgg gcaccgccga tgagaagctg agaaagaagt ccagcttcta ccagagctac   2100

ctgcggagaa cccagagcat gggcattcag ctggaccaga gaatcatcgt gatgttcatg   2160
```

gtggcctggg gcaaagaagc cgtggacaat tttcacctgg gcgacgacat ggaccccgag 2220
ctgagatctc tggcccagat cctgatcgac cagaaagtca aagagatctc caatcaagag 2280
cccatgaagc tg 2292

<210> SEQ ID NO 31
<211> LENGTH: 764
<212> TYPE: PRT
<213> ORGANISM: Artificial
<220> FEATURE:
<223> OTHER INFORMATION: Chimeric protein

<400> SEQUENCE: 31

Met Ala Thr Met Glu Glu Ile Gln Arg Glu Ile Ser Ala His Glu Gly
1 5 10 15

Gln Leu Val Ile Ala Arg Gln Lys Val Lys Asp Ala Glu Lys Gln Tyr
20 25 30

Glu Lys Asp Pro Asp Asp Leu Asn Lys Arg Ala Leu His Asp Arg Glu
35 40 45

Ser Val Ala Ala Ser Ile Gln Ser Lys Ile Asp Glu Leu Lys Arg Gln
50 55 60

Leu Ala Asp Arg Ile Ala Ala Gly Lys Asn Ile Gly Gln Asp Arg Asp
65 70 75 80

Pro Thr Gly Val Glu Pro Gly Asp His Leu Lys Glu Arg Ser Ala Leu
85 90 95

Ser Tyr Gly Asn Thr Leu Asp Leu Asn Ser Leu Asp Ile Asp Glu Pro
100 105 110

Thr Gly Gln Thr Ala Asp Trp Leu Thr Ile Ile Val Tyr Leu Thr Ser
115 120 125

Phe Val Val Pro Ile Ile Leu Lys Ala Leu Tyr Met Leu Thr Thr Arg
130 135 140

Gly Arg Gln Thr Ser Lys Asp Asn Lys Gly Met Arg Ile Arg Phe Lys
145 150 155 160

Asp Asp Ser Ser Tyr Glu Asp Val Asn Gly Ile Arg Lys Pro Lys His
165 170 175

Leu Tyr Val Ser Met Pro Asn Ala Gln Ser Ser Met Lys Ala Glu Glu
180 185 190

Ile Thr Pro Gly Arg Phe Arg Thr Ala Val Cys Gly Leu Tyr Pro Ala
195 200 205

Gln Ile Lys Ala Arg Asn Met Val Ser Pro Val Met Ser Val Val Gly
210 215 220

Phe Leu Ala Leu Ala Lys Asp Trp Thr Ser Arg Ile Glu Glu Trp Leu
225 230 235 240

Gly Ala Pro Cys Lys Phe Met Ala Glu Ser Pro Ile Ala Gly Ser Leu
245 250 255

Ser Gly Asn Pro Val Asn Arg Asp Tyr Ile Arg Gln Arg Gln Gly Ala
260 265 270

Leu Ala Gly Met Glu Pro Lys Glu Phe Gln Ala Leu Arg Gln His Ser
275 280 285

Lys Asp Ala Gly Cys Thr Leu Val Glu His Ile Glu Ser Pro Ser Ser
290 295 300

Ile Trp Val Phe Ala Gly Ala Pro Asp Arg Cys Pro Pro Thr Cys Leu
305 310 315 320

Phe Val Gly Gly Met Ala Glu Leu Gly Ala Phe Phe Ser Ile Leu Gln
325 330 335

-continued

Asp Met Arg Asn Thr Ile Met Ala Ser Lys Thr Val Gly Thr Ala Asp
340 345 350

Glu Lys Leu Arg Lys Lys Ser Ser Phe Tyr Gln Ser Tyr Leu Arg Arg
355 360 365

Thr Gln Ser Met Gly Ile Gln Leu Asp Gln Arg Ile Ile Val Met Phe
370 375 380

Met Val Ala Trp Gly Lys Glu Ala Val Asp Asn Phe His Leu Gly Asp
385 390 395 400

Asp Met Asp Pro Glu Leu Arg Ser Leu Ala Gln Ile Leu Ile Asp Gln
405 410 415

Lys Val Lys Glu Ile Ser Asn Gln Glu Pro Met Lys Leu Met Leu Ser
420 425 430

Tyr Gly Asn Val Leu Asp Leu Asn His Leu Asp Ile Asp Glu Pro Thr
435 440 445

Gly Gln Thr Ala Asp Trp Leu Gly Ile Val Ile Tyr Leu Thr Ser Phe
450 455 460

Val Val Pro Ile Leu Leu Lys Ala Leu Tyr Met Leu Thr Thr Arg Gly
465 470 475 480

Arg Gln Thr Thr Lys Asp Asn Lys Gly Thr Arg Ile Arg Phe Lys Asp
485 490 495

Asp Ser Ser Phe Glu Asp Val Asn Gly Ile Arg Lys Pro Lys His Leu
500 505 510

Tyr Val Ser Leu Pro Asn Ala Gln Ser Ser Met Lys Ala Glu Glu Ile
515 520 525

Thr Pro Gly Arg Tyr Arg Thr Ala Ile Cys Gly Leu Tyr Pro Ala Gln
530 535 540

Ile Lys Ala Arg Gln Met Ile Ser Pro Val Met Ser Val Ile Gly Phe
545 550 555 560

Leu Ala Leu Ala Lys Asp Trp Ser Asp Arg Ile Glu Gln Trp Leu Ser
565 570 575

Glu Pro Cys Lys Leu Leu Pro Asp Thr Ala Ala Val Ser Leu Leu Gly
580 585 590

Gly Pro Ala Thr Asn Arg Asp Tyr Leu Arg Gln Arg Gln Val Ala Leu
595 600 605

Gly Asn Met Glu Thr Lys Glu Ser Lys Ala Ile Arg Gln His Ala Glu
610 615 620

Ala Ala Gly Cys Ser Met Ile Glu Asp Ile Glu Ser Pro Ser Ser Ile
625 630 635 640

Trp Val Phe Ala Gly Ala Pro Asp Arg Cys Pro Pro Thr Cys Leu Phe
645 650 655

Ile Ala Gly Met Ala Glu Leu Gly Ala Phe Phe Ser Ile Leu Gln Asp
660 665 670

Met Arg Asn Thr Ile Met Ala Ser Lys Thr Val Gly Thr Ser Glu Glu
675 680 685

Lys Leu Arg Lys Lys Ser Ser Phe Tyr Gln Ser Tyr Leu Arg Arg Thr
690 695 700

Gln Ser Met Gly Ile Gln Leu Asp Gln Arg Ile Ile Val Leu Phe Met
705 710 715 720

Val Ala Trp Gly Lys Glu Ala Val Asp Asn Phe His Leu Gly Asp Asp
725 730 735

Met Asp Pro Glu Leu Arg Thr Leu Ala Gln Ser Leu Ile Asp Val Lys
740 745 750

Val Lys Glu Ile Ser Asn Gln Glu Pro Leu Lys Leu 755 760

<210> SEQ ID NO 32
<211> LENGTH: 764
<212> TYPE: PRT
<213> ORGANISM: Artificial
<220> FEATURE:
<223> OTHER INFORMATION: Chimeric protein

<400> SEQUENCE: 32

Met Leu Ser Tyr Gly Asn Val Leu Asp Leu Asn His Leu Asp Ile Asp
1 5 10 15

Glu Pro Thr Gly Gln Thr Ala Asp Trp Leu Gly Ile Val Ile Tyr Leu
20 25 30

Thr Ser Phe Val Val Pro Ile Leu Leu Lys Ala Leu Tyr Met Leu Thr
35 40 45

Thr Arg Gly Arg Gln Thr Thr Lys Asp Asn Lys Gly Thr Arg Ile Arg
50 55 60

Phe Lys Asp Asp Ser Ser Phe Glu Asp Val Asn Gly Ile Arg Lys Pro
65 70 75 80

Lys His Leu Tyr Val Ser Leu Pro Asn Ala Gln Ser Ser Met Lys Ala
85 90 95

Glu Glu Ile Thr Pro Gly Arg Tyr Arg Thr Ala Ile Cys Gly Leu Tyr
100 105 110

Pro Ala Gln Ile Lys Ala Arg Gln Met Ile Ser Pro Val Met Ser Val
115 120 125

Ile Gly Phe Leu Ala Leu Ala Lys Asp Trp Ser Asp Arg Ile Glu Gln
130 135 140

Trp Leu Ser Glu Pro Cys Lys Leu Leu Pro Asp Thr Ala Ala Val Ser
145 150 155 160

Leu Leu Gly Gly Pro Ala Thr Asn Arg Asp Tyr Leu Arg Gln Arg Gln
165 170 175

Val Ala Leu Gly Asn Met Glu Thr Lys Glu Ser Lys Ala Ile Arg Gln
180 185 190

His Ala Glu Ala Ala Gly Cys Ser Met Ile Glu Asp Ile Glu Ser Pro
195 200 205

Ser Ser Ile Trp Val Phe Ala Gly Ala Pro Asp Arg Cys Pro Pro Thr
210 215 220

Cys Leu Phe Ile Ala Gly Met Ala Glu Leu Gly Ala Phe Phe Ser Ile
225 230 235 240

Leu Gln Asp Met Arg Asn Thr Ile Met Ala Ser Lys Thr Val Gly Thr
245 250 255

Ser Glu Glu Lys Leu Arg Lys Lys Ser Ser Phe Tyr Gln Ser Tyr Leu
260 265 270

Arg Arg Thr Gln Ser Met Gly Ile Gln Leu Asp Gln Arg Ile Ile Val
275 280 285

Leu Phe Met Val Ala Trp Gly Lys Glu Ala Val Asp Asn Phe His Leu
290 295 300

Gly Asp Asp Met Asp Pro Glu Leu Arg Thr Leu Ala Gln Ser Leu Ile
305 310 315 320

Asp Val Lys Val Lys Glu Ile Ser Asn Gln Glu Pro Leu Lys Leu Met
325 330 335

Ala Thr Met Glu Glu Ile Gln Arg Glu Ile Ser Ala His Glu Gly Gln
340 345 350

Leu Val Ile Ala Arg Gln Lys Val Lys Asp Ala Glu Lys Gln Tyr Glu

```
        355                 360                 365

Lys Asp Pro Asp Asp Leu Asn Lys Arg Ala Leu His Asp Arg Glu Ser
    370                 375                 380

Val Ala Ala Ser Ile Gln Ser Lys Ile Asp Glu Leu Lys Arg Gln Leu
385                 390                 395                 400

Ala Asp Arg Ile Ala Ala Gly Lys Asn Ile Gly Gln Asp Arg Asp Pro
                405                 410                 415

Thr Gly Val Glu Pro Gly Asp His Leu Lys Glu Arg Ser Ala Leu Ser
            420                 425                 430

Tyr Gly Asn Thr Leu Asp Leu Asn Ser Leu Asp Ile Asp Glu Pro Thr
        435                 440                 445

Gly Gln Thr Ala Asp Trp Leu Thr Ile Ile Val Tyr Leu Thr Ser Phe
    450                 455                 460

Val Val Pro Ile Ile Leu Lys Ala Leu Tyr Met Leu Thr Thr Arg Gly
465                 470                 475                 480

Arg Gln Thr Ser Lys Asp Asn Lys Gly Met Arg Ile Arg Phe Lys Asp
                485                 490                 495

Asp Ser Ser Tyr Glu Asp Val Asn Gly Ile Arg Lys Pro Lys His Leu
            500                 505                 510

Tyr Val Ser Met Pro Asn Ala Gln Ser Ser Met Lys Ala Glu Glu Ile
        515                 520                 525

Thr Pro Gly Arg Phe Arg Thr Ala Val Cys Gly Leu Tyr Pro Ala Gln
    530                 535                 540

Ile Lys Ala Arg Asn Met Val Ser Pro Val Met Ser Val Val Gly Phe
545                 550                 555                 560

Leu Ala Leu Ala Lys Asp Trp Thr Ser Arg Ile Glu Glu Trp Leu Gly
                565                 570                 575

Ala Pro Cys Lys Phe Met Ala Glu Ser Pro Ile Ala Gly Ser Leu Ser
            580                 585                 590

Gly Asn Pro Val Asn Arg Asp Tyr Ile Arg Gln Arg Gln Gly Ala Leu
        595                 600                 605

Ala Gly Met Glu Pro Lys Glu Phe Gln Ala Leu Arg Gln His Ser Lys
    610                 615                 620

Asp Ala Gly Cys Thr Leu Val Glu His Ile Glu Ser Pro Ser Ser Ile
625                 630                 635                 640

Trp Val Phe Ala Gly Ala Pro Asp Arg Cys Pro Pro Thr Cys Leu Phe
                645                 650                 655

Val Gly Gly Met Ala Glu Leu Gly Ala Phe Phe Ser Ile Leu Gln Asp
            660                 665                 670

Met Arg Asn Thr Ile Met Ala Ser Lys Thr Val Gly Thr Ala Asp Glu
        675                 680                 685

Lys Leu Arg Lys Lys Ser Ser Phe Tyr Gln Ser Tyr Leu Arg Arg Thr
    690                 695                 700

Gln Ser Met Gly Ile Gln Leu Asp Gln Arg Ile Ile Val Met Phe Met
705                 710                 715                 720

Val Ala Trp Gly Lys Glu Ala Val Asp Asn Phe His Leu Gly Asp Asp
                725                 730                 735

Met Asp Pro Glu Leu Arg Ser Leu Ala Gln Ile Leu Ile Asp Gln Lys
            740                 745                 750

Val Lys Glu Ile Ser Asn Gln Glu Pro Met Lys Leu
        755                 760
```

<210> SEQ ID NO 33

<211> LENGTH: 4695
<212> TYPE: DNA
<213> ORGANISM: Artificial
<220> FEATURE:
<223> OTHER INFORMATION: pMVAHantaNP

<400> SEQUENCE: 33

```
gttggtggtc gccatggatg gtgttattgt atactgtcta aacgcgttag taaaacatgg     60

cgaggaaata aatcatataa aaaatgattt catgattaaa ccatgttgtg aaaaagtcaa    120

gaacgttcac attggcggac aatctaaaaa caatacagtg attgcagatt tgccatatat    180

ggataatgcg gtatccgatg tatgcaattc actgtataaa aagaatgtat caagaatatc    240

cagatttgct aatttgataa agatagatga cgatgacaag actcctactg gtgtatataa    300

ttattttaaa cctaaagatg ccattcctgt tattatatcc ataggaaagg atagagatgt    360

ttgtgaacta ttaatctcat ctgataaagc gtgtgcgtgt atagagttaa attcatataa    420

agtagccatt cttcccatgg atgtttcctt ttttaccaaa ggaaatgcat cattgattat    480

tctcctgttt gatttctcta tcgatgcggc acctctctta agaagtgtaa ccgataataa    540

tgttattata tctagacacc agcgtctaca tgacgagctt ccgagttcca attggttcaa    600

gttttacata agtataaagt ccgactattg ttctatatta tatatggttg ttgatggatc    660

tgtgatgcat gcaatagctg ataatagaac ttacgcaaat attagcaaaa atatattaga    720

caatactaca attaacgatg agtgtagatg ctgttatttt gaaccacaga ttaggattct    780

tgatagagat gagatgctca atggatcatc gtgtgatatg aacagacatt gtattatgat    840

gaatttacct gatgtaggcg aatttggatc tagtatgttg ggaaatatg aacctgacat     900

gattaagatt gctctttcgg tggctgggta ccaggcgcgc ctttcatttt gtttttttct    960

atgctataaa tggtgagcaa gggcgaggag ctgttcaccg gggtggtgcc catcctggtc   1020

gagctggacg gcgacgtaaa cggccacaag ttcagcgtgt ccggcgaggg cgagggcgat   1080

gccacctacg gcaagctgac cctgaagttc atctgcacca ccggcaagct gcccgtgccc   1140

tggcccaccc tcgtgaccac cctgacctac ggcgtgcagt gcttcagccg ctaccccgac   1200

cacatgaagc agcacgactt cttcaagtcc gccatgcccg aaggctacgt ccaggagcgc   1260

accatcttct tcaaggacga cggcaactac aagacccgcg ccgaggtgaa gttcgagggc   1320

gacaccctgg tgaaccgcat cgagctgaag ggcatcgact tcaaggagga cggcaacatc   1380

ctggggcaca agctggagta caactacaac agccacaacg tctatatcat ggccgacaag   1440

cagaagaacg gcatcaaggt gaacttcaag atccgccaca acatcgagga cggcagcgtg   1500

cagctcgccg accactacca gcagaacacc cccatcggcg acggccccgt gctgctgccc   1560

gacaaccact acctgagcac ccagtccgcc ctgagcaaag accccaacga gaagcgcgat   1620

cacatggtcc tgctggagtt cgtgaccgcc gccgggatca ctctcggcat ggacgagctg   1680

tacaagtaag agctccggcc cgctcgaggc cgctggtacc caacctaaaa attgaaaata   1740

aatacaaagg ttcttgaggg ttgtgttaaa ttgaaagcga gaaataatca taaataagcc   1800

cggtgccacc atggccacaa tggaagagat ccagagagag atcagcgccc acgagggaca   1860

gctggttatc gccagacaga aagtgaagga cgccgagaag cagtacgaga aggaccccga   1920

cgatctgaac aagagagccc tgcacgacag agaaagcgtg gccgcctcta tccagagcaa   1980

gatcgatgag ctgaagagac agctggccga cagaatcgcc gctggcaaga atattggcca   2040

ggacagagat cccacaggcg tggaacctgg cgatcacctg aaagagagaa gcgccctgtc   2100

ctatggcaac accctggacc tgaacagcct ggacattgat gagcctaccg gccagacagc   2160
```

```
cgactggctg acaatcattg tgtacctgac cagcttcgtg gtccccatca tcctgaaggc   2220
cctgtacatg ctgaccacca gaggcagaca gaccagcaag gacaacaagg gcatgagaat   2280
ccggttcaag gatgacagca gctacgagga cgtgaacggc attagaaagc ccaagcacct   2340
gtacgtgtcc atgcctaacg ctcagagcag catgaaggcc gaggaaatca cccctggcag   2400
attcagaaca gccgtgtgcg gactgtaccc cgctcagatc aaggccagaa acatggtgtc   2460
cccagtgatg agcgtcgtgg gatttctggc cctggctaag gactggacca gcaggattga   2520
ggaatggctg ggagcccctt gcaagtttat ggccgagtct cctatcgccg gcagcctgtc   2580
tggcaacccc gtgaatagag actacatcag acagaggcag ggcgctctgg ccggaatgga   2640
acccaaagaa tttcaggccc tgcggcagca ctctaaggat gccggatgta ccctggtgga   2700
acacattgag agccccagca gcatctgggt tttcgctggc gctcctgata gatgccctcc   2760
tacctgtctg tttgttggcg gaatggccga gctgggcgcc ttctttagca ttctgcagga   2820
catgcggaat accatcatgg ccagcaagac cgtgggcacc gccgatgaga agctgagaaa   2880
gaagtccagc ttctaccaga gctacctgcg gagaacccag agcatgggca ttcagctgga   2940
ccagagaatc atcgtgatgt tcatggtggc ctggggcaaa gaagccgtgg acaattttca   3000
cctgggcgac gacatggacc ccgagctgag atctctggcc cagatcctga tcgaccagaa   3060
agtcaaagag atctccaatc aagagcccat gaagctgatg ctgagctacg gcaacgtgct   3120
ggatctgaac cacctggata tcgacgagcc aacaggacag accgctgatt ggctgggcat   3180
cgtgatctac ctgacctcct ttgtggtgcc tattctgctc aaagccctct atatgctgac   3240
aacacgcgga aggcagacca ccaaagataa caaaggcacc cggatcaggt ttaaggacga   3300
cagctccttt gaggatgtca acggcatccg gaaacctaag cacctctatg tgtctctgcc   3360
caatgcacag tcctccatga aggcagaaga gatcacacca ggccggtaca gaaccgccat   3420
ctgtggactg tatcctgcac aaatcaaagc ccggcagatg atcagccccg tgatgtccgt   3480
tatcggattc ctggctctgg ccaaagattg gagcgacagg atcgagcagt ggctgagcga   3540
gccttgcaag ctgcttcctg atacagccgc tgtgtcactg cttggcggcc ctgccacaaa   3600
cagagattac ctgagacaga gacaggtggc actgggcaac atggaaacaa aagagagcaa   3660
ggccatccgg cagcatgccg aagctgctgg ctgtagcatg atcgaggata tcgagtcccc   3720
tagctccatt tgggtgttcg caggggcccc agatagatgt ccaccaacat gcctgttcat   3780
tgccggcatg gctgaactgg gagctttttt cagcatcctc caggatatgc gcaacacgat   3840
tatggcctcc aagacagtgg gaaccagcga ggaaaagctg cggaagaaaa gcagctttta   3900
ccagtcttac ctgaggcgga cccagtccat ggggatccaa ctggatcagc ggatcattgt   3960
gctgtttatg gtcgcttggg gaaaagaggc tgtcgataac ttccacctgg gagatgatat   4020
ggatcctgaa ctgcggaccc tggctcagtc cctgatcgat gtgaaagtga aagaaattag   4080
taatcaagaa cccctcaagc tggacctgga aggccctaga ttcgaggact acaaggacga   4140
tgacgacaag tgactcgacc tgcagttttt atggaaagtt ttataggtag ttgatagaac   4200
aaaatacata attttgtaaa aataaatcac tttttatact aatatgacac gattaccaat   4260
acttttgtta ctaatatcat tagtatacgc tacacctttt cctcagacat ctaaaaaaat   4320
aggtgatgat gcaactttat catgtaatcg aaataataca aatgactacg ttgttatgag   4380
tgcttggtat aaggagccca attccattat tcttttagct gctaaaagcg acgtcttgta   4440
ttttgataat tataccaagg ataaaaatatc ttacgactct ccatacgatg atctagttac   4500
```

aactatcaca attaaatcat tgactgctag agatgccggt acttatgtat gtgcattctt 4560
tatgacatcg cctacaaatg acactgataa agtagattat gaagaatact ccacagagtt 4620
gattgtaaat acagatagtg aatcgactat agacataata ctatctggat ctacacattc 4680
accggaaact agttg 4695

<210> SEQ ID NO 34
<211> LENGTH: 927
<212> TYPE: DNA
<213> ORGANISM: Artificial
<220> FEATURE:
<223> OTHER INFORMATION: DelIII Left flank

<400> SEQUENCE: 34
gttggtggtc gccatggatg gtgttattgt atactgtcta aacgcgttag taaaacatgg 60
cgaggaaata aatcatataa aaaatgattt catgattaaa ccatgttgtg aaaaagtcaa 120
gaacgttcac attggcggac aatctaaaaa caatacagtg attgcagatt tgccatatat 180
ggataatgcg gtatccgatg tatgcaattc actgtataaa aagaatgtat caagaatatc 240
cagatttgct aatttgataa agatagatga cgatgacaag actcctactg gtgtatataa 300
ttattttaaa cctaaagatg ccattcctgt tattatatcc ataggaaagg atagagatgt 360
ttgtgaacta ttaatctcat ctgataaagc gtgtgcgtgt atagagttaa attcatataa 420
agtagccatt cttcccatgg atgtttcctt ttttaccaaa ggaaatgcat cattgattat 480
tctcctgttt gatttctcta tcgatgcggc acctctctta agaagtgtaa ccgataataa 540
tgttattata tctagacacc agcgtctaca tgacgagctt ccgagttcca attggttcaa 600
gttttacata agtataaagt ccgactattg ttctatatta tatatggttg ttgatggatc 660
tgtgatgcat gcaatagctg ataatagaac ttacgcaaat attagcaaaa atatattaga 720
caatactaca attaacgatg agtgtagatg ctgttatttt gaaccacaga ttaggattct 780
tgatagagat gagatgctca atggatcatc gtgtgatatg aacagacatt gtattatgat 840
gaatttacct gatgtaggcg aatttggatc tagtatgttg ggaaatatg aacctgacat 900 gattaagatt gctctttcgg tggctgg 927

<210> SEQ ID NO 35
<211> LENGTH: 14
<212> TYPE: DNA
<213> ORGANISM: Artificial
<220> FEATURE:
<223> OTHER INFORMATION: First linker

<400> SEQUENCE: 35
gtaccaggcg cgcc 14

<210> SEQ ID NO 36
<211> LENGTH: 28
<212> TYPE: DNA
<213> ORGANISM: Artificial
<220> FEATURE:
<223> OTHER INFORMATION: p11

<400> SEQUENCE: 36
tttcattttg ttttttcta tgctataa 28

<210> SEQ ID NO 37
<211> LENGTH: 720
<212> TYPE: DNA
<213> ORGANISM: Artificial

```
<220> FEATURE:
<223> OTHER INFORMATION: Green fluorescent protein

<400> SEQUENCE: 37

atggtgagca agggcgagga gctgttcacc ggggtggtgc ccatcctggt cgagctggac     60

ggcgacgtaa acggccacaa gttcagcgtg tccggcgagg gcgagggcga tgccacctac    120

ggcaagctga ccctgaagtt catctgcacc accggcaagc tgcccgtgcc ctggcccacc    180

ctcgtgacca ccctgaccta cggcgtgcag tgcttcagcc gctaccccga ccacatgaag    240

cagcacgact tcttcaagtc cgccatgccc gaaggctacg tccaggagcg caccatcttc    300

ttcaaggacg acggcaacta caagacccgc gccgaggtga agttcgaggg cgacaccctg    360

gtgaaccgca tcgagctgaa gggcatcgac ttcaaggagg acggcaacat cctggggcac    420

aagctggagt acaactacaa cagccacaac gtctatatca tggccgacaa gcagaagaac    480

ggcatcaagg tgaacttcaa gatccgccac aacatcgagg acggcagcgt gcagctcgcc    540

gaccactacc agcagaacac ccccatcggc gacggccccg tgctgctgcc cgacaaccac    600

tacctgagca cccagtccgc cctgagcaaa gaccccaacg agaagcgcga tcacatggtc    660

ctgctggagt tcgtgaccgc cgccgggatc actctcggca tggacgagct gtacaagtaa    720


<210> SEQ ID NO 38
<211> LENGTH: 37
<212> TYPE: DNA
<213> ORGANISM: Artificial
<220> FEATURE:
<223> OTHER INFORMATION: Second linker

<400> SEQUENCE: 38

gagctccggc ccgctcgagg ccgctggtac ccaacct                               37


<210> SEQ ID NO 39
<211> LENGTH: 70
<212> TYPE: DNA
<213> ORGANISM: Artificial
<220> FEATURE:
<223> OTHER INFORMATION: MH5 promoter

<400> SEQUENCE: 39

aaaaattgaa aataaataca aaggttcttg agggttgtgt taaattgaaa gcgagaaata     60

atcataaata                                                            70


<210> SEQ ID NO 40
<211> LENGTH: 15
<212> TYPE: PRT
<213> ORGANISM: Artificial
<220> FEATURE:
<223> OTHER INFORMATION: Peptide pool

<400> SEQUENCE: 40

Asp Val Lys Val Lys Glu Ile Ser Asn Gln Glu Pro Leu Lys Leu
1               5                   10                  15


<210> SEQ ID NO 41
<211> LENGTH: 10
<212> TYPE: DNA
<213> ORGANISM: Artificial
<220> FEATURE:
<223> OTHER INFORMATION: Kozak sequence

<400> SEQUENCE: 41

gccaccatgg                                                            10
```

<210> SEQ ID NO 42
<211> LENGTH: 24
<212> TYPE: DNA
<213> ORGANISM: Artificial
<220> FEATURE:
<223> OTHER INFORMATION: Fourth linker

<400> SEQUENCE: 42
gacctggaag gccctagatt cgag 24

<210> SEQ ID NO 43
<211> LENGTH: 24
<212> TYPE: DNA
<213> ORGANISM: Artificial
<220> FEATURE:
<223> OTHER INFORMATION: Flag tag

<400> SEQUENCE: 43
gactacaagg acgatgacga caag 24

<210> SEQ ID NO 44
<211> LENGTH: 20
<212> TYPE: DNA
<213> ORGANISM: Artificial
<220> FEATURE:
<223> OTHER INFORMATION: Fifth linker

<400> SEQUENCE: 44
ctcgacctgc agtttttatg 20

<210> SEQ ID NO 45
<211> LENGTH: 522
<212> TYPE: DNA
<213> ORGANISM: Artificial
<220> FEATURE:
<223> OTHER INFORMATION: DelIII Right Flank

<400> SEQUENCE: 45
gaaagtttta taggtagttg atagaacaaa atacataatt ttgtaaaaat aaatcacttt 60
ttatactaat atgacacgat taccaatact tttgttacta atatcattag tatacgctac 120
accttttcct cagacatcta aaaaaatagg tgatgatgca actttatcat gtaatcgaaa 180
taatacaaat gactacgttg ttatgagtgc ttggtataag gagcccaatt ccattattct 240
tttagctgct aaaagcgacg tcttgtattt tgataattat accaaggata aaatatctta 300
cgactctcca tacgatgatc tagttacaac tatcacaatt aaatcattga ctgctagaga 360
tgccggtact tatgtatgtg cattctttat gacatcgcct acaaatgaca ctgataaagt 420
agattatgaa gaatactcca cagagttgat tgtaaataca gatagtgaat cgactataga 480
cataatacta tctggatcta cacattcacc ggaaactagt tg 522

<210> SEQ ID NO 46
<211> LENGTH: 20
<212> TYPE: DNA
<213> ORGANISM: Artificial
<220> FEATURE:
<223> OTHER INFORMATION: Primer

<400> SEQUENCE: 46
cggcacctct cttaagaagt 20

<210> SEQ ID NO 47

```
<211> LENGTH: 25
<212> TYPE: DNA
<213> ORGANISM: Artificial
<220> FEATURE:
<223> OTHER INFORMATION: Primer

<400> SEQUENCE: 47

gtgtagcgta tactaatgat attag                                          25


<210> SEQ ID NO 48
<211> LENGTH: 26
<212> TYPE: DNA
<213> ORGANISM: Artificial
<220> FEATURE:
<223> OTHER INFORMATION: Primer

<400> SEQUENCE: 48

ggagtacaac tacaacagcc acaacg                                         26


<210> SEQ ID NO 49
<211> LENGTH: 780
<212> TYPE: PRT
<213> ORGANISM: Artificial
<220> FEATURE:
<223> OTHER INFORMATION: Chimeric protein

<400> SEQUENCE: 49

Met Ala Thr Met Glu Glu Ile Gln Arg Glu Ile Ser Ala His Glu Gly
1               5                   10                  15

Gln Leu Val Ile Ala Arg Gln Lys Val Lys Asp Ala Glu Lys Gln Tyr
            20                  25                  30

Glu Lys Asp Pro Asp Asp Leu Asn Lys Arg Ala Leu His Asp Arg Glu
        35                  40                  45

Ser Val Ala Ala Ser Ile Gln Ser Lys Ile Asp Glu Leu Lys Arg Gln
    50                  55                  60

Leu Ala Asp Arg Ile Ala Ala Gly Lys Asn Ile Gly Gln Asp Arg Asp
65                  70                  75                  80

Pro Thr Gly Val Glu Pro Gly Asp His Leu Lys Glu Arg Ser Ala Leu
                85                  90                  95

Ser Tyr Gly Asn Thr Leu Asp Leu Asn Ser Leu Asp Ile Asp Glu Pro
            100                 105                 110

Thr Gly Gln Thr Ala Asp Trp Leu Thr Ile Ile Val Tyr Leu Thr Ser
        115                 120                 125

Phe Val Val Pro Ile Ile Leu Lys Ala Leu Tyr Met Leu Thr Thr Arg
    130                 135                 140

Gly Arg Gln Thr Ser Lys Asp Asn Lys Gly Met Arg Ile Arg Phe Lys
145                 150                 155                 160

Asp Asp Ser Ser Tyr Glu Asp Val Asn Gly Ile Arg Lys Pro Lys His
                165                 170                 175

Leu Tyr Val Ser Met Pro Asn Ala Gln Ser Ser Met Lys Ala Glu Glu
            180                 185                 190

Ile Thr Pro Gly Arg Phe Arg Thr Ala Val Cys Gly Leu Tyr Pro Ala
        195                 200                 205

Gln Ile Lys Ala Arg Asn Met Val Ser Pro Val Met Ser Val Val Gly
    210                 215                 220

Phe Leu Ala Leu Ala Lys Asp Trp Thr Ser Arg Ile Glu Glu Trp Leu
225                 230                 235                 240

Gly Ala Pro Cys Lys Phe Met Ala Glu Ser Pro Ile Ala Gly Ser Leu
                245                 250                 255
```

```
Ser Gly Asn Pro Val Asn Arg Asp Tyr Ile Arg Gln Arg Gln Gly Ala
            260                 265                 270

Leu Ala Gly Met Glu Pro Lys Glu Phe Gln Ala Leu Arg Gln His Ser
        275                 280                 285

Lys Asp Ala Gly Cys Thr Leu Val Glu His Ile Glu Ser Pro Ser Ser
    290                 295                 300

Ile Trp Val Phe Ala Gly Ala Pro Asp Arg Cys Pro Pro Thr Cys Leu
305                 310                 315                 320

Phe Val Gly Gly Met Ala Glu Leu Gly Ala Phe Phe Ser Ile Leu Gln
                325                 330                 335

Asp Met Arg Asn Thr Ile Met Ala Ser Lys Thr Val Gly Thr Ala Asp
            340                 345                 350

Glu Lys Leu Arg Lys Lys Ser Ser Phe Tyr Gln Ser Tyr Leu Arg Arg
        355                 360                 365

Thr Gln Ser Met Gly Ile Gln Leu Asp Gln Arg Ile Ile Val Met Phe
    370                 375                 380

Met Val Ala Trp Gly Lys Glu Ala Val Asp Asn Phe His Leu Gly Asp
385                 390                 395                 400

Asp Met Asp Pro Glu Leu Arg Ser Leu Ala Gln Ile Leu Ile Asp Gln
                405                 410                 415

Lys Val Lys Glu Ile Ser Asn Gln Glu Pro Met Lys Leu Met Leu Ser
            420                 425                 430

Tyr Gly Asn Val Leu Asp Leu Asn His Leu Asp Ile Asp Glu Pro Thr
        435                 440                 445

Gly Gln Thr Ala Asp Trp Leu Gly Ile Val Ile Tyr Leu Thr Ser Phe
    450                 455                 460

Val Val Pro Ile Leu Leu Lys Ala Leu Tyr Met Leu Thr Thr Arg Gly
465                 470                 475                 480

Arg Gln Thr Thr Lys Asp Asn Lys Gly Thr Arg Ile Arg Phe Lys Asp
                485                 490                 495

Asp Ser Ser Phe Glu Asp Val Asn Gly Ile Arg Lys Pro Lys His Leu
            500                 505                 510

Tyr Val Ser Leu Pro Asn Ala Gln Ser Ser Met Lys Ala Glu Glu Ile
        515                 520                 525

Thr Pro Gly Arg Tyr Arg Thr Ala Ile Cys Gly Leu Tyr Pro Ala Gln
    530                 535                 540

Ile Lys Ala Arg Gln Met Ile Ser Pro Val Met Ser Val Ile Gly Phe
545                 550                 555                 560

Leu Ala Leu Ala Lys Asp Trp Ser Asp Arg Ile Glu Gln Trp Leu Ser
                565                 570                 575

Glu Pro Cys Lys Leu Leu Pro Asp Thr Ala Ala Val Ser Leu Leu Gly
            580                 585                 590

Gly Pro Ala Thr Asn Arg Asp Tyr Leu Arg Gln Arg Gln Val Ala Leu
        595                 600                 605

Gly Asn Met Glu Thr Lys Glu Ser Lys Ala Ile Arg Gln His Ala Glu
    610                 615                 620

Ala Ala Gly Cys Ser Met Ile Glu Asp Ile Glu Ser Pro Ser Ser Ile
625                 630                 635                 640

Trp Val Phe Ala Gly Ala Pro Asp Arg Cys Pro Pro Thr Cys Leu Phe
                645                 650                 655

Ile Ala Gly Met Ala Glu Leu Gly Ala Phe Phe Ser Ile Leu Gln Asp
            660                 665                 670
```

Met Arg Asn Thr Ile Met Ala Ser Lys Thr Val Gly Thr Ser Glu Glu
        675                 680                 685

Lys Leu Arg Lys Lys Ser Ser Phe Tyr Gln Ser Tyr Leu Arg Arg Thr
    690                 695                 700

Gln Ser Met Gly Ile Gln Leu Asp Gln Arg Ile Ile Val Leu Phe Met
705                 710                 715                 720

Val Ala Trp Gly Lys Glu Ala Val Asp Asn Phe His Leu Gly Asp Asp
                725                 730                 735

Met Asp Pro Glu Leu Arg Thr Leu Ala Gln Ser Leu Ile Asp Val Lys
            740                 745                 750

Val Lys Glu Ile Ser Asn Gln Glu Pro Leu Lys Leu Asp Leu Glu Gly
        755                 760                 765

Pro Arg Phe Glu Asp Tyr Lys Asp Asp Asp Asp Lys
    770                 775                 780

<210> SEQ ID NO 50
<211> LENGTH: 15
<212> TYPE: PRT
<213> ORGANISM: Artificial
<220> FEATURE:
<223> OTHER INFORMATION: Peptide pool

<400> SEQUENCE: 50

Met Ala Thr Met Glu Glu Ile Gln Arg Glu Ile Ser Ala His Glu
1               5                   10                  15

<210> SEQ ID NO 51
<211> LENGTH: 15
<212> TYPE: PRT
<213> ORGANISM: Artificial
<220> FEATURE:
<223> OTHER INFORMATION: Peptide pool

<400> SEQUENCE: 51

Glu Glu Ile Gln Arg Glu Ile Ser Ala His Glu Gly Gln Leu Val
1               5                   10                  15

<210> SEQ ID NO 52
<211> LENGTH: 15
<212> TYPE: PRT
<213> ORGANISM: Artificial
<220> FEATURE:
<223> OTHER INFORMATION: Peptide pool

<400> SEQUENCE: 52

Arg Glu Ile Ser Ala His Glu Gly Gln Leu Val Ile Ala Arg Gln
1               5                   10                  15

<210> SEQ ID NO 53
<211> LENGTH: 15
<212> TYPE: PRT
<213> ORGANISM: Artificial
<220> FEATURE:
<223> OTHER INFORMATION: Peptide pool

<400> SEQUENCE: 53

Ala His Glu Gly Gln Leu Val Ile Ala Arg Gln Lys Val Lys Asp
1               5                   10                  15

<210> SEQ ID NO 54
<211> LENGTH: 15
<212> TYPE: PRT
<213> ORGANISM: Artificial
<220> FEATURE:

<223> OTHER INFORMATION: Peptide pool

<400> SEQUENCE: 54

Gln Leu Val Ile Ala Arg Gln Lys Val Lys Asp Ala Glu Lys Gln
1 5 10 15

<210> SEQ ID NO 55
<211> LENGTH: 15
<212> TYPE: PRT
<213> ORGANISM: Artificial
<220> FEATURE:
<223> OTHER INFORMATION: Peptide pool

<400> SEQUENCE: 55

Ala Arg Gln Lys Val Lys Asp Ala Glu Lys Gln Tyr Glu Lys Asp
1 5 10 15

<210> SEQ ID NO 56
<211> LENGTH: 15
<212> TYPE: PRT
<213> ORGANISM: Artificial
<220> FEATURE:
<223> OTHER INFORMATION: Peptide pool

<400> SEQUENCE: 56

Val Lys Asp Ala Glu Lys Gln Tyr Glu Lys Asp Pro Asp Asp Leu
1 5 10 15

<210> SEQ ID NO 57
<211> LENGTH: 15
<212> TYPE: PRT
<213> ORGANISM: Artificial
<220> FEATURE:
<223> OTHER INFORMATION: Peptide pool

<400> SEQUENCE: 57

Glu Lys Gln Tyr Glu Lys Asp Pro Asp Asp Leu Asn Lys Arg Ala
1 5 10 15

<210> SEQ ID NO 58
<211> LENGTH: 15
<212> TYPE: PRT
<213> ORGANISM: Artificial
<220> FEATURE:
<223> OTHER INFORMATION: Peptide pool

<400> SEQUENCE: 58

Glu Lys Asp Pro Asp Asp Leu Asn Lys Arg Ala Leu His Asp Arg
1 5 10 15

<210> SEQ ID NO 59
<211> LENGTH: 15
<212> TYPE: PRT
<213> ORGANISM: Artificial
<220> FEATURE:
<223> OTHER INFORMATION: Peptide pool

<400> SEQUENCE: 59

Asp Asp Leu Asn Lys Arg Ala Leu His Asp Arg Glu Ser Val Ala
1 5 10 15

<210> SEQ ID NO 60
<211> LENGTH: 15
<212> TYPE: PRT
<213> ORGANISM: Artificial
<220> FEATURE:
<223> OTHER INFORMATION: Peptide pool

<400> SEQUENCE: 60

Lys Arg Ala Leu His Asp Arg Glu Ser Val Ala Ala Ser Ile Gln
1 5 10 15

<210> SEQ ID NO 61
<211> LENGTH: 15
<212> TYPE: PRT
<213> ORGANISM: Artificial
<220> FEATURE:
<223> OTHER INFORMATION: Peptide pool

<400> SEQUENCE: 61

His Asp Arg Glu Ser Val Ala Ala Ser Ile Gln Ser Lys Ile Asp
1 5 10 15

<210> SEQ ID NO 62
<211> LENGTH: 15
<212> TYPE: PRT
<213> ORGANISM: Artificial
<220> FEATURE:
<223> OTHER INFORMATION: Peptide pool

<400> SEQUENCE: 62

Ser Val Ala Ala Ser Ile Gln Ser Lys Ile Asp Glu Leu Lys Arg
1 5 10 15

<210> SEQ ID NO 63
<211> LENGTH: 15
<212> TYPE: PRT
<213> ORGANISM: Artificial
<220> FEATURE:
<223> OTHER INFORMATION: Peptide pool

<400> SEQUENCE: 63

Ser Ile Gln Ser Lys Ile Asp Glu Leu Lys Arg Gln Leu Ala Asp
1 5 10 15

<210> SEQ ID NO 64
<211> LENGTH: 15
<212> TYPE: PRT
<213> ORGANISM: Artificial
<220> FEATURE:
<223> OTHER INFORMATION: Peptide pool

<400> SEQUENCE: 64

Lys Ile Asp Glu Leu Lys Arg Gln Leu Ala Asp Arg Ile Ala Ala
1 5 10 15

<210> SEQ ID NO 65
<211> LENGTH: 15
<212> TYPE: PRT
<213> ORGANISM: Artificial
<220> FEATURE:
<223> OTHER INFORMATION: Peptide pool

<400> SEQUENCE: 65

Leu Lys Arg Gln Leu Ala Asp Arg Ile Ala Ala Gly Lys Asn Ile
1 5 10 15

<210> SEQ ID NO 66
<211> LENGTH: 15
<212> TYPE: PRT
<213> ORGANISM: Artificial
<220> FEATURE:
<223> OTHER INFORMATION: Peptide pool

<400> SEQUENCE: 66

Leu Ala Asp Arg Ile Ala Ala Gly Lys Asn Ile Gly Gln Asp Arg
1 5 10 15

<210> SEQ ID NO 67
<211> LENGTH: 15
<212> TYPE: PRT
<213> ORGANISM: Artificial
<220> FEATURE:
<223> OTHER INFORMATION: Peptide pool

<400> SEQUENCE: 67

Ile Ala Ala Gly Lys Asn Ile Gly Gln Asp Arg Asp Pro Thr Gly
1 5 10 15

<210> SEQ ID NO 68
<211> LENGTH: 15
<212> TYPE: PRT
<213> ORGANISM: Artificial
<220> FEATURE:
<223> OTHER INFORMATION: Peptide pool

<400> SEQUENCE: 68

Lys Asn Ile Gly Gln Asp Arg Asp Pro Thr Gly Val Glu Pro Gly
1 5 10 15

<210> SEQ ID NO 69
<211> LENGTH: 15
<212> TYPE: PRT
<213> ORGANISM: Artificial
<220> FEATURE:
<223> OTHER INFORMATION: Peptide pool

<400> SEQUENCE: 69

Gln Asp Arg Asp Pro Thr Gly Val Glu Pro Gly Asp His Leu Lys
1 5 10 15

<210> SEQ ID NO 70
<211> LENGTH: 15
<212> TYPE: PRT
<213> ORGANISM: Artificial
<220> FEATURE:
<223> OTHER INFORMATION: Peptide pool

<400> SEQUENCE: 70

Pro Thr Gly Val Glu Pro Gly Asp His Leu Lys Glu Arg Ser Ala
1 5 10 15

<210> SEQ ID NO 71
<211> LENGTH: 15
<212> TYPE: PRT
<213> ORGANISM: Artificial
<220> FEATURE:
<223> OTHER INFORMATION: Peptide pool

<400> SEQUENCE: 71

Glu Pro Gly Asp His Leu Lys Glu Arg Ser Ala Leu Ser Tyr Gly
1 5 10 15

<210> SEQ ID NO 72
<211> LENGTH: 15
<212> TYPE: PRT
<213> ORGANISM: Artificial
<220> FEATURE:
<223> OTHER INFORMATION: Peptide pool

<400> SEQUENCE: 72

His Leu Lys Glu Arg Ser Ala Leu Ser Tyr Gly Asn Thr Leu Asp
1 5 10 15

<210> SEQ ID NO 73
<211> LENGTH: 15
<212> TYPE: PRT
<213> ORGANISM: Artificial
<220> FEATURE:
<223> OTHER INFORMATION: Peptide pool

<400> SEQUENCE: 73

Arg Ser Ala Leu Ser Tyr Gly Asn Thr Leu Asp Leu Asn Ser Leu
1 5 10 15

<210> SEQ ID NO 74
<211> LENGTH: 15
<212> TYPE: PRT
<213> ORGANISM: Artificial
<220> FEATURE:
<223> OTHER INFORMATION: Peptide pool

<400> SEQUENCE: 74

Ser Tyr Gly Asn Thr Leu Asp Leu Asn Ser Leu Asp Ile Asp Glu
1 5 10 15

<210> SEQ ID NO 75
<211> LENGTH: 15
<212> TYPE: PRT
<213> ORGANISM: Artificial
<220> FEATURE:
<223> OTHER INFORMATION: Peptide pool

<400> SEQUENCE: 75

Thr Leu Asp Leu Asn Ser Leu Asp Ile Asp Glu Pro Thr Gly Gln
1 5 10 15

<210> SEQ ID NO 76
<211> LENGTH: 15
<212> TYPE: PRT
<213> ORGANISM: Artificial
<220> FEATURE:
<223> OTHER INFORMATION: Peptide pool

<400> SEQUENCE: 76

Asn Ser Leu Asp Ile Asp Glu Pro Thr Gly Gln Thr Ala Asp Trp
1 5 10 15

<210> SEQ ID NO 77
<211> LENGTH: 15
<212> TYPE: PRT
<213> ORGANISM: Artificial
<220> FEATURE:
<223> OTHER INFORMATION: Peptide pool

<400> SEQUENCE: 77

Ile Asp Glu Pro Thr Gly Gln Thr Ala Asp Trp Leu Thr Ile Ile
1 5 10 15

<210> SEQ ID NO 78
<211> LENGTH: 15
<212> TYPE: PRT
<213> ORGANISM: Artificial
<220> FEATURE:
<223> OTHER INFORMATION: Peptide pool

<400> SEQUENCE: 78

Thr Gly Gln Thr Ala Asp Trp Leu Thr Ile Ile Val Tyr Leu Thr
1 5 10 15

<210> SEQ ID NO 79
<211> LENGTH: 15
<212> TYPE: PRT
<213> ORGANISM: Artificial
<220> FEATURE:
<223> OTHER INFORMATION: Peptide pool

<400> SEQUENCE: 79

Ala Asp Trp Leu Thr Ile Ile Val Tyr Leu Thr Ser Phe Val Val
1 5 10 15

<210> SEQ ID NO 80
<211> LENGTH: 15
<212> TYPE: PRT
<213> ORGANISM: Artificial
<220> FEATURE:
<223> OTHER INFORMATION: Peptide pool

<400> SEQUENCE: 80

Thr Ile Ile Val Tyr Leu Thr Ser Phe Val Val Pro Ile Ile Leu
1 5 10 15

<210> SEQ ID NO 81
<211> LENGTH: 15
<212> TYPE: PRT
<213> ORGANISM: Artificial
<220> FEATURE:
<223> OTHER INFORMATION: Peptide pool

<400> SEQUENCE: 81

Tyr Leu Thr Ser Phe Val Val Pro Ile Ile Leu Lys Ala Leu Tyr
1 5 10 15

<210> SEQ ID NO 82
<211> LENGTH: 15
<212> TYPE: PRT
<213> ORGANISM: Artificial
<220> FEATURE:
<223> OTHER INFORMATION: Peptide pool

<400> SEQUENCE: 82

Phe Val Val Pro Ile Ile Leu Lys Ala Leu Tyr Met Leu Thr Thr
1 5 10 15

<210> SEQ ID NO 83
<211> LENGTH: 15
<212> TYPE: PRT
<213> ORGANISM: Artificial
<220> FEATURE:
<223> OTHER INFORMATION: Peptide pool

<400> SEQUENCE: 83

Ile Ile Leu Lys Ala Leu Tyr Met Leu Thr Thr Arg Gly Arg Gln
1 5 10 15

<210> SEQ ID NO 84
<211> LENGTH: 15
<212> TYPE: PRT
<213> ORGANISM: Artificial
<220> FEATURE:
<223> OTHER INFORMATION: Peptide pool

<400> SEQUENCE: 84

Ala Leu Tyr Met Leu Thr Thr Arg Gly Arg Gln Thr Ser Lys Asp 1 5 10 15

<210> SEQ ID NO 85
<211> LENGTH: 15
<212> TYPE: PRT
<213> ORGANISM: Artificial
<220> FEATURE:
<223> OTHER INFORMATION: Peptide pool

<400> SEQUENCE: 85

Leu Thr Thr Arg Gly Arg Gln Thr Ser Lys Asp Asn Lys Gly Met
1 5 10 15

<210> SEQ ID NO 86
<211> LENGTH: 15
<212> TYPE: PRT
<213> ORGANISM: Artificial
<220> FEATURE:
<223> OTHER INFORMATION: Peptide pool

<400> SEQUENCE: 86

Gly Arg Gln Thr Ser Lys Asp Asn Lys Gly Met Arg Ile Arg Phe
1 5 10 15

<210> SEQ ID NO 87
<211> LENGTH: 15
<212> TYPE: PRT
<213> ORGANISM: Artificial
<220> FEATURE:
<223> OTHER INFORMATION: Peptide pool

<400> SEQUENCE: 87

Ser Lys Asp Asn Lys Gly Met Arg Ile Arg Phe Lys Asp Asp Ser
1 5 10 15

<210> SEQ ID NO 88
<211> LENGTH: 15
<212> TYPE: PRT
<213> ORGANISM: Artificial
<220> FEATURE:
<223> OTHER INFORMATION: Peptide pool

<400> SEQUENCE: 88

Lys Gly Met Arg Ile Arg Phe Lys Asp Asp Ser Ser Tyr Glu Asp
1 5 10 15

<210> SEQ ID NO 89
<211> LENGTH: 15
<212> TYPE: PRT
<213> ORGANISM: Artificial
<220> FEATURE:
<223> OTHER INFORMATION: Peptide pool

<400> SEQUENCE: 89

Ile Arg Phe Lys Asp Asp Ser Ser Tyr Glu Asp Val Asn Gly Ile
1 5 10 15

<210> SEQ ID NO 90
<211> LENGTH: 15
<212> TYPE: PRT
<213> ORGANISM: Artificial
<220> FEATURE:
<223> OTHER INFORMATION: Peptide pool

<400> SEQUENCE: 90

Asp Asp Ser Ser Tyr Glu Asp Val Asn Gly Ile Arg Lys Pro Lys
1 5 10 15

<210> SEQ ID NO 91
<211> LENGTH: 15
<212> TYPE: PRT
<213> ORGANISM: Artificial
<220> FEATURE:
<223> OTHER INFORMATION: Peptide pool

<400> SEQUENCE: 91

Tyr Glu Asp Val Asn Gly Ile Arg Lys Pro Lys His Leu Tyr Val
1 5 10 15

<210> SEQ ID NO 92
<211> LENGTH: 15
<212> TYPE: PRT
<213> ORGANISM: Artificial
<220> FEATURE:
<223> OTHER INFORMATION: Peptide pool

<400> SEQUENCE: 92

Asn Gly Ile Arg Lys Pro Lys His Leu Tyr Val Ser Met Pro Asn
1 5 10 15

<210> SEQ ID NO 93
<211> LENGTH: 15
<212> TYPE: PRT
<213> ORGANISM: Artificial
<220> FEATURE:
<223> OTHER INFORMATION: Peptide pool

<400> SEQUENCE: 93

Lys Pro Lys His Leu Tyr Val Ser Met Pro Asn Ala Gln Ser Ser
1 5 10 15

<210> SEQ ID NO 94
<211> LENGTH: 15
<212> TYPE: PRT
<213> ORGANISM: Artificial
<220> FEATURE:
<223> OTHER INFORMATION: Peptide pool

<400> SEQUENCE: 94

Leu Tyr Val Ser Met Pro Asn Ala Gln Ser Ser Met Lys Ala Glu
1 5 10 15

<210> SEQ ID NO 95
<211> LENGTH: 15
<212> TYPE: PRT
<213> ORGANISM: Artificial
<220> FEATURE:
<223> OTHER INFORMATION: Peptide pool

<400> SEQUENCE: 95

Met Pro Asn Ala Gln Ser Ser Met Lys Ala Glu Glu Ile Thr Pro
1 5 10 15

<210> SEQ ID NO 96
<211> LENGTH: 15
<212> TYPE: PRT
<213> ORGANISM: Artificial
<220> FEATURE:
<223> OTHER INFORMATION: Peptide pool

<400> SEQUENCE: 96

Gln Ser Ser Met Lys Ala Glu Glu Ile Thr Pro Gly Arg Phe Arg
1 5 10 15

<210> SEQ ID NO 97
<211> LENGTH: 15
<212> TYPE: PRT
<213> ORGANISM: Artificial
<220> FEATURE:
<223> OTHER INFORMATION: Peptide pool

<400> SEQUENCE: 97

Lys Ala Glu Glu Ile Thr Pro Gly Arg Phe Arg Thr Ala Val Cys
1 5 10 15

<210> SEQ ID NO 98
<211> LENGTH: 15
<212> TYPE: PRT
<213> ORGANISM: Artificial
<220> FEATURE:
<223> OTHER INFORMATION: Peptide pool

<400> SEQUENCE: 98

Ile Thr Pro Gly Arg Phe Arg Thr Ala Val Cys Gly Leu Tyr Pro
1 5 10 15

<210> SEQ ID NO 99
<211> LENGTH: 15
<212> TYPE: PRT
<213> ORGANISM: Artificial
<220> FEATURE:
<223> OTHER INFORMATION: Peptide pool

<400> SEQUENCE: 99

Arg Phe Arg Thr Ala Val Cys Gly Leu Tyr Pro Ala Gln Ile Lys
1 5 10 15

<210> SEQ ID NO 100
<211> LENGTH: 15
<212> TYPE: PRT
<213> ORGANISM: Artificial
<220> FEATURE:
<223> OTHER INFORMATION: Peptide pool

<400> SEQUENCE: 100

Ala Val Cys Gly Leu Tyr Pro Ala Gln Ile Lys Ala Arg Asn Met
1 5 10 15

<210> SEQ ID NO 101
<211> LENGTH: 15
<212> TYPE: PRT
<213> ORGANISM: Artificial
<220> FEATURE:
<223> OTHER INFORMATION: Peptide pool

<400> SEQUENCE: 101

Leu Tyr Pro Ala Gln Ile Lys Ala Arg Asn Met Val Ser Pro Val
1 5 10 15

<210> SEQ ID NO 102
<211> LENGTH: 15
<212> TYPE: PRT
<213> ORGANISM: Artificial
<220> FEATURE:
<223> OTHER INFORMATION: Peptide pool

<400> SEQUENCE: 102

Gln Ile Lys Ala Arg Asn Met Val Ser Pro Val Met Ser Val Val
1 5 10 15

<210> SEQ ID NO 103
<211> LENGTH: 15
<212> TYPE: PRT
<213> ORGANISM: Artificial
<220> FEATURE:
<223> OTHER INFORMATION: Peptide pool

<400> SEQUENCE: 103

Arg Asn Met Val Ser Pro Val Met Ser Val Val Gly Phe Leu Ala
1               5                   10                  15

<210> SEQ ID NO 104
<211> LENGTH: 15
<212> TYPE: PRT
<213> ORGANISM: Artificial
<220> FEATURE:
<223> OTHER INFORMATION: Peptide pool

<400> SEQUENCE: 104

Ser Val Val Gly Phe Leu Ala Leu Ala Lys Asp Trp Thr Ser Arg
1               5                   10                  15

<210> SEQ ID NO 105
<211> LENGTH: 15
<212> TYPE: PRT
<213> ORGANISM: Artificial
<220> FEATURE:
<223> OTHER INFORMATION: Peptide pool

<400> SEQUENCE: 105

Phe Leu Ala Leu Ala Lys Asp Trp Thr Ser Arg Ile Glu Glu Trp
1               5                   10                  15

<210> SEQ ID NO 106
<211> LENGTH: 15
<212> TYPE: PRT
<213> ORGANISM: Artificial
<220> FEATURE:
<223> OTHER INFORMATION: Peptide pool

<400> SEQUENCE: 106

Ala Lys Asp Trp Thr Ser Arg Ile Glu Glu Trp Leu Gly Ala Pro
1               5                   10                  15

<210> SEQ ID NO 107
<211> LENGTH: 15
<212> TYPE: PRT
<213> ORGANISM: Artificial
<220> FEATURE:
<223> OTHER INFORMATION: Peptide pool

<400> SEQUENCE: 107

Thr Ser Arg Ile Glu Glu Trp Leu Gly Ala Pro Cys Lys Phe Met
1               5                   10                  15

<210> SEQ ID NO 108
<211> LENGTH: 15
<212> TYPE: PRT
<213> ORGANISM: Artificial
<220> FEATURE:
<223> OTHER INFORMATION: Peptide pool

<400> SEQUENCE: 108

Glu Glu Trp Leu Gly Ala Pro Cys Lys Phe Met Ala Glu Ser Pro
1               5                   10                  15

<210> SEQ ID NO 109

<211> LENGTH: 15
<212> TYPE: PRT
<213> ORGANISM: Artificial
<220> FEATURE:
<223> OTHER INFORMATION: Peptide pool

<400> SEQUENCE: 109

Gly Ala Pro Cys Lys Phe Met Ala Glu Ser Pro Ile Ala Gly Ser
1 5 10 15

<210> SEQ ID NO 110
<211> LENGTH: 15
<212> TYPE: PRT
<213> ORGANISM: Artificial
<220> FEATURE:
<223> OTHER INFORMATION: Peptide pool

<400> SEQUENCE: 110

Lys Phe Met Ala Glu Ser Pro Ile Ala Gly Ser Leu Ser Gly Asn
1 5 10 15

<210> SEQ ID NO 111
<211> LENGTH: 15
<212> TYPE: PRT
<213> ORGANISM: Artificial
<220> FEATURE:
<223> OTHER INFORMATION: Peptide pool

<400> SEQUENCE: 111

Glu Ser Pro Ile Ala Gly Ser Leu Ser Gly Asn Pro Val Asn Arg
1 5 10 15

<210> SEQ ID NO 112
<211> LENGTH: 15
<212> TYPE: PRT
<213> ORGANISM: Artificial
<220> FEATURE:
<223> OTHER INFORMATION: Peptide pool

<400> SEQUENCE: 112

Ala Gly Ser Leu Ser Gly Asn Pro Val Asn Arg Asp Tyr Ile Arg
1 5 10 15

<210> SEQ ID NO 113
<211> LENGTH: 15
<212> TYPE: PRT
<213> ORGANISM: Artificial
<220> FEATURE:
<223> OTHER INFORMATION: Peptide pool

<400> SEQUENCE: 113

Ser Gly Asn Pro Val Asn Arg Asp Tyr Ile Arg Gln Arg Gln Gly
1 5 10 15

<210> SEQ ID NO 114
<211> LENGTH: 15
<212> TYPE: PRT
<213> ORGANISM: Artificial
<220> FEATURE:
<223> OTHER INFORMATION: Peptide pool

<400> SEQUENCE: 114

Val Asn Arg Asp Tyr Ile Arg Gln Arg Gln Gly Ala Leu Ala Gly
1 5 10 15

<210> SEQ ID NO 115
<211> LENGTH: 15

<212> TYPE: PRT
<213> ORGANISM: Artificial
<220> FEATURE:
<223> OTHER INFORMATION: Peptide pool

<400> SEQUENCE: 115

Tyr Ile Arg Gln Arg Gln Gly Ala Leu Ala Gly Met Glu Pro Lys
1               5                   10                  15

<210> SEQ ID NO 116
<211> LENGTH: 15
<212> TYPE: PRT
<213> ORGANISM: Artificial
<220> FEATURE:
<223> OTHER INFORMATION: Peptide pool

<400> SEQUENCE: 116

Arg Gln Gly Ala Leu Ala Gly Met Glu Pro Lys Glu Phe Gln Ala
1               5                   10                  15

<210> SEQ ID NO 117
<211> LENGTH: 15
<212> TYPE: PRT
<213> ORGANISM: Artificial
<220> FEATURE:
<223> OTHER INFORMATION: Peptide pool

<400> SEQUENCE: 117

Leu Ala Gly Met Glu Pro Lys Glu Phe Gln Ala Leu Arg Gln His
1               5                   10                  15

<210> SEQ ID NO 118
<211> LENGTH: 15
<212> TYPE: PRT
<213> ORGANISM: Artificial
<220> FEATURE:
<223> OTHER INFORMATION: Peptide pool

<400> SEQUENCE: 118

Glu Pro Lys Glu Phe Gln Ala Leu Arg Gln His Ser Lys Asp Ala
1               5                   10                  15

<210> SEQ ID NO 119
<211> LENGTH: 15
<212> TYPE: PRT
<213> ORGANISM: Artificial
<220> FEATURE:
<223> OTHER INFORMATION: Peptide pool

<400> SEQUENCE: 119

Phe Gln Ala Leu Arg Gln His Ser Lys Asp Ala Gly Cys Thr Leu
1               5                   10                  15

<210> SEQ ID NO 120
<211> LENGTH: 15
<212> TYPE: PRT
<213> ORGANISM: Artificial
<220> FEATURE:
<223> OTHER INFORMATION: Peptide pool

<400> SEQUENCE: 120

Arg Gln His Ser Lys Asp Ala Gly Cys Thr Leu Val Glu His Ile
1               5                   10                  15

<210> SEQ ID NO 121
<211> LENGTH: 15
<212> TYPE: PRT

<213> ORGANISM: Artificial
<220> FEATURE:
<223> OTHER INFORMATION: Peptide pool

<400> SEQUENCE: 121

Lys Asp Ala Gly Cys Thr Leu Val Glu His Ile Glu Ser Pro Ser
1 5 10 15

<210> SEQ ID NO 122
<211> LENGTH: 15
<212> TYPE: PRT
<213> ORGANISM: Artificial
<220> FEATURE:
<223> OTHER INFORMATION: Peptide pool

<400> SEQUENCE: 122

Cys Thr Leu Val Glu His Ile Glu Ser Pro Ser Ser Ile Trp Val
1 5 10 15

<210> SEQ ID NO 123
<211> LENGTH: 15
<212> TYPE: PRT
<213> ORGANISM: Artificial
<220> FEATURE:
<223> OTHER INFORMATION: Peptide pool

<400> SEQUENCE: 123

Glu His Ile Glu Ser Pro Ser Ser Ile Trp Val Phe Ala Gly Ala
1 5 10 15

<210> SEQ ID NO 124
<211> LENGTH: 15
<212> TYPE: PRT
<213> ORGANISM: Artificial
<220> FEATURE:
<223> OTHER INFORMATION: Peptide pool

<400> SEQUENCE: 124

Ser Pro Ser Ser Ile Trp Val Phe Ala Gly Ala Pro Asp Arg Cys
1 5 10 15

<210> SEQ ID NO 125
<211> LENGTH: 15
<212> TYPE: PRT
<213> ORGANISM: Artificial
<220> FEATURE:
<223> OTHER INFORMATION: Peptide pool

<400> SEQUENCE: 125

Ile Trp Val Phe Ala Gly Ala Pro Asp Arg Cys Pro Pro Thr Cys
1 5 10 15

<210> SEQ ID NO 126
<211> LENGTH: 15
<212> TYPE: PRT
<213> ORGANISM: Artificial
<220> FEATURE:
<223> OTHER INFORMATION: Peptide pool

<400> SEQUENCE: 126

Ala Gly Ala Pro Asp Arg Cys Pro Pro Thr Cys Leu Phe Val Gly
1 5 10 15

<210> SEQ ID NO 127
<211> LENGTH: 15
<212> TYPE: PRT
<213> ORGANISM: Artificial

<220> FEATURE:
<223> OTHER INFORMATION: Peptide pool

<400> SEQUENCE: 127

Asp Arg Cys Pro Pro Thr Cys Leu Phe Val Gly Gly Met Ala Glu
1 5 10 15

<210> SEQ ID NO 128
<211> LENGTH: 15
<212> TYPE: PRT
<213> ORGANISM: Artificial
<220> FEATURE:
<223> OTHER INFORMATION: Peptide pool

<400> SEQUENCE: 128

Pro Thr Cys Leu Phe Val Gly Gly Met Ala Glu Leu Gly Ala Phe
1 5 10 15

<210> SEQ ID NO 129
<211> LENGTH: 15
<212> TYPE: PRT
<213> ORGANISM: Artificial
<220> FEATURE:
<223> OTHER INFORMATION: Peptide pool

<400> SEQUENCE: 129

Phe Val Gly Gly Met Ala Glu Leu Gly Ala Phe Phe Ser Ile Leu
1 5 10 15

<210> SEQ ID NO 130
<211> LENGTH: 15
<212> TYPE: PRT
<213> ORGANISM: Artificial
<220> FEATURE:
<223> OTHER INFORMATION: Peptide pool

<400> SEQUENCE: 130

Met Ala Glu Leu Gly Ala Phe Phe Ser Ile Leu Gln Asp Met Arg
1 5 10 15

<210> SEQ ID NO 131
<211> LENGTH: 15
<212> TYPE: PRT
<213> ORGANISM: Artificial
<220> FEATURE:
<223> OTHER INFORMATION: Peptide pool

<400> SEQUENCE: 131

Gly Ala Phe Phe Ser Ile Leu Gln Asp Met Arg Asn Thr Ile Met
1 5 10 15

<210> SEQ ID NO 132
<211> LENGTH: 15
<212> TYPE: PRT
<213> ORGANISM: Artificial
<220> FEATURE:
<223> OTHER INFORMATION: Peptide pool

<400> SEQUENCE: 132

Ser Ile Leu Gln Asp Met Arg Asn Thr Ile Met Ala Ser Lys Thr
1 5 10 15

<210> SEQ ID NO 133
<211> LENGTH: 15
<212> TYPE: PRT
<213> ORGANISM: Artificial
<220> FEATURE:

<223> OTHER INFORMATION: Peptide pool

<400> SEQUENCE: 133

Asp Met Arg Asn Thr Ile Met Ala Ser Lys Thr Val Gly Thr Ala
1 5 10 15

<210> SEQ ID NO 134
<211> LENGTH: 15
<212> TYPE: PRT
<213> ORGANISM: Artificial
<220> FEATURE:
<223> OTHER INFORMATION: Peptide pool

<400> SEQUENCE: 134

Thr Ile Met Ala Ser Lys Thr Val Gly Thr Ala Asp Glu Lys Leu
1 5 10 15

<210> SEQ ID NO 135
<211> LENGTH: 15
<212> TYPE: PRT
<213> ORGANISM: Artificial
<220> FEATURE:
<223> OTHER INFORMATION: Peptide pool

<400> SEQUENCE: 135

Ser Lys Thr Val Gly Thr Ala Asp Glu Lys Leu Arg Lys Lys Ser
1 5 10 15

<210> SEQ ID NO 136
<211> LENGTH: 15
<212> TYPE: PRT
<213> ORGANISM: Artificial
<220> FEATURE:
<223> OTHER INFORMATION: Peptide pool

<400> SEQUENCE: 136

Gly Thr Ala Asp Glu Lys Leu Arg Lys Lys Ser Ser Phe Tyr Gln
1 5 10 15

<210> SEQ ID NO 137
<211> LENGTH: 15
<212> TYPE: PRT
<213> ORGANISM: Artificial
<220> FEATURE:
<223> OTHER INFORMATION: Peptide pool

<400> SEQUENCE: 137

Glu Lys Leu Arg Lys Lys Ser Ser Phe Tyr Gln Ser Tyr Leu Arg
1 5 10 15

<210> SEQ ID NO 138
<211> LENGTH: 15
<212> TYPE: PRT
<213> ORGANISM: Artificial
<220> FEATURE:
<223> OTHER INFORMATION: Peptide pool

<400> SEQUENCE: 138

Lys Lys Ser Ser Phe Tyr Gln Ser Tyr Leu Arg Arg Thr Gln Ser
1 5 10 15

<210> SEQ ID NO 139
<211> LENGTH: 15
<212> TYPE: PRT
<213> ORGANISM: Artificial
<220> FEATURE:
<223> OTHER INFORMATION: Peptide pool

<400> SEQUENCE: 139

Phe Tyr Gln Ser Tyr Leu Arg Arg Thr Gln Ser Met Gly Ile Gln
1 5 10 15

<210> SEQ ID NO 140
<211> LENGTH: 15
<212> TYPE: PRT
<213> ORGANISM: Artificial
<220> FEATURE:
<223> OTHER INFORMATION: Peptide pool

<400> SEQUENCE: 140

Tyr Leu Arg Arg Thr Gln Ser Met Gly Ile Gln Leu Asp Gln Arg
1 5 10 15

<210> SEQ ID NO 141
<211> LENGTH: 15
<212> TYPE: PRT
<213> ORGANISM: Artificial
<220> FEATURE:
<223> OTHER INFORMATION: Peptide pool

<400> SEQUENCE: 141

Thr Gln Ser Met Gly Ile Gln Leu Asp Gln Arg Ile Ile Val Met
1 5 10 15

<210> SEQ ID NO 142
<211> LENGTH: 15
<212> TYPE: PRT
<213> ORGANISM: Artificial
<220> FEATURE:
<223> OTHER INFORMATION: Peptide pool

<400> SEQUENCE: 142

Gly Ile Gln Leu Asp Gln Arg Ile Ile Val Met Phe Met Val Ala
1 5 10 15

<210> SEQ ID NO 143
<211> LENGTH: 15
<212> TYPE: PRT
<213> ORGANISM: Artificial
<220> FEATURE:
<223> OTHER INFORMATION: Peptide pool

<400> SEQUENCE: 143

Asp Gln Arg Ile Ile Val Met Phe Met Val Ala Trp Gly Lys Glu
1 5 10 15

<210> SEQ ID NO 144
<211> LENGTH: 15
<212> TYPE: PRT
<213> ORGANISM: Artificial
<220> FEATURE:
<223> OTHER INFORMATION: Peptide pool

<400> SEQUENCE: 144

Ile Val Met Phe Met Val Ala Trp Gly Lys Glu Ala Val Asp Asn
1 5 10 15

<210> SEQ ID NO 145
<211> LENGTH: 15
<212> TYPE: PRT
<213> ORGANISM: Artificial
<220> FEATURE:
<223> OTHER INFORMATION: Peptide pool

<400> SEQUENCE: 145

Met Val Ala Trp Gly Lys Glu Ala Val Asp Asn Phe His Leu Gly
1 5 10 15

<210> SEQ ID NO 146
<211> LENGTH: 15
<212> TYPE: PRT
<213> ORGANISM: Artificial
<220> FEATURE:
<223> OTHER INFORMATION: Peptide pool

<400> SEQUENCE: 146

Gly Lys Glu Ala Val Asp Asn Phe His Leu Gly Asp Asp Met Asp
1 5 10 15

<210> SEQ ID NO 147
<211> LENGTH: 15
<212> TYPE: PRT
<213> ORGANISM: Artificial
<220> FEATURE:
<223> OTHER INFORMATION: Peptide pool

<400> SEQUENCE: 147

Val Asp Asn Phe His Leu Gly Asp Asp Met Asp Pro Glu Leu Arg
1 5 10 15

<210> SEQ ID NO 148
<211> LENGTH: 15
<212> TYPE: PRT
<213> ORGANISM: Artificial
<220> FEATURE:
<223> OTHER INFORMATION: Peptide pool

<400> SEQUENCE: 148

His Leu Gly Asp Asp Met Asp Pro Glu Leu Arg Ser Leu Ala Gln
1 5 10 15

<210> SEQ ID NO 149
<211> LENGTH: 15
<212> TYPE: PRT
<213> ORGANISM: Artificial
<220> FEATURE:
<223> OTHER INFORMATION: Peptide pool

<400> SEQUENCE: 149

Asp Met Asp Pro Glu Leu Arg Ser Leu Ala Gln Ile Leu Ile Asp
1 5 10 15

<210> SEQ ID NO 150
<211> LENGTH: 15
<212> TYPE: PRT
<213> ORGANISM: Artificial
<220> FEATURE:
<223> OTHER INFORMATION: Peptide pool

<400> SEQUENCE: 150

Glu Leu Arg Ser Leu Ala Gln Ile Leu Ile Asp Gln Lys Val Lys
1 5 10 15

<210> SEQ ID NO 151
<211> LENGTH: 15
<212> TYPE: PRT
<213> ORGANISM: Artificial
<220> FEATURE:
<223> OTHER INFORMATION: Peptide pool

<400> SEQUENCE: 151

Leu Ala Gln Ile Leu Ile Asp Gln Lys Val Lys Glu Ile Ser Asn
1 5 10 15

<210> SEQ ID NO 152
<211> LENGTH: 15
<212> TYPE: PRT
<213> ORGANISM: Artificial
<220> FEATURE:
<223> OTHER INFORMATION: Peptide pool

<400> SEQUENCE: 152

Leu Ile Asp Gln Lys Val Lys Glu Ile Ser Asn Gln Glu Pro Met
1 5 10 15

<210> SEQ ID NO 153
<211> LENGTH: 15
<212> TYPE: PRT
<213> ORGANISM: Artificial
<220> FEATURE:
<223> OTHER INFORMATION: Peptide pool

<400> SEQUENCE: 153

Lys Val Lys Glu Ile Ser Asn Gln Glu Pro Met Lys Leu Met Leu
1 5 10 15

<210> SEQ ID NO 154
<211> LENGTH: 15
<212> TYPE: PRT
<213> ORGANISM: Artificial
<220> FEATURE:
<223> OTHER INFORMATION: Peptide pool

<400> SEQUENCE: 154

Ile Ser Asn Gln Glu Pro Met Lys Leu Met Leu Ser Tyr Gly Asn
1 5 10 15

<210> SEQ ID NO 155
<211> LENGTH: 15
<212> TYPE: PRT
<213> ORGANISM: Artificial
<220> FEATURE:
<223> OTHER INFORMATION: Peptide pool

<400> SEQUENCE: 155

Glu Pro Met Lys Leu Met Leu Ser Tyr Gly Asn Val Leu Asp Leu
1 5 10 15

<210> SEQ ID NO 156
<211> LENGTH: 15
<212> TYPE: PRT
<213> ORGANISM: Artificial
<220> FEATURE:
<223> OTHER INFORMATION: Peptide pool

<400> SEQUENCE: 156

Leu Met Leu Ser Tyr Gly Asn Val Leu Asp Leu Asn His Leu Asp
1 5 10 15

<210> SEQ ID NO 157
<211> LENGTH: 15
<212> TYPE: PRT
<213> ORGANISM: Artificial
<220> FEATURE:
<223> OTHER INFORMATION: Peptide pool

<400> SEQUENCE: 157

Tyr Gly Asn Val Leu Asp Leu Asn His Leu Asp Ile Asp Glu Pro
1 5 10 15

<210> SEQ ID NO 158
<211> LENGTH: 15
<212> TYPE: PRT
<213> ORGANISM: Artificial
<220> FEATURE:
<223> OTHER INFORMATION: Peptide pool

<400> SEQUENCE: 158

Leu Asp Leu Asn His Leu Asp Ile Asp Glu Pro Thr Gly Gln Thr
1 5 10 15

<210> SEQ ID NO 159
<211> LENGTH: 15
<212> TYPE: PRT
<213> ORGANISM: Artificial
<220> FEATURE:
<223> OTHER INFORMATION: Peptide pool

<400> SEQUENCE: 159

His Leu Asp Ile Asp Glu Pro Thr Gly Gln Thr Ala Asp Trp Leu
1 5 10 15

<210> SEQ ID NO 160
<211> LENGTH: 15
<212> TYPE: PRT
<213> ORGANISM: Artificial
<220> FEATURE:
<223> OTHER INFORMATION: Peptide pool

<400> SEQUENCE: 160

Asp Glu Pro Thr Gly Gln Thr Ala Asp Trp Leu Gly Ile Val Ile
1 5 10 15

<210> SEQ ID NO 161
<211> LENGTH: 15
<212> TYPE: PRT
<213> ORGANISM: Artificial
<220> FEATURE:
<223> OTHER INFORMATION: Peptide pool

<400> SEQUENCE: 161

Gly Gln Thr Ala Asp Trp Leu Gly Ile Val Ile Tyr Leu Thr Ser
1 5 10 15

<210> SEQ ID NO 162
<211> LENGTH: 15
<212> TYPE: PRT
<213> ORGANISM: Artificial
<220> FEATURE:
<223> OTHER INFORMATION: Peptide pool

<400> SEQUENCE: 162

Asp Trp Leu Gly Ile Val Ile Tyr Leu Thr Ser Phe Val Val Pro
1 5 10 15

<210> SEQ ID NO 163
<211> LENGTH: 15
<212> TYPE: PRT
<213> ORGANISM: Artificial
<220> FEATURE:
<223> OTHER INFORMATION: Peptide pool

<400> SEQUENCE: 163

Ile Val Ile Tyr Leu Thr Ser Phe Val Val Pro Ile Leu Leu Lys 1 5 10 15

<210> SEQ ID NO 164
<211> LENGTH: 15
<212> TYPE: PRT
<213> ORGANISM: Artificial
<220> FEATURE:
<223> OTHER INFORMATION: Peptide pool

<400> SEQUENCE: 164

Leu Thr Ser Phe Val Val Pro Ile Leu Leu Lys Ala Leu Tyr Met
1 5 10 15

<210> SEQ ID NO 165
<211> LENGTH: 15
<212> TYPE: PRT
<213> ORGANISM: Artificial
<220> FEATURE:
<223> OTHER INFORMATION: Peptide pool

<400> SEQUENCE: 165

Val Val Pro Ile Leu Leu Lys Ala Leu Tyr Met Leu Thr Thr Arg
1 5 10 15

<210> SEQ ID NO 166
<211> LENGTH: 15
<212> TYPE: PRT
<213> ORGANISM: Artificial
<220> FEATURE:
<223> OTHER INFORMATION: Peptide pool

<400> SEQUENCE: 166

Leu Leu Lys Ala Leu Tyr Met Leu Thr Thr Arg Gly Arg Gln Thr
1 5 10 15

<210> SEQ ID NO 167
<211> LENGTH: 15
<212> TYPE: PRT
<213> ORGANISM: Artificial
<220> FEATURE:
<223> OTHER INFORMATION: Peptide pool

<400> SEQUENCE: 167

Leu Tyr Met Leu Thr Thr Arg Gly Arg Gln Thr Thr Lys Asp Asn
1 5 10 15

<210> SEQ ID NO 168
<211> LENGTH: 15
<212> TYPE: PRT
<213> ORGANISM: Artificial
<220> FEATURE:
<223> OTHER INFORMATION: Peptide pool

<400> SEQUENCE: 168

Thr Thr Arg Gly Arg Gln Thr Thr Lys Asp Asn Lys Gly Thr Arg
1 5 10 15

<210> SEQ ID NO 169
<211> LENGTH: 15
<212> TYPE: PRT
<213> ORGANISM: Artificial
<220> FEATURE:
<223> OTHER INFORMATION: Peptide pool

<400> SEQUENCE: 169

Arg Gln Thr Thr Lys Asp Asn Lys Gly Thr Arg Ile Arg Phe Lys
1 5 10 15

<210> SEQ ID NO 170
<211> LENGTH: 15
<212> TYPE: PRT
<213> ORGANISM: Artificial
<220> FEATURE:
<223> OTHER INFORMATION: Peptide pool

<400> SEQUENCE: 170

Lys Asp Asn Lys Gly Thr Arg Ile Arg Phe Lys Asp Asp Ser Ser
1 5 10 15

<210> SEQ ID NO 171
<211> LENGTH: 15
<212> TYPE: PRT
<213> ORGANISM: Artificial
<220> FEATURE:
<223> OTHER INFORMATION: Peptide pool

<400> SEQUENCE: 171

Gly Thr Arg Ile Arg Phe Lys Asp Asp Ser Ser Phe Glu Asp Val
1 5 10 15

<210> SEQ ID NO 172
<211> LENGTH: 15
<212> TYPE: PRT
<213> ORGANISM: Artificial
<220> FEATURE:
<223> OTHER INFORMATION: Peptide pool

<400> SEQUENCE: 172

Arg Phe Lys Asp Asp Ser Ser Phe Glu Asp Val Asn Gly Ile Arg
1 5 10 15

<210> SEQ ID NO 173
<211> LENGTH: 15
<212> TYPE: PRT
<213> ORGANISM: Artificial
<220> FEATURE:
<223> OTHER INFORMATION: Peptide pool

<400> SEQUENCE: 173

Asp Ser Ser Phe Glu Asp Val Asn Gly Ile Arg Lys Pro Lys His
1 5 10 15

<210> SEQ ID NO 174
<211> LENGTH: 15
<212> TYPE: PRT
<213> ORGANISM: Artificial
<220> FEATURE:
<223> OTHER INFORMATION: Peptide pool

<400> SEQUENCE: 174

Glu Asp Val Asn Gly Ile Arg Lys Pro Lys His Leu Tyr Val Ser
1 5 10 15

<210> SEQ ID NO 175
<211> LENGTH: 15
<212> TYPE: PRT
<213> ORGANISM: Artificial
<220> FEATURE:
<223> OTHER INFORMATION: Peptide pool

<400> SEQUENCE: 175

Gly Ile Arg Lys Pro Lys His Leu Tyr Val Ser Leu Pro Asn Ala
1 5 10 15

<210> SEQ ID NO 176
<211> LENGTH: 15
<212> TYPE: PRT
<213> ORGANISM: Artificial
<220> FEATURE:
<223> OTHER INFORMATION: Peptide pool

<400> SEQUENCE: 176

Pro Lys His Leu Tyr Val Ser Leu Pro Asn Ala Gln Ser Ser Met
1 5 10 15

<210> SEQ ID NO 177
<211> LENGTH: 15
<212> TYPE: PRT
<213> ORGANISM: Artificial
<220> FEATURE:
<223> OTHER INFORMATION: Peptide pool

<400> SEQUENCE: 177

Tyr Val Ser Leu Pro Asn Ala Gln Ser Ser Met Lys Ala Glu Glu
1 5 10 15

<210> SEQ ID NO 178
<211> LENGTH: 15
<212> TYPE: PRT
<213> ORGANISM: Artificial
<220> FEATURE:
<223> OTHER INFORMATION: Peptide pool

<400> SEQUENCE: 178

Pro Asn Ala Gln Ser Ser Met Lys Ala Glu Glu Ile Thr Pro Gly
1 5 10 15

<210> SEQ ID NO 179
<211> LENGTH: 15
<212> TYPE: PRT
<213> ORGANISM: Artificial
<220> FEATURE:
<223> OTHER INFORMATION: Peptide pool

<400> SEQUENCE: 179

Ser Ser Met Lys Ala Glu Glu Ile Thr Pro Gly Arg Tyr Arg Thr
1 5 10 15

<210> SEQ ID NO 180
<211> LENGTH: 15
<212> TYPE: PRT
<213> ORGANISM: Artificial
<220> FEATURE:
<223> OTHER INFORMATION: Peptide pool

<400> SEQUENCE: 180

Ala Glu Glu Ile Thr Pro Gly Arg Tyr Arg Thr Ala Ile Cys Gly
1 5 10 15

<210> SEQ ID NO 181
<211> LENGTH: 15
<212> TYPE: PRT
<213> ORGANISM: Artificial
<220> FEATURE:
<223> OTHER INFORMATION: Peptide pool

<400> SEQUENCE: 181

Thr Pro Gly Arg Tyr Arg Thr Ala Ile Cys Gly Leu Tyr Pro Ala
1 5 10 15

<210> SEQ ID NO 182
<211> LENGTH: 15
<212> TYPE: PRT
<213> ORGANISM: Artificial
<220> FEATURE:
<223> OTHER INFORMATION: Peptide pool

<400> SEQUENCE: 182

Tyr Arg Thr Ala Ile Cys Gly Leu Tyr Pro Ala Gln Ile Lys Ala
1 5 10 15

<210> SEQ ID NO 183
<211> LENGTH: 15
<212> TYPE: PRT
<213> ORGANISM: Artificial
<220> FEATURE:
<223> OTHER INFORMATION: Peptide pool

<400> SEQUENCE: 183

Ile Cys Gly Leu Tyr Pro Ala Gln Ile Lys Ala Arg Gln Met Ile
1 5 10 15

<210> SEQ ID NO 184
<211> LENGTH: 15
<212> TYPE: PRT
<213> ORGANISM: Artificial
<220> FEATURE:
<223> OTHER INFORMATION: Peptide pool

<400> SEQUENCE: 184

Tyr Pro Ala Gln Ile Lys Ala Arg Gln Met Ile Ser Pro Val Met
1 5 10 15

<210> SEQ ID NO 185
<211> LENGTH: 15
<212> TYPE: PRT
<213> ORGANISM: Artificial
<220> FEATURE:
<223> OTHER INFORMATION: Peptide pool

<400> SEQUENCE: 185

Ile Lys Ala Arg Gln Met Ile Ser Pro Val Met Ser Val Ile Gly
1 5 10 15

<210> SEQ ID NO 186
<211> LENGTH: 15
<212> TYPE: PRT
<213> ORGANISM: Artificial
<220> FEATURE:
<223> OTHER INFORMATION: Peptide pool

<400> SEQUENCE: 186

Gln Met Ile Ser Pro Val Met Ser Val Ile Gly Phe Leu Ala Leu
1 5 10 15

<210> SEQ ID NO 187
<211> LENGTH: 15
<212> TYPE: PRT
<213> ORGANISM: Artificial
<220> FEATURE:
<223> OTHER INFORMATION: Peptide pool

<400> SEQUENCE: 187

Val Ile Gly Phe Leu Ala Leu Ala Lys Asp Trp Ser Asp Arg Ile
1 5 10 15

<210> SEQ ID NO 188

<211> LENGTH: 15
<212> TYPE: PRT
<213> ORGANISM: Artificial
<220> FEATURE:
<223> OTHER INFORMATION: Peptide pool

<400> SEQUENCE: 188

Leu Ala Leu Ala Lys Asp Trp Ser Asp Arg Ile Glu Gln Trp Leu
1 5 10 15

<210> SEQ ID NO 189
<211> LENGTH: 15
<212> TYPE: PRT
<213> ORGANISM: Artificial
<220> FEATURE:
<223> OTHER INFORMATION: Peptide pool

<400> SEQUENCE: 189

Lys Asp Trp Ser Asp Arg Ile Glu Gln Trp Leu Ser Glu Pro Cys
1 5 10 15

<210> SEQ ID NO 190
<211> LENGTH: 15
<212> TYPE: PRT
<213> ORGANISM: Artificial
<220> FEATURE:
<223> OTHER INFORMATION: Peptide pool

<400> SEQUENCE: 190

Asp Arg Ile Glu Gln Trp Leu Ser Glu Pro Cys Lys Leu Leu Pro
1 5 10 15

<210> SEQ ID NO 191
<211> LENGTH: 15
<212> TYPE: PRT
<213> ORGANISM: Artificial
<220> FEATURE:
<223> OTHER INFORMATION: Peptide pool

<400> SEQUENCE: 191

Gln Trp Leu Ser Glu Pro Cys Lys Leu Leu Pro Asp Thr Ala Ala
1 5 10 15

<210> SEQ ID NO 192
<211> LENGTH: 15
<212> TYPE: PRT
<213> ORGANISM: Artificial
<220> FEATURE:
<223> OTHER INFORMATION: Peptide pool

<400> SEQUENCE: 192

Glu Pro Cys Lys Leu Leu Pro Asp Thr Ala Ala Val Ser Leu Leu
1 5 10 15

<210> SEQ ID NO 193
<211> LENGTH: 15
<212> TYPE: PRT
<213> ORGANISM: Artificial
<220> FEATURE:
<223> OTHER INFORMATION: Peptide pool

<400> SEQUENCE: 193

Leu Leu Pro Asp Thr Ala Ala Val Ser Leu Leu Gly Gly Pro Ala
1 5 10 15

<210> SEQ ID NO 194
<211> LENGTH: 15

<212> TYPE: PRT
<213> ORGANISM: Artificial
<220> FEATURE:
<223> OTHER INFORMATION: Peptide pool

<400> SEQUENCE: 194

Thr Ala Ala Val Ser Leu Leu Gly Gly Pro Ala Thr Asn Arg Asp
1 5 10 15

<210> SEQ ID NO 195
<211> LENGTH: 15
<212> TYPE: PRT
<213> ORGANISM: Artificial
<220> FEATURE:
<223> OTHER INFORMATION: Peptide pool

<400> SEQUENCE: 195

Ser Leu Leu Gly Gly Pro Ala Thr Asn Arg Asp Tyr Leu Arg Gln
1 5 10 15

<210> SEQ ID NO 196
<211> LENGTH: 15
<212> TYPE: PRT
<213> ORGANISM: Artificial
<220> FEATURE:
<223> OTHER INFORMATION: Peptide pool

<400> SEQUENCE: 196

Gly Pro Ala Thr Asn Arg Asp Tyr Leu Arg Gln Arg Gln Val Ala
1 5 10 15

<210> SEQ ID NO 197
<211> LENGTH: 15
<212> TYPE: PRT
<213> ORGANISM: Artificial
<220> FEATURE:
<223> OTHER INFORMATION: Peptide pool

<400> SEQUENCE: 197

Asn Arg Asp Tyr Leu Arg Gln Arg Gln Val Ala Leu Gly Asn Met
1 5 10 15

<210> SEQ ID NO 198
<211> LENGTH: 15
<212> TYPE: PRT
<213> ORGANISM: Artificial
<220> FEATURE:
<223> OTHER INFORMATION: Peptide pool

<400> SEQUENCE: 198

Leu Arg Gln Arg Gln Val Ala Leu Gly Asn Met Glu Thr Lys Glu
1 5 10 15

<210> SEQ ID NO 199
<211> LENGTH: 15
<212> TYPE: PRT
<213> ORGANISM: Artificial
<220> FEATURE:
<223> OTHER INFORMATION: Peptide pool

<400> SEQUENCE: 199

Gln Val Ala Leu Gly Asn Met Glu Thr Lys Glu Ser Lys Ala Ile
1 5 10 15

<210> SEQ ID NO 200
<211> LENGTH: 15
<212> TYPE: PRT

<213> ORGANISM: Artificial
<220> FEATURE:
<223> OTHER INFORMATION: Peptide pool

<400> SEQUENCE: 200

Gly Asn Met Glu Thr Lys Glu Ser Lys Ala Ile Arg Gln His Ala
1 5 10 15

<210> SEQ ID NO 201
<211> LENGTH: 15
<212> TYPE: PRT
<213> ORGANISM: Artificial
<220> FEATURE:
<223> OTHER INFORMATION: Peptide pool

<400> SEQUENCE: 201

Thr Lys Glu Ser Lys Ala Ile Arg Gln His Ala Glu Ala Ala Gly
1 5 10 15

<210> SEQ ID NO 202
<211> LENGTH: 15
<212> TYPE: PRT
<213> ORGANISM: Artificial
<220> FEATURE:
<223> OTHER INFORMATION: Peptide pool

<400> SEQUENCE: 202

Lys Ala Ile Arg Gln His Ala Glu Ala Ala Gly Cys Ser Met Ile
1 5 10 15

<210> SEQ ID NO 203
<211> LENGTH: 15
<212> TYPE: PRT
<213> ORGANISM: Artificial
<220> FEATURE:
<223> OTHER INFORMATION: Peptide pool

<400> SEQUENCE: 203

Gln His Ala Glu Ala Ala Gly Cys Ser Met Ile Glu Asp Ile Glu
1 5 10 15

<210> SEQ ID NO 204
<211> LENGTH: 15
<212> TYPE: PRT
<213> ORGANISM: Artificial
<220> FEATURE:
<223> OTHER INFORMATION: Peptide pool

<400> SEQUENCE: 204

Ala Ala Gly Cys Ser Met Ile Glu Asp Ile Glu Ser Pro Ser Ser
1 5 10 15

<210> SEQ ID NO 205
<211> LENGTH: 15
<212> TYPE: PRT
<213> ORGANISM: Artificial
<220> FEATURE:
<223> OTHER INFORMATION: Peptide pool

<400> SEQUENCE: 205

Ser Met Ile Glu Asp Ile Glu Ser Pro Ser Ser Ile Trp Val Phe
1 5 10 15

<210> SEQ ID NO 206
<211> LENGTH: 15
<212> TYPE: PRT
<213> ORGANISM: Artificial

<220> FEATURE:
<223> OTHER INFORMATION: Peptide pool

<400> SEQUENCE: 206

Asp Ile Glu Ser Pro Ser Ser Ile Trp Val Phe Ala Gly Ala Pro
1 5 10 15

<210> SEQ ID NO 207
<211> LENGTH: 15
<212> TYPE: PRT
<213> ORGANISM: Artificial
<220> FEATURE:
<223> OTHER INFORMATION: Peptide pool

<400> SEQUENCE: 207

Pro Ser Ser Ile Trp Val Phe Ala Gly Ala Pro Asp Arg Cys Pro
1 5 10 15

<210> SEQ ID NO 208
<211> LENGTH: 15
<212> TYPE: PRT
<213> ORGANISM: Artificial
<220> FEATURE:
<223> OTHER INFORMATION: Peptide pool

<400> SEQUENCE: 208

Trp Val Phe Ala Gly Ala Pro Asp Arg Cys Pro Pro Thr Cys Leu
1 5 10 15

<210> SEQ ID NO 209
<211> LENGTH: 15
<212> TYPE: PRT
<213> ORGANISM: Artificial
<220> FEATURE:
<223> OTHER INFORMATION: Peptide pool

<400> SEQUENCE: 209

Gly Ala Pro Asp Arg Cys Pro Pro Thr Cys Leu Phe Ile Ala Gly
1 5 10 15

<210> SEQ ID NO 210
<211> LENGTH: 15
<212> TYPE: PRT
<213> ORGANISM: Artificial
<220> FEATURE:
<223> OTHER INFORMATION: Peptide pool

<400> SEQUENCE: 210

Arg Cys Pro Pro Thr Cys Leu Phe Ile Ala Gly Met Ala Glu Leu
1 5 10 15

<210> SEQ ID NO 211
<211> LENGTH: 15
<212> TYPE: PRT
<213> ORGANISM: Artificial
<220> FEATURE:
<223> OTHER INFORMATION: Peptide pool

<400> SEQUENCE: 211

Thr Cys Leu Phe Ile Ala Gly Met Ala Glu Leu Gly Ala Phe Phe
1 5 10 15

<210> SEQ ID NO 212
<211> LENGTH: 15
<212> TYPE: PRT
<213> ORGANISM: Artificial
<220> FEATURE:

<223> OTHER INFORMATION: Peptide pool

<400> SEQUENCE: 212

Ile Ala Gly Met Ala Glu Leu Gly Ala Phe Phe Ser Ile Leu Gln
1 5 10 15

<210> SEQ ID NO 213
<211> LENGTH: 15
<212> TYPE: PRT
<213> ORGANISM: Artificial
<220> FEATURE:
<223> OTHER INFORMATION: Peptide pool

<400> SEQUENCE: 213

Ala Glu Leu Gly Ala Phe Phe Ser Ile Leu Gln Asp Met Arg Asn
1 5 10 15

<210> SEQ ID NO 214
<211> LENGTH: 15
<212> TYPE: PRT
<213> ORGANISM: Artificial
<220> FEATURE:
<223> OTHER INFORMATION: Peptide pool

<400> SEQUENCE: 214

Ala Phe Phe Ser Ile Leu Gln Asp Met Arg Asn Thr Ile Met Ala
1 5 10 15

<210> SEQ ID NO 215
<211> LENGTH: 15
<212> TYPE: PRT
<213> ORGANISM: Artificial
<220> FEATURE:
<223> OTHER INFORMATION: Peptide pool

<400> SEQUENCE: 215

Ile Leu Gln Asp Met Arg Asn Thr Ile Met Ala Ser Lys Thr Val
1 5 10 15

<210> SEQ ID NO 216
<211> LENGTH: 15
<212> TYPE: PRT
<213> ORGANISM: Artificial
<220> FEATURE:
<223> OTHER INFORMATION: Peptide pool

<400> SEQUENCE: 216

Met Arg Asn Thr Ile Met Ala Ser Lys Thr Val Gly Thr Ser Glu
1 5 10 15

<210> SEQ ID NO 217
<211> LENGTH: 15
<212> TYPE: PRT
<213> ORGANISM: Artificial
<220> FEATURE:
<223> OTHER INFORMATION: Peptide pool

<400> SEQUENCE: 217

Ile Met Ala Ser Lys Thr Val Gly Thr Ser Glu Glu Lys Leu Arg
1 5 10 15

<210> SEQ ID NO 218
<211> LENGTH: 15
<212> TYPE: PRT
<213> ORGANISM: Artificial
<220> FEATURE:
<223> OTHER INFORMATION: Peptide pool

<400> SEQUENCE: 218

Lys Thr Val Gly Thr Ser Glu Glu Lys Leu Arg Lys Lys Ser Ser
1 5 10 15

<210> SEQ ID NO 219
<211> LENGTH: 15
<212> TYPE: PRT
<213> ORGANISM: Artificial
<220> FEATURE:
<223> OTHER INFORMATION: Peptide pool

<400> SEQUENCE: 219

Thr Ser Glu Glu Lys Leu Arg Lys Lys Ser Ser Phe Tyr Gln Ser
1 5 10 15

<210> SEQ ID NO 220
<211> LENGTH: 15
<212> TYPE: PRT
<213> ORGANISM: Artificial
<220> FEATURE:
<223> OTHER INFORMATION: Peptide pool

<400> SEQUENCE: 220

Lys Leu Arg Lys Lys Ser Ser Phe Tyr Gln Ser Tyr Leu Arg Arg
1 5 10 15

<210> SEQ ID NO 221
<211> LENGTH: 15
<212> TYPE: PRT
<213> ORGANISM: Artificial
<220> FEATURE:
<223> OTHER INFORMATION: Peptide pool

<400> SEQUENCE: 221

Lys Ser Ser Phe Tyr Gln Ser Tyr Leu Arg Arg Thr Gln Ser Met
1 5 10 15

<210> SEQ ID NO 222
<211> LENGTH: 15
<212> TYPE: PRT
<213> ORGANISM: Artificial
<220> FEATURE:
<223> OTHER INFORMATION: Peptide pool

<400> SEQUENCE: 222

Tyr Gln Ser Tyr Leu Arg Arg Thr Gln Ser Met Gly Ile Gln Leu
1 5 10 15

<210> SEQ ID NO 223
<211> LENGTH: 15
<212> TYPE: PRT
<213> ORGANISM: Artificial
<220> FEATURE:
<223> OTHER INFORMATION: Peptide pool

<400> SEQUENCE: 223

Leu Arg Arg Thr Gln Ser Met Gly Ile Gln Leu Asp Gln Arg Ile
1 5 10 15

<210> SEQ ID NO 224
<211> LENGTH: 15
<212> TYPE: PRT
<213> ORGANISM: Artificial
<220> FEATURE:
<223> OTHER INFORMATION: Peptide pool

<400> SEQUENCE: 224

Gln Ser Met Gly Ile Gln Leu Asp Gln Arg Ile Ile Val Leu Phe
1 5 10 15

<210> SEQ ID NO 225
<211> LENGTH: 15
<212> TYPE: PRT
<213> ORGANISM: Artificial
<220> FEATURE:
<223> OTHER INFORMATION: Peptide pool

<400> SEQUENCE: 225

Ile Gln Leu Asp Gln Arg Ile Ile Val Leu Phe Met Val Ala Trp
1 5 10 15

<210> SEQ ID NO 226
<211> LENGTH: 15
<212> TYPE: PRT
<213> ORGANISM: Artificial
<220> FEATURE:
<223> OTHER INFORMATION: Peptide pool

<400> SEQUENCE: 226

Gln Arg Ile Ile Val Leu Phe Met Val Ala Trp Gly Lys Glu Ala
1 5 10 15

<210> SEQ ID NO 227
<211> LENGTH: 15
<212> TYPE: PRT
<213> ORGANISM: Artificial
<220> FEATURE:
<223> OTHER INFORMATION: Peptide pool

<400> SEQUENCE: 227

Val Leu Phe Met Val Ala Trp Gly Lys Glu Ala Val Asp Asn Phe
1 5 10 15

<210> SEQ ID NO 228
<211> LENGTH: 15
<212> TYPE: PRT
<213> ORGANISM: Artificial
<220> FEATURE:
<223> OTHER INFORMATION: Peptide pool

<400> SEQUENCE: 228

Val Ala Trp Gly Lys Glu Ala Val Asp Asn Phe His Leu Gly Asp
1 5 10 15

<210> SEQ ID NO 229
<211> LENGTH: 15
<212> TYPE: PRT
<213> ORGANISM: Artificial
<220> FEATURE:
<223> OTHER INFORMATION: Peptide pool

<400> SEQUENCE: 229

Lys Glu Ala Val Asp Asn Phe His Leu Gly Asp Asp Met Asp Pro
1 5 10 15

<210> SEQ ID NO 230
<211> LENGTH: 15
<212> TYPE: PRT
<213> ORGANISM: Artificial
<220> FEATURE:
<223> OTHER INFORMATION: Peptide pool

<400> SEQUENCE: 230

Asp Asn Phe His Leu Gly Asp Asp Met Asp Pro Glu Leu Arg Thr
1 5 10 15

<210> SEQ ID NO 231
<211> LENGTH: 15
<212> TYPE: PRT
<213> ORGANISM: Artificial
<220> FEATURE:
<223> OTHER INFORMATION: Peptide pool

<400> SEQUENCE: 231

Leu Gly Asp Asp Met Asp Pro Glu Leu Arg Thr Leu Ala Gln Ser
1 5 10 15

<210> SEQ ID NO 232
<211> LENGTH: 15
<212> TYPE: PRT
<213> ORGANISM: Artificial
<220> FEATURE:
<223> OTHER INFORMATION: Peptide pool

<400> SEQUENCE: 232

Met Asp Pro Glu Leu Arg Thr Leu Ala Gln Ser Leu Ile Asp Val
1 5 10 15

<210> SEQ ID NO 233
<211> LENGTH: 15
<212> TYPE: PRT
<213> ORGANISM: Artificial
<220> FEATURE:
<223> OTHER INFORMATION: Peptide pool

<400> SEQUENCE: 233

Leu Arg Thr Leu Ala Gln Ser Leu Ile Asp Val Lys Val Lys Glu
1 5 10 15

<210> SEQ ID NO 234
<211> LENGTH: 15
<212> TYPE: PRT
<213> ORGANISM: Artificial
<220> FEATURE:
<223> OTHER INFORMATION: Peptide pool

<400> SEQUENCE: 234

Ala Gln Ser Leu Ile Asp Val Lys Val Lys Glu Ile Ser Asn Gln
1 5 10 15

<210> SEQ ID NO 235
<211> LENGTH: 15
<212> TYPE: PRT
<213> ORGANISM: Artificial
<220> FEATURE:
<223> OTHER INFORMATION: Peptide pool

<400> SEQUENCE: 235

Ile Asp Val Lys Val Lys Glu Ile Ser Asn Gln Glu Pro Leu Lys
1 5 10 15